United States Patent
Donello et al.

(10) Patent No.: US 8,563,594 B2
(45) Date of Patent: Oct. 22, 2013

(54) S1P3 RECEPTOR INHIBITORS FOR TREATING PAIN

(75) Inventors: John E. Donello, Dana Point, CA (US); Richard L. Beard, Newport Beach, CA (US); Fabien J. Schweighoffer, Val-de-marne (FR)

(73) Assignee: Allergan, Inc., Irvine, CA (US)

( * ) Notice: Subject to any disclaimer, the term of this patent is extended or adjusted under 35 U.S.C. 154(b) by 614 days.

(21) Appl. No.: 12/599,468

(22) PCT Filed: May 7, 2008

(86) PCT No.: PCT/US2008/062800
§ 371 (c)(1),
(2), (4) Date: Nov. 9, 2009

(87) PCT Pub. No.: WO2008/141013
PCT Pub. Date: Nov. 20, 2008

(65) Prior Publication Data
US 2010/0249069 A1    Sep. 30, 2010

Related U.S. Application Data

(60) Provisional application No. 60/916,592, filed on May 8, 2007.

(51) Int. Cl.
*A01N 43/38* (2006.01)
*A01N 37/18* (2006.01)
*A61K 31/405* (2006.01)
*A61K 31/165* (2006.01)
*C07D 209/04* (2006.01)
*C07D 233/00* (2006.01)
*C07D 235/00* (2006.01)
*C07D 237/00* (2006.01)
*C07D 239/00* (2006.01)

(52) U.S. Cl.
USPC ............ 514/415; 514/617; 548/469; 564/180

(58) Field of Classification Search
USPC ................. 514/415, 617; 548/469; 564/180
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 5,026,722 A * | 6/1991 | Oxford et al. ................. 514/397 |
| 7,091,232 B2 | 8/2006 | Chow et al. |
| 7,544,803 B2 * | 6/2009 | Hulme et al. ................. 546/159 |
| 7,737,173 B2 * | 6/2010 | Beard et al. .................. 514/419 |
| 2005/0222422 A1 | 10/2005 | Lynch et al. |
| 2007/0088002 A1 | 4/2007 | Lynch et al. |
| 2007/0191313 A1 | 8/2007 | Beard et al. |
| 2007/0232682 A1 | 10/2007 | Beard et al. |

FOREIGN PATENT DOCUMENTS

| EP | 1 142 890 | 10/2001 |
| WO | WO 96/24585 | 8/1996 |
| WO | WO 02/055502 | 7/2002 |
| WO | WO 03/016254 | 2/2003 |
| WO | WO 2004/060366 | 7/2004 |
| WO | WO 2004/096220 | 11/2004 |
| WO | WO 2005/004810 | 1/2005 |
| WO | WO 2005/023761 | 3/2005 |
| WO | WO 2008/016883 | 2/2008 |
| WO | WO 2008/030843 | 3/2008 |

OTHER PUBLICATIONS

U.S. Appl. No. 60/884,470, filed Jan. 11, 2007, Allergan, Inc.
U.S. Appl. No. 60/824,807, filed Sep. 7, 2006, Allergan, Inc.
Kim et al, Pain, 150, pp. 355-363, 1992.
Remington's Pharmaceutical Sciences, Mack Publishing Company, Easton, Pa, 16$^{th}$ Edition, 1980.
Wu et al, "Suramin Inhibits Spinal Cord Microglia Activation and Long-Term Hyperalgesia Induced by Formalin Injection", *Journal of Pain*, vol. 5, No. 1, pp. 48-55, Feb. 2004.
Salomone et al, "S1P3 receptors, mediate the potent constriction of cerebral arteries by sphingosine-1-phosphate", *European Journal of Pharmacology*, vol. 469, No. 1-3, pp. 125-134, 2003.
Zhang et al, "Sphingosine-1-phosphate via activation of a G-protein-coupled receptor(s) enhances the excitability of rat sensory neurons", *Journal of Neurophysiology*, vol. 96, No. 3, pp. 1042-1052, 2006.

* cited by examiner

*Primary Examiner* — Kendra D Carter
(74) *Attorney, Agent, or Firm* — Krishna G. Banerjee

(57) ABSTRACT

Disclosed herein are compositions and methods for treating pain using S1P3 receptor inhibitors.

2 Claims, No Drawings

S1P3 RECEPTOR INHIBITORS FOR TREATING PAIN

CROSS-REFERENCE

This application claims the benefit of U.S. Application Ser. No. 60/916,592, filed May 8, 2007, which is hereby incorporated by reference in its entirety.

Disclosed herein is a method for treating pain, the method comprising administering to a patient in need of such treatment an S1P3 receptor inhibitor.

DETAILED DESCRIPTION OF THE INVENTION

S1P3 Receptor

Sphingosine-1-phosphate ("S1P") is an important chemical messenger that can activate particular cell surface transmembrane G-protein coupled receptors known as endothelial gene differentiation ("Edg") receptors.

There are five known S1P receptors activated by S1P: S1P1, also known as Edg 1 (human Edg-1, GenBank Accession No. AF233365); S1P2, also known as Edg 5 (human Edg-5, GenBank Accession No. AF034780); S1P3, also known as Edg 3 (human Edg-3, GenBank Accession No. X83864); S1P4, also known as Edg 6 (human Edg-6, GenBank Accession No. AF000479); and S1P5, also known as Edg 8 (human Edg-8, GenBank Accession No. AF317676).

The method of the present invention treats pain by administering compounds that inhibit the S1P3 receptor. In one embodiment, the method administers compounds that selectively inhibit the S1P3 subtype as compared to at least the S1P1 and S1P2 subtypes.

S1P3 Receptor Inhibitors

A compound is an "S1P3 receptor inhibitor" if it inhibits, partially or completely, the cellular response caused by binding of S1P or other ligand to the S1P3 receptor.

S1P3 is a G-protein coupled receptor (GPCR). When a ligand binds to that receptor it induces a conformational shift, causing GDP to be replaced by GTP on the α-subunit of the associated G-proteins and subsequent release of the G-proteins into the cytoplasm. The α-subunit then dissociates from the βγ-subunit and each subunit can then associate with effector proteins, activating second messengers, and leading to a cellular response. The process is referred to as S1P cell signaling.

One example of a cellular response is the accumulation of cAMP. The effect of an inhibitor on this response can be measured by well-known techniques in the art. One example is radioimmunoassay and the [γ-$^{35}$S]GTP binding assay, illustrated in U.S. Patent Application Publication No. 2005/0222422 and No. 2007/0088002 to assay S1P agonists (the disclosures of both these publications are incorporated by reference). To evaluate a compound for its potential as an inhibitor, one can measure cAMP accumulation by radioimmunoassay after incubating S1P (or S1P receptor agonist) in the presence of a test compound and cells expressing the S1P3 receptor; if the compound is an inhibitor, it will reduce the activation of S1P3 by S1P, which can be measured as reduced cAMP accumulation.

Another method of determining if a compound is an S1P3 receptor inhibitor is with a FLIPR assay. An example of this method is described in U.S. patent application Ser. No. 11/675,168, the contents of which are incorporated herein by reference. According to that application, compounds may be assessed for their ability to activate or block activation of the human S1P3 receptor in T24 cells stably expressing the human S1P3 receptor. In this assay ten thousand cells/well are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 μg/ml geneticin. On the day of the experiment, the cells are washed twice with Hank's Balanced Salt Solution supplemented with 20 mM HEPES (HBSS/Hepes buffer). The cells are then dye loaded with 2 uM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, S1P, is diluted in HBSS/Hepes buffer with 4 mg/ml fatty acid free bovine serum albumin. The FLIPR transfers 12.5 μl from the ligand microplate to the cell plate and takes fluorescent measurements for 75 seconds, taking readings every second, and then for 2.5 minutes, taking readings every 10 seconds. Drugs are tested over the concentration range of 0.61 nM to 10,000 nM. Data for $Ca^{+2}$ responses is obtained in arbitrary fluorescence units and not translated into $Ca^{+2}$ concentrations. $IC_{50}$ values are determined through a linear regression analysis using the Levenburg Marquardt algorithm.

S1P3 receptor inhibitors include S1P3 receptor antagonists and S1P3 receptor inverse agonists, as long as they inhibit, partially or completely, S1P cell signaling.

S1P3 receptor inhibitors may be selective for the S1P3 receptor or they may inhibit S1P cell signaling at more than one of the S1P receptor subtypes. An inhibitor is selective for the S1P3 receptor compared to another S1P subtype if the inhibitor is more than 100 times as potent at inhibiting the S1P3 receptor than it is at inhibiting or activating the other S1P receptor subtype. For example, the $IC_{50}$ of hypothetical compound A in a FLIPR assay is 100 nM at the S1P3 receptor, >5000 nM at the S1P1 receptor, and 200 nM at the S1P5 receptor; compound A is selective for the S1P3 receptor compared to the S1P1 receptor but not compared to the S1P5 receptor. If, to take another example, the $IC_{50}$ of hypothetical compound B is 100 nM at the S1P3 receptor and $EC_{50}$ is 200 nM at the S1P1 receptor and >5000 at the S1P2 receptor, then compound B is selective for the S1P3 receptor compared to the S1P2 receptor but not the S1P1 receptor.

In one embodiment, the S1P3 receptor inhibitors are selective for the S1P3 receptor as compared to the S1P1 receptor. In another embodiment, the S13P receptor inhibitors are selective for the S1P3 receptor as compared to the S1P2 receptor. In another embodiment, the S13P receptor inhibitors are selective for the S1P3 receptor as compared to both the S1P1 and the S1P2 receptors.

S13P Receptor Inhibitors Useful in the Method of the Invention

S1P3 receptor inhibitors useful in the method of the invention include those disclosed in U.S. patent application Ser. No. 11/675,168, No. 11/690,637, No. 60/884,470, and No. 60/824,807, and in U.S. Patent Application Publication No. 2005/022422. The disclosures of all the foregoing references are incorporated by reference.

DEFINITIONS

In describing S13P receptor inhibitors useful in the invention, the following terms have the following meanings, unless otherwise indicated.

"Me" refers to methyl.
"Et" refers to ethyl.
"tBu" refers to t-butyl.
"iPr" refers to i-propyl.
"Ph" refers to phenyl.

"Alkyl" refers to a straight-chain, branched or cyclic saturated aliphatic hydrocarbon. The alkyl group may have 1 to 12 carbons; in other embodiments, it is a lower alkyl of from 1 to 7 carbons, or a lower alkyl from 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon-carbon double bond. The alkenyl group may have 2 to 12 carbons; in other embodiments, it is a lower alkenyl of from 2 to 7 carbons, or a lower alkenyl of from 2 to 4 carbons. The alkenyl group may be optionally substituted with one or more substituents selected from the group consisting of hydroxyl, cyano, alkoxy, O, S, $NO_2$, halogen, dimethyl amino and SH.

"Alkynyl" refers to a straight-chain, branched or cyclic unsaturated hydrocarbon containing at least one carbon-carbon triple bond. The alkynyl group may have 2 to 12 carbons; in other embodiments, it is a lower alkynyl of from 2 to 7 carbons, or a lower alkynyl of from 2 to 4 carbons. The alkynyl group may be optionally substituted with one or more substituents selected from the group consisting of hydroxyl, cyano, alkoxy, O, S, $NO_2$, halogen, dimethyl amino and SH.

"Alkoxy" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" (Alkylaryl) refers to an alkyl that is covalently joined to an aryl group. In one embodiment, the alkyl is a lower alkyl.

"Aryloxy" refers to an "O-aryl" group.

"Arylalkyloxy" refers to an "O-alkaryl" (O-alkylaryl) group.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. The hydrocarbyl radical may have from 1 to 20 carbon atoms, or from 1 to 12 carbon atoms, or from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Ester" refers to —C(O)—O—R', wherein R' is alkyl, aryl or alkylaryl.

"Carboxy" refers to —C(O)—O—H "Thioamide" refers to —C(S)—NH—R', wherein R' is alkyl, aryl, alkylaryl or hydrogen.

"Thiol ester" refers to —C(O)—S—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'''', wherein R'''' is alkyl, aryl, C(CN)=C-aryl, $CH_2CN$, or alkyaryl.

"Sulfoxyl" refers to —S(O)—R'''', wherein R'''' is alkyl, alkenyl, alkynyl, aryl, or alkylaryl.

"Sulfonamidyl" refers to —S(O)—NR'(R"), wherein R' and R" are independently alkyl, alkenyl, alkynyl, aryl, or alkylaryl.

"Carbocyclic" refers to any ring, aromatic or non-aromatic, containing 1 to 12 carbon atoms.

"Heterocyclic" refers to any ring, aromatic or non-aromatic, containing 1 to 12 carbon atoms and 1 to 4 heteroatoms chosen from a group consisting of oxygen, nitrogen and sulfur.

Indole-3-Carboxylic Acid Amide, Ester, Thioamide and Thiol Ester Compounds Bearing Aryl or Heteroaryl Groups U.S. patent application Ser. No. 11/675,168 discloses S1P3 receptor antagonists having the following formula:

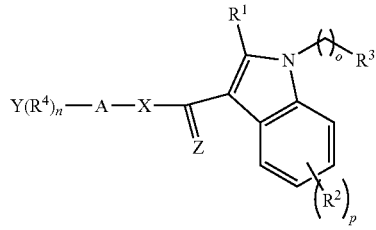

wherein
X is $NR^5$, O, S;
Z is O or S;
n is 0 or an integer of from 1 to 4;
o is 0 or an integer of from 1 to 3;
p is 0 or an integer of from 1 to 4;
A is $(C(R^5)_2)_m$, wherein
m is 0 or an integer of from 1 to 6;
$R^5$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, wherein said aryl is a carbocyclic aryl or heterocyclic aryl group wherein said carbocylic aryl comprises from 6 to 20 atoms and said heterocyclic aryl comprises from 2 to 20 carbon atoms and from 1 to 5 heteroatoms selected from the group consisting of nitrogen, oxygen and sulfur, halo, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl and sulfonyl groups;

Y is a carbocyclic aryl or heterocyclic aryl group wherein said carbocylic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;

$R^1$, $R^2$, $R^3$, $R^4$ are selected from the group consisting of hydrogen; straight or branched chain alkyl having 1 to 12 carbons; cycloalkyl having 3 to 6 carbons; alkenyl having 2 to 6 carbons and 1 or 2 double bonds; alkynyl having 2 to 6 carbons and 1 or 2 triple bonds; aryl wherein said aryl is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur; halo; $C_1$ to $C_{12}$ haloalkyl; hydroxyl; $C_1$ to $C_{12}$ alkoxy; $C_3$ to $C_{20}$ arylalkyloxy; $C_1$ to $C_{12}$ alkylcarbonyl; formyl; oxycarbonyl; carboxy; $C_1$ to $C_{12}$ alkyl carboxylate; $C_1$ to $C_{12}$ alkyl amide; aminocarbonyl; amino; cyano; diazo; nitro; thio; sulfoxyl; sulfonyl groups; or a group selected from the group consisting of

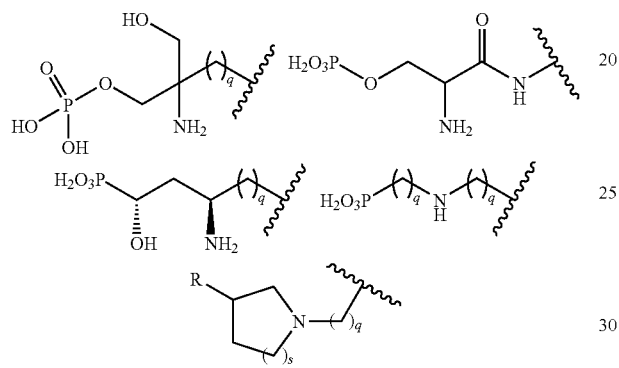

wherein R is $CO_2H$ or $PO_3H_2$, p is an integer of 1 or 2 and q is 0 or an integer of 1 to 5 and s is 0 or an integer of 1 or 2; provided that, if Y is phenyl, it must be substituted with at least one $R^4$ group that is not hydrogen.

Examples of such compounds include the following

| NO. | COMPOUND |
|---|---|
| 1 | 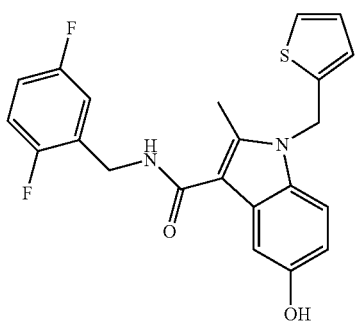 |
| 2 | 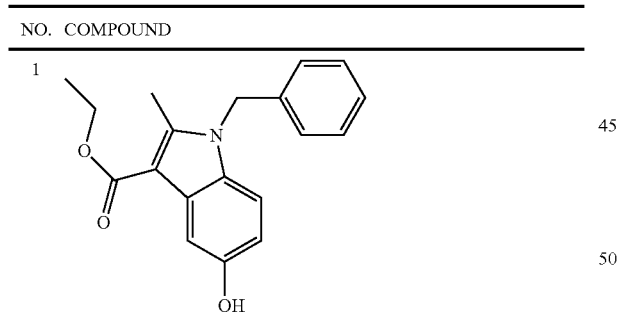 |
| 3 | 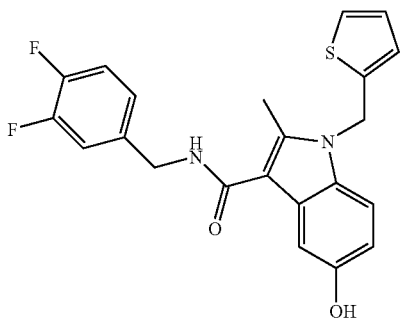 [SMILES: Cc1c(C(=O)NCc2ccc(F)c(F)c2)c2cc(O)ccc2n1Cc1cccs1] |
| 4 | 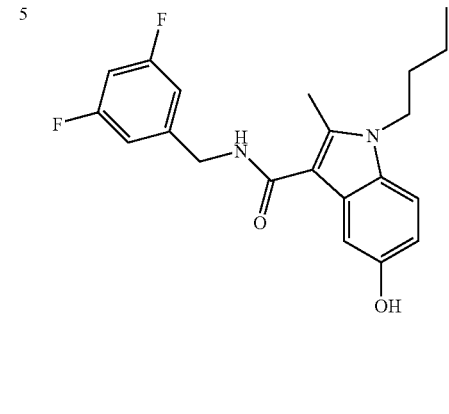 |
| 5 | 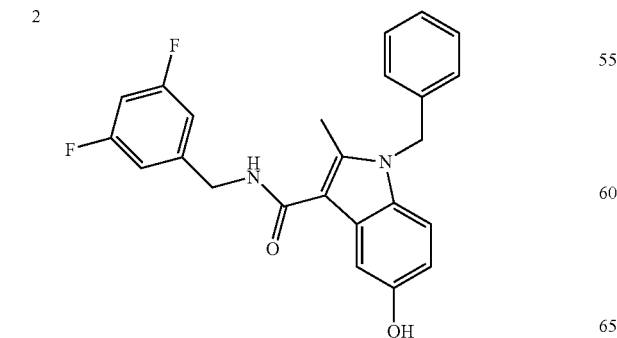 |
| 6 | 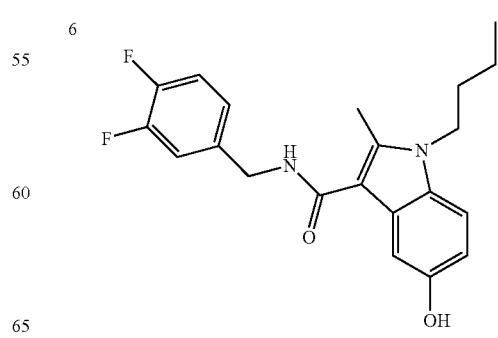 |

-continued
| NO. | COMPOUND |
|---|---|
| 7 | 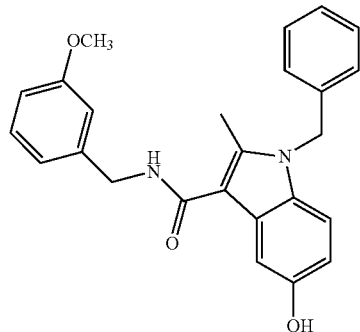 [SMILES: COc1cccc(CNC(=O)c2c(C)n(Cc3ccccc3)c3ccc(O)cc23)c1] |
| 8 | 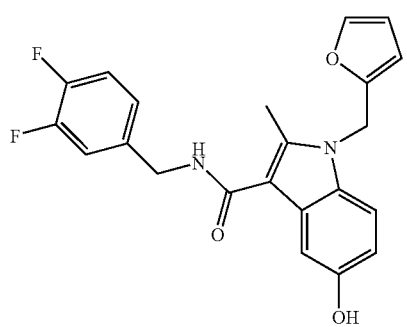 [SMILES: Cc1c(C(=O)NCc2ccc(F)c(F)c2)c2cc(O)ccc2n1Cc1ccco1] |
| 9 | 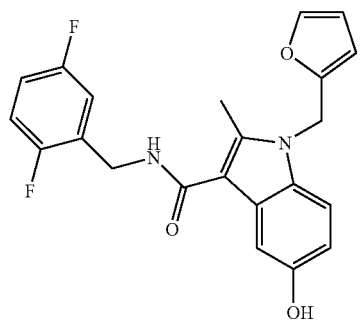 [SMILES: Cc1c(C(=O)NCc2cc(F)ccc2F)c2cc(O)ccc2n1Cc1ccco1] |
| 10 | 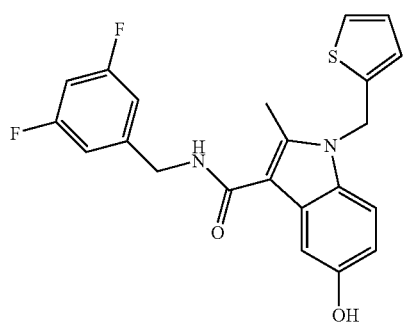 [SMILES: Cc1c(C(=O)NCc2cc(F)cc(F)c2)c2cc(O)ccc2n1Cc1cccs1] |
-continued
| NO. | COMPOUND |
|---|---|
| 11 | 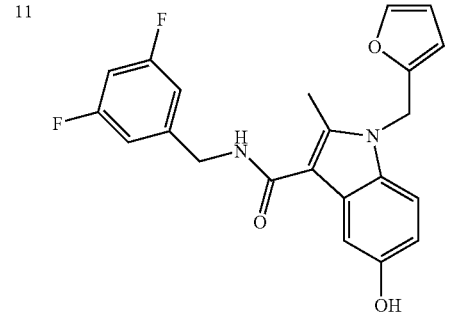 |
| 12 | |
| 13 | |
| 14 | |

-continued
| NO. | COMPOUND |
|---|---|
| 15 | 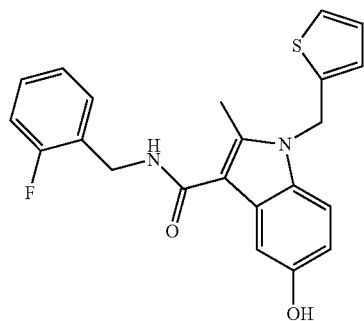 [SMILES: Cc1c(C(=O)NCc2ccccc2F)c2cc(O)ccc2n1Cc1cccs1] |
| 16 | 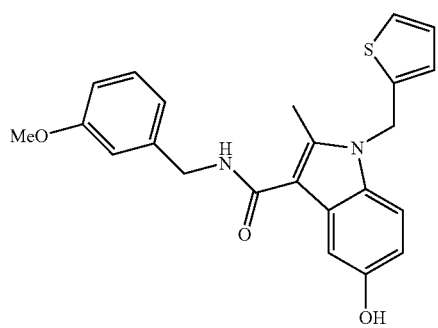 [SMILES: COc1cccc(CNC(=O)c2c(C)n(Cc3cccs3)c3ccc(O)cc23)c1] |
| 17 | 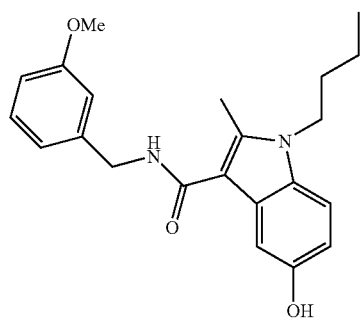 [SMILES: CCCCn1c(C)c(C(=O)NCc2cccc(OC)c2)c2cc(O)ccc21] |
| 18 | 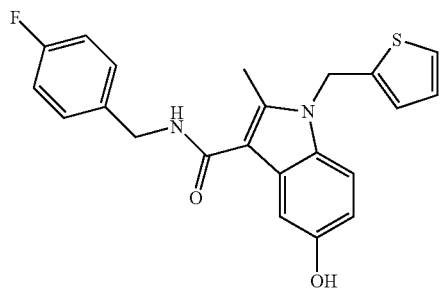 [SMILES: Cc1c(C(=O)NCc2ccc(F)cc2)c2cc(O)ccc2n1Cc1cccs1] |
| 19 | 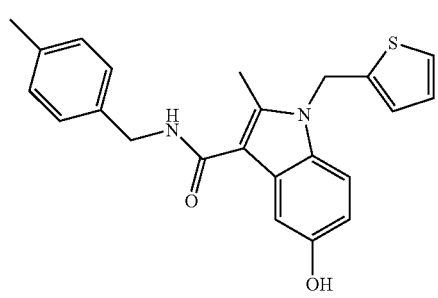 [SMILES: Cc1ccc(CNC(=O)c2c(C)n(Cc3cccs3)c3ccc(O)cc23)cc1] |
-continued
| NO. | COMPOUND |
|---|---|
| 20 | 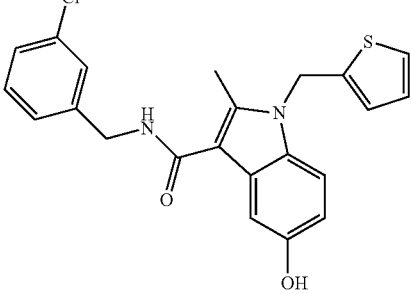 |
| 21 | 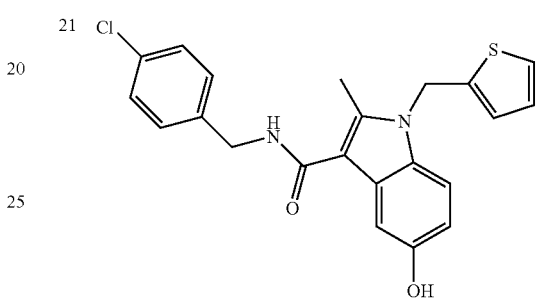 |
| 22 | 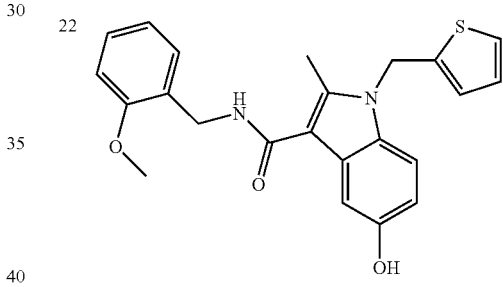 |
| 23 | 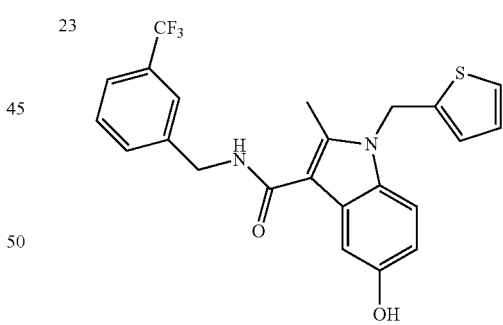 |
| 24 | 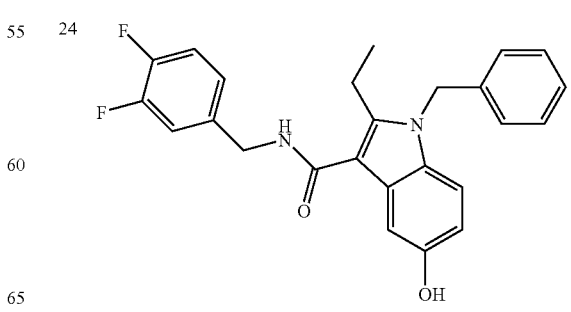 |

| NO. | COMPOUND |
|-----|----------|
| 25 | 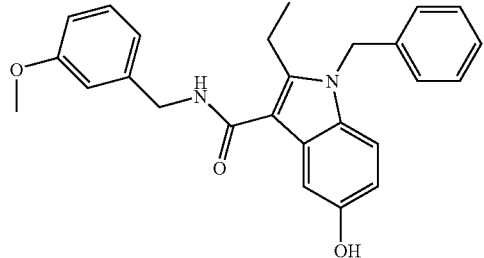 [SMILES: CCc1c(C(=O)NCc2cccc(OC)c2)c2cc(O)ccc2n1Cc1ccccc1] |
| 26 | 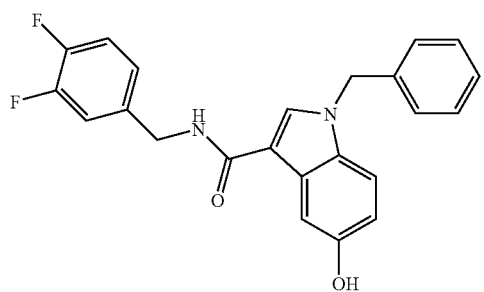 [SMILES: O=C(NCc1ccc(F)c(F)c1)c1cn(Cc2ccccc2)c2ccc(O)cc12] |
| 27 | 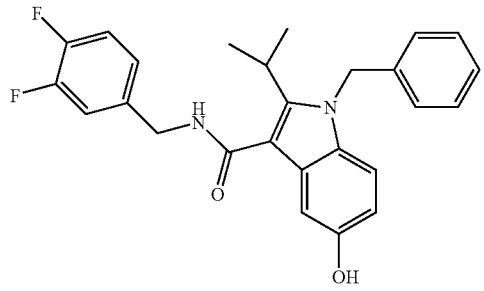 [SMILES: CC(C)c1c(C(=O)NCc2ccc(F)c(F)c2)c2cc(O)ccc2n1Cc1ccccc1] |
| 28 | 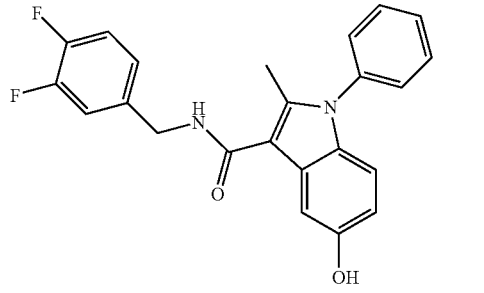 [SMILES: Cc1c(C(=O)NCc2ccc(F)c(F)c2)c2cc(O)ccc2n1-c1ccccc1] |
| 29 | 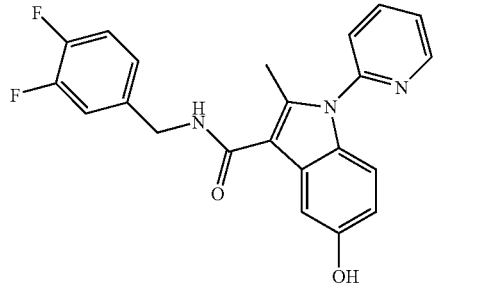 [SMILES: Cc1c(C(=O)NCc2ccc(F)c(F)c2)c2cc(O)ccc2n1-c1ccccn1] |
| NO. | COMPOUND |
|-----|----------|
| 30 | 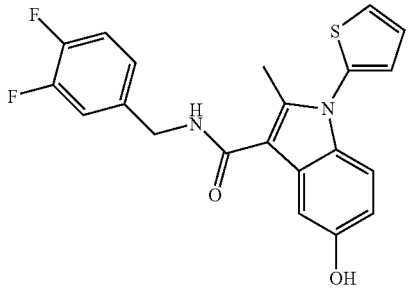 [SMILES: Cc1c(C(=O)NCc2ccc(F)c(F)c2)c2cc(O)ccc2n1-c1cccs1] |
| 31 | 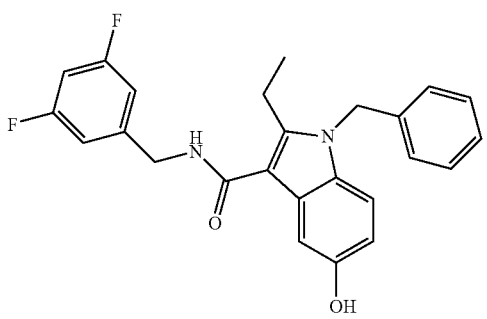 [SMILES: CCc1c(C(=O)NCc2cc(F)cc(F)c2)c2cc(O)ccc2n1Cc1ccccc1] |
| 32 | 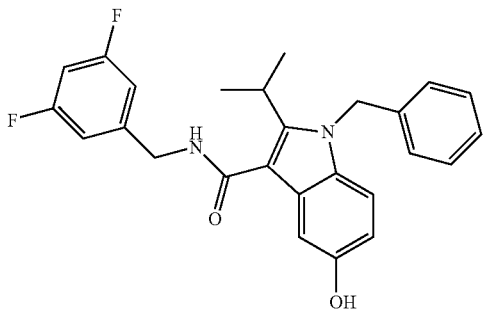 [SMILES: CC(C)c1c(C(=O)NCc2cc(F)cc(F)c2)c2cc(O)ccc2n1Cc1ccccc1] |
| 33 | 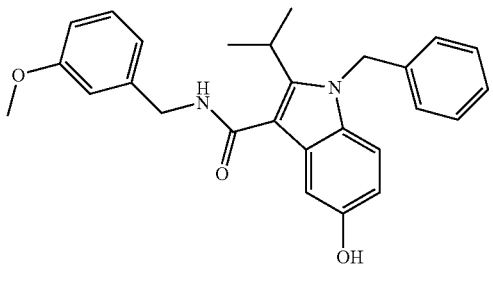 [SMILES: COc1cccc(CNC(=O)c2c(C(C)C)n(Cc3ccccc3)c3ccc(O)cc23)c1] |
| 34 | 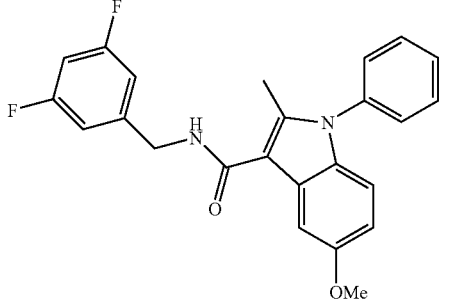 [SMILES: COc1ccc2c(c1)c(C(=O)NCc1cc(F)cc(F)c1)c(C)n2-c1ccccc1] |

| NO. | COMPOUND |
|---|---|
| 35 | 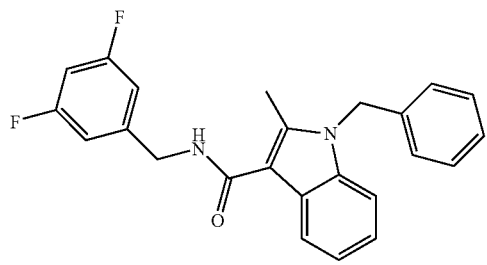 [SMILES: Cc1c(C(=O)NCc2cc(F)cc(F)c2)c2ccccc2n1Cc1ccccc1] |
| 36 | 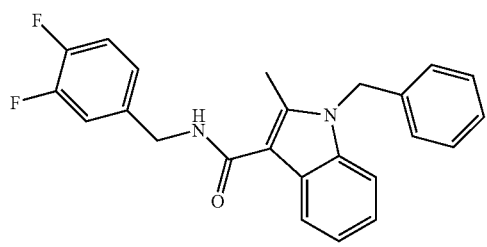 [SMILES: Cc1c(C(=O)NCc2ccc(F)c(F)c2)c2ccccc2n1Cc1ccccc1] |
| 37 | 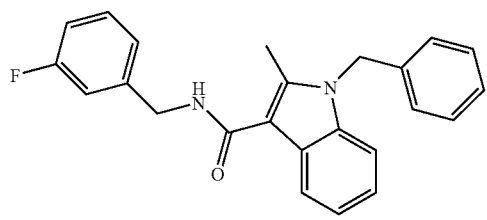 [SMILES: Cc1c(C(=O)NCc2cccc(F)c2)c2ccccc2n1Cc1ccccc1] |
| 38 | 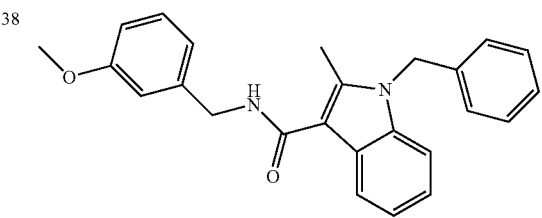 |
| 39 | 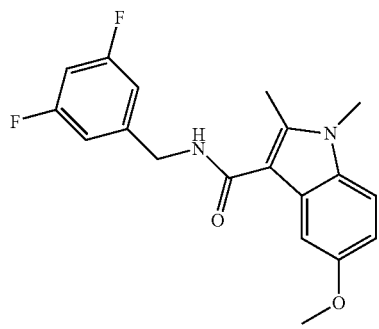 [SMILES: COc1ccc2c(c1)c(C(=O)NCc1cc(F)cc(F)c1)c(C)n2C] |
| 40 | 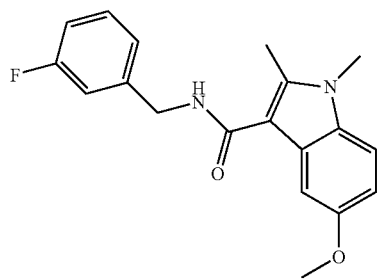 [SMILES: COc1ccc2c(c1)c(C(=O)NCc1cccc(F)c1)c(C)n2C] |
| NO. | COMPOUND |
|---|---|
| 41 | 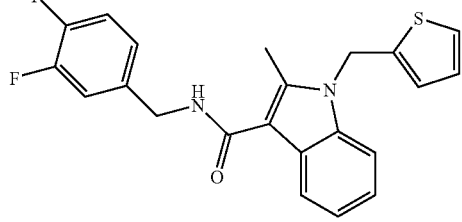 |
| 42 | 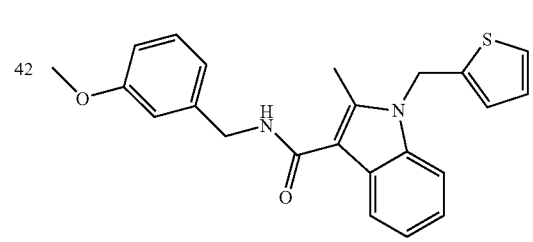 |
| 43 | 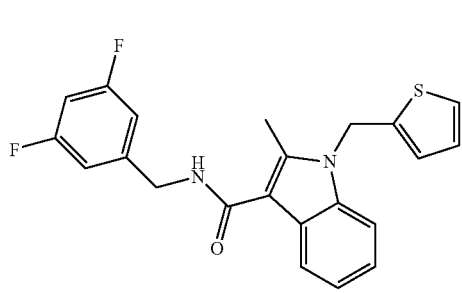 [SMILES: Cc1c(C(=O)NCc2cc(F)cc(F)c2)c2ccccc2n1Cc1cccs1] |
| 44 |  |
| 45 |  |

-continued

| NO. | COMPOUND |
|---|---|
| 46 | 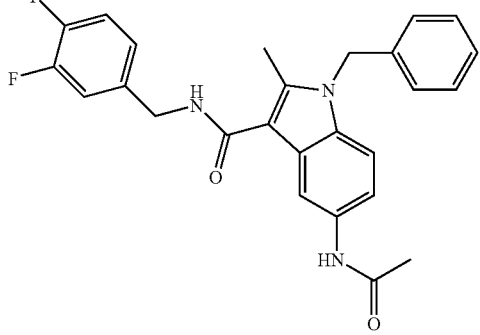 |
| 47 | 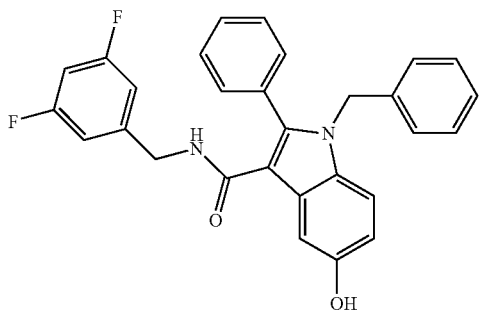 [SMILES: O=C(NCc1cc(F)cc(F)c1)c1c(-c2ccccc2)n(Cc2ccccc2)c2ccc(O)cc12] |
| 48 | 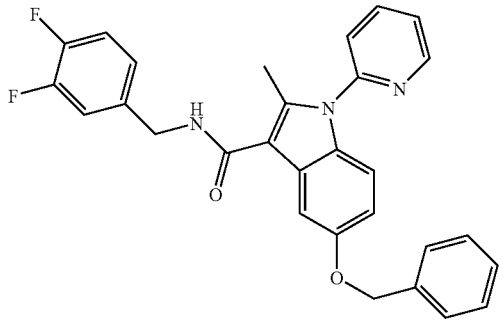 [SMILES: Cc1c(C(=O)NCc2ccc(F)c(F)c2)c2cc(OCc3ccccc3)ccc2n1-c1ccccn1] |

Additional Indole Compounds

U.S. Patent Application No. 60/884,470 discloses S1P3 receptor antagonists having the following formula:

Formula I

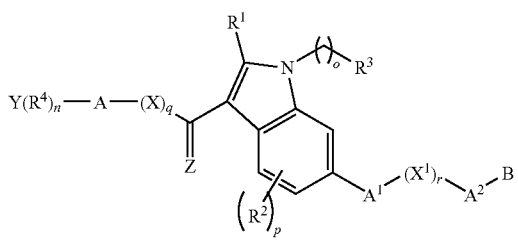

wherein:

$R^1 R^2$, $R^3$ and $R^4$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, carbocyclic hydrocarbon groups having from 3 to 20 carbon atoms, heterocyclic groups having up to 20 carbon atoms and at least one of oxygen, nitrogen and/or sulfur in the ring, halo, $C_1$ to $C_{12}$ haloalkyl, hydroxyl, $C_1$ to $C_{12}$ alkoxy, $C_3$ to $C_{20}$ arylalkyloxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, and sulfonyl groups;

X and $X^1$ are independently selected from the group consisting of $NR^5$, O and S;

$R^5$ is hydrogen, an alkyl group of 1 to 10 carbons, a cycloalkyl group of 5 to 10 carbons, phenyl or lower alkylphenyl;

Y is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;

Z is O or S;

n is 0 or an integer of from 1 to 5;

o is 0 or an integer of from 1 to 3;

p is 0 or an integer of from 1 to 3;

q is 0 or 1;

r is 0 or 1;

A, $A^1$ and $A^2$ are independently selected from the group consisting of $(CH_2)_v$ wherein v is 0 or an integer of from 1 to 12, branched chain alkyl having 3 to 12 carbons, cycloalkyl having 3 to 12 carbons, alkenyl having 2 to 10 carbons and 1-3 double bonds and alkynyl having 2 to 10 carbons and 1 to 3 triple bonds;

B is selected from the group consisting of hydrogen, $OR^6$, $COOR^7$, $NR^8R^9$, $CONR^8R^9$, $COR^{10}$, $CH=NOR^{11}$, $CH=NNR^{12}R^{13}$ wherein $R^6$, $R^7$, $R^{10}$ and $R^{11}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, $R^8$, $R^9$, $R^{12}$ and $R^{13}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, or $R^8$ and $R^9$ and/or $R^{12}$ and $R^{13}$, together, can form a divalent carbon radical of 2 to 5 carbons to form a heterocyclic ring with nitrogen, wherein any of $R^6$, $R^7$, $R^8$, $R^9$, $R^{10}$, $R^{11}$, $R^{12}$ or $R^{13}$ (may be substituted with one or more halogen, hydroxy, alkyloxy, cyano, nitro, mercapto or thiol radical; provided however, when v is 0, and r is 0, B is not hydrogen; or B is a carbocyclic hydrocarbon group having from 3 to 20 carbon atoms, or a heterocyclic group having up to 20 carbon atoms and at least one of oxygen, nitrogen and/or sulfur in the ring, and wherein when said B is a carbocyclic or heterocyclic group B may be bonded to $A^2$ at any position, or a pharmaceutically acceptable salt of said compound.

The aryl group is a carbocyclic aryl or heterocyclic aryl group wherein said carbocyclic aryl comprises from 6 to 20 atoms and said heterocyclic aryl comprise from 2 to 20 carbon atoms and from 1 to 5 heteroatoms selected from the group consisting of nitrogen, oxygen and sulfur, and preferably said aryl group is selected from the group consisting of benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone. Said aryl groups can be bonded to the above moiety at any position. Said aryl group may itself be substituted with any common organic functional group including but not limited to $C_1$ to $C_{12}$ alkyl, $C_2$ to $C_6$ alkenyl, $C_2$ to $C_6$ alkynyl, halo, $C_1$ to $C_{12}$ haloalkyl, hydroxyl, $C_1$ to $C_{12}$ alkoxyl, $C_1$ to $C_{12}$ alkylcarbonyl, formyl, oxycarbonyl, carboxyl, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups.

Preferably Z is O.

Preferably, the carbocyclic aryl group will comprise from 6 to 14 carbon atoms, e.g. from 6 to 10 carbon atoms. Preferably the heterocyclic aryl group will comprise from 2 to 14 carbon atoms and one or more, e.g. from 1 to 3 heteroatoms selected from the group consisting of nitrogen, oxygen and sulfur.

Preferably, A is $CH_2$.

Preferably, X is NH.

Preferably, n is 0 or an integer of 1 or 2 and $R^4$ is fluoro.

Preferably, $R^1$ is i-propyl.

Preferably, $R^3$ is selected from the group consisting of phenyl, which may be substituted with one or two fluoro groups, and pyridyl.

Preferably, p is 0.

Preferably, $A^1$ and $A^2$ are absent.

Preferably, B is $OR^6$ or $COOR^7$.

Preferably, X is O, r is 1, $A^1$ is absent, $A^2$ is $(CH_2)_v$, wherein v is 1 or 2, and B is $OR^6$ or $NR^8R^9$, and $R^6$, $R^8$ and $R^9$ are methyl.

Preferably, B is $CR^{10}=NOR^{11}R^{10}$ wherein $R^{10}$ is H and $R^{11}$ is methyl or i-butyl or B is $CONR^8R^9$ wherein $R^8$ and $R^9$ are selected from the group consisting of H, methyl, ethyl and propyl, or $R^8$ and $R^9$, together with N, form a 5-member ring.

Preferably, $A^1$ is absent, r is 0, $A^2$ is $CH_2$ and B is $OR^6$, wherein $R^6$ is H, or X is O, r is 1 and B is $COR^{10}$, wherein $R^{10}$ is methyl.

Examples of such compounds include the following:

| No. | Compound |
|-----|----------|
| 49  | 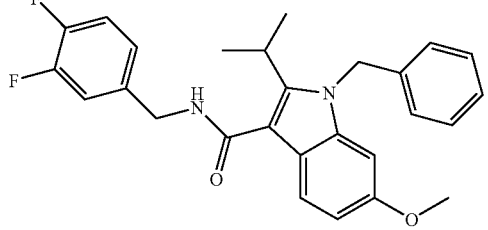 |
| 50  | 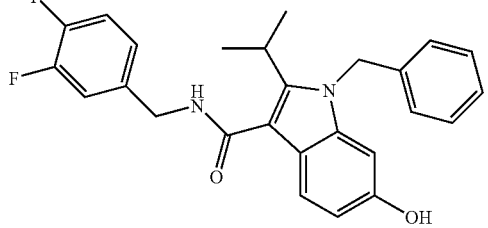 |
| 51  | 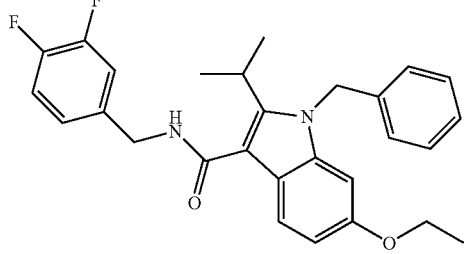 |
| 52  | 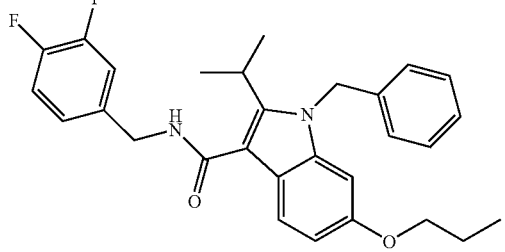 |

-continued
| No. | Compound |
|---|---|
| 53 | 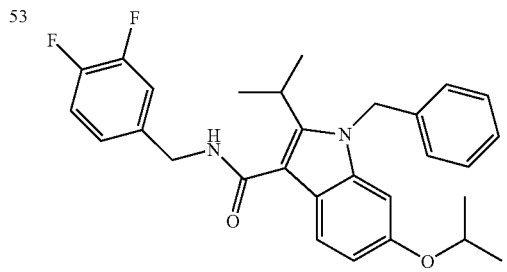 |
| 54 | 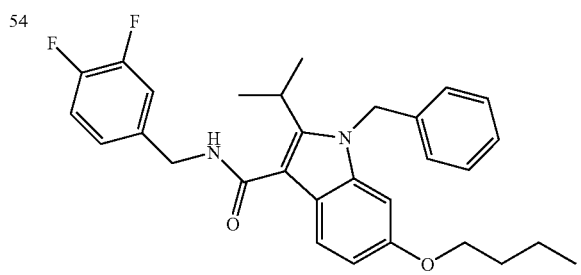 |
| 55 | 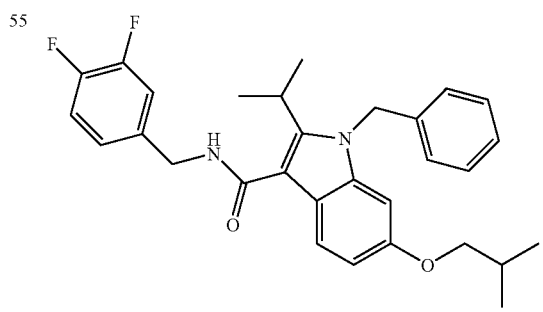 |
| 56 | 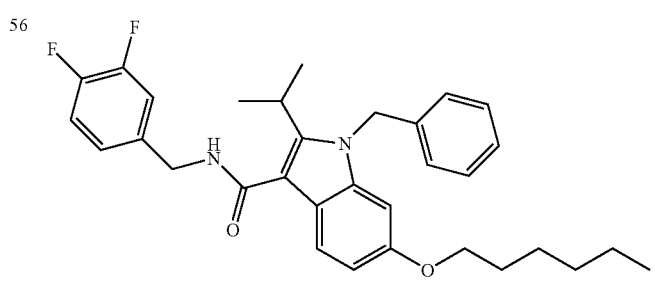 |
| 57 | 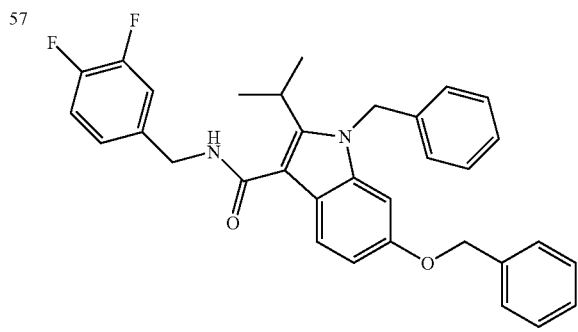 |

-continued
| No. | Compound |
|---|---|
| 58 | 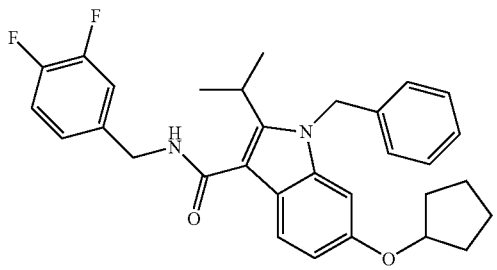 |
| 59 | 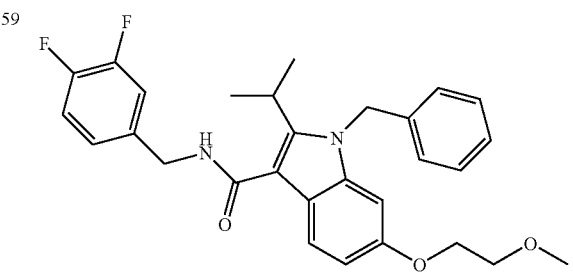 |
| 60 | 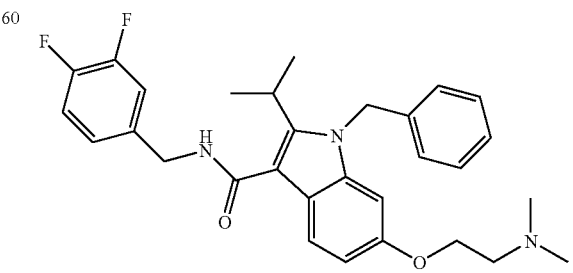 |
| 61 | 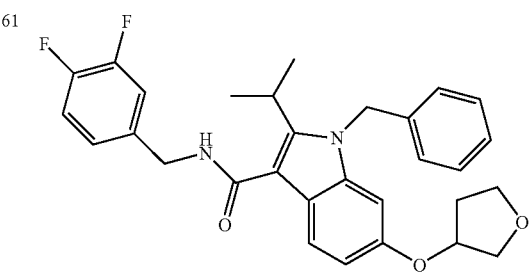 |
| 62 | 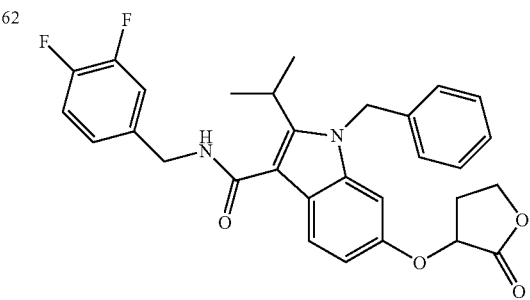 |

| No. | Compound |
|---|---|
| 63 | 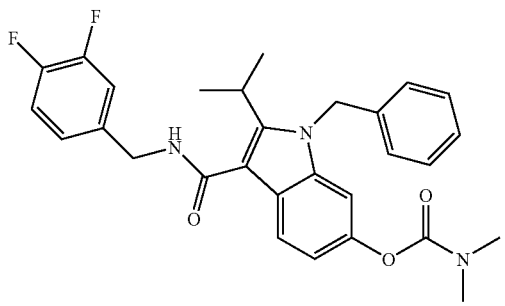 |
| 64 | 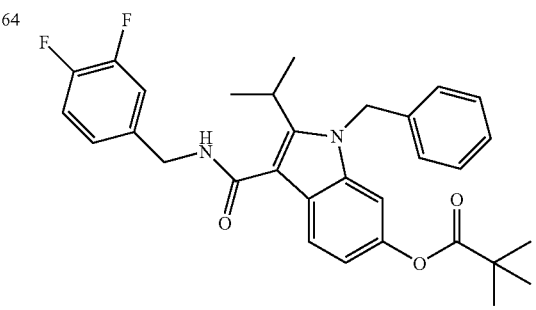 |
| 65 | 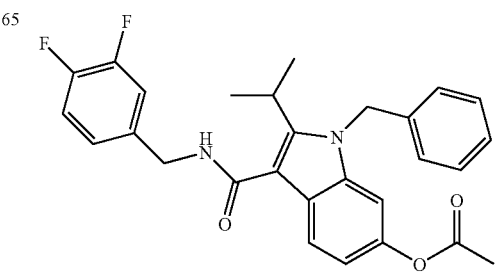 |
| 66 | 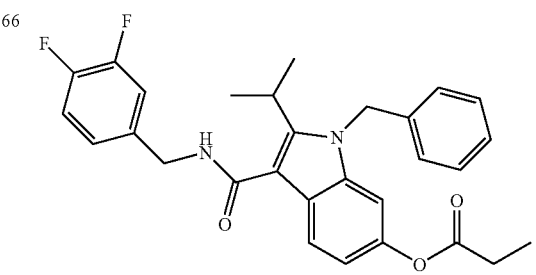 |
| 67 | 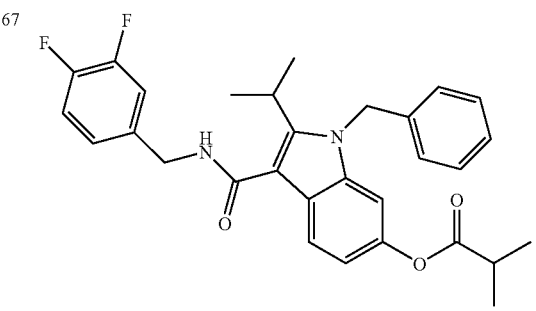 |

| No. | Compound |
|---|---|
| 68 | 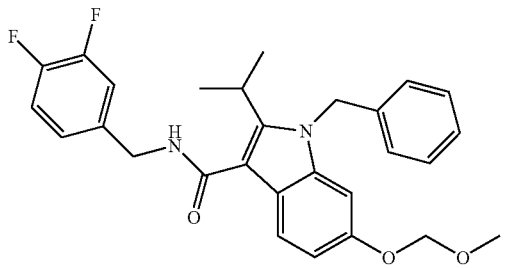 |
| 69 | 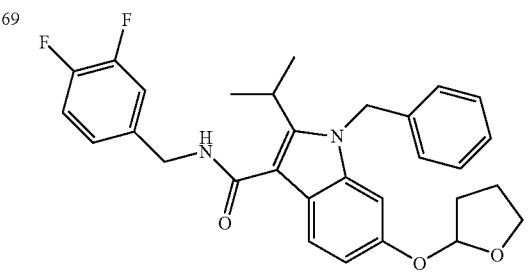 |
| 70 | 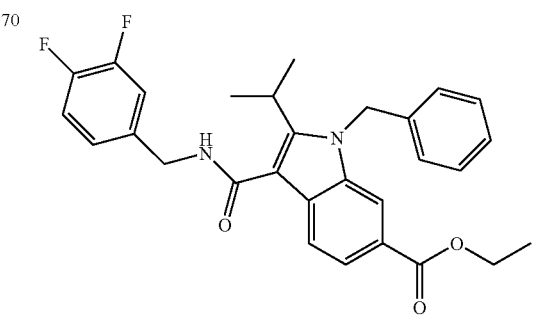 |
| 71 | 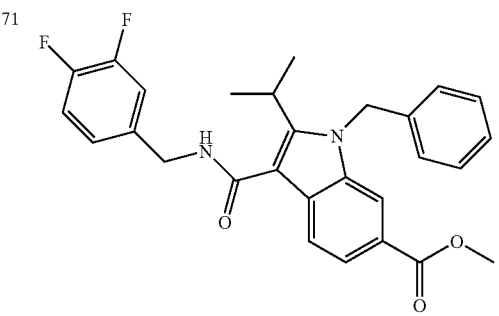 |
| 72 | 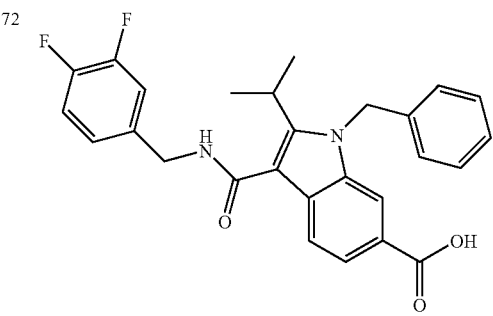 |

-continued
| No. | Compound |
|---|---|
| 73 | 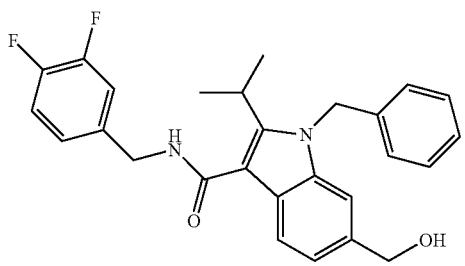 |
| 74 | 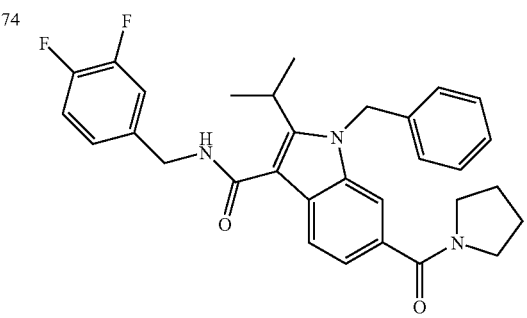 |
| 75 | 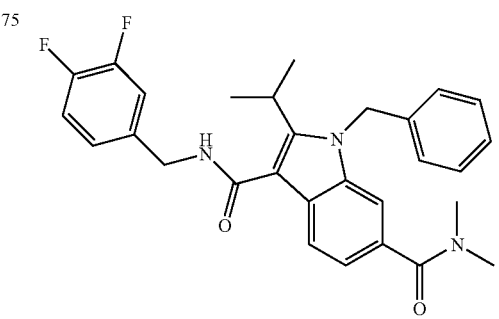 |
| 76 | 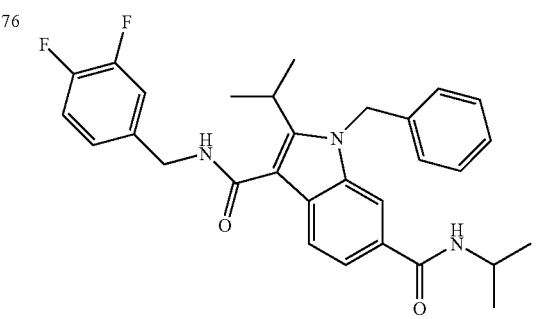 |
| 77 | 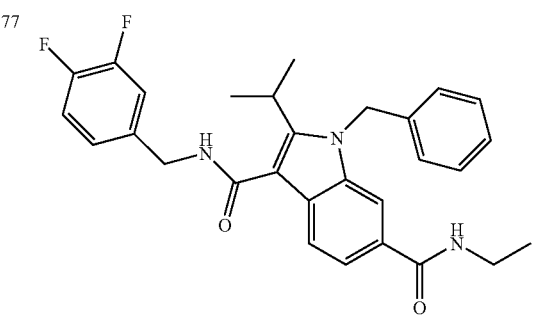 |

| No. | Compound |
|---|---|
| 78 | 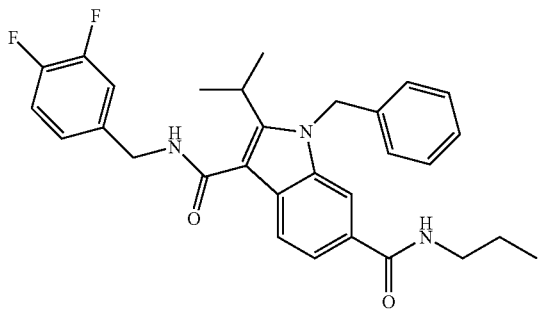 |
| 79 | 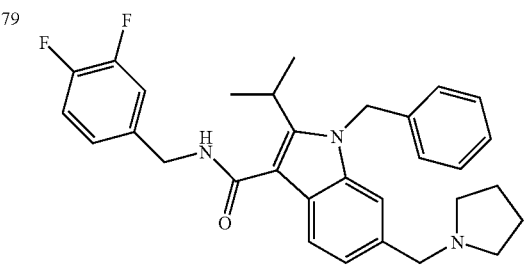 |
| 80 | 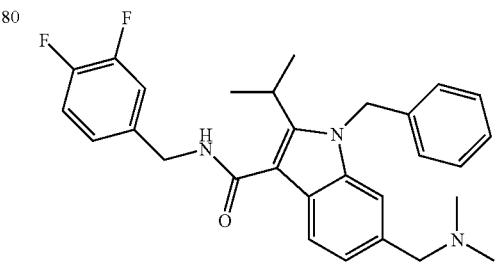 |
| 81 | 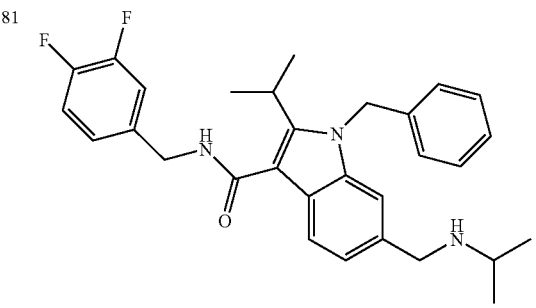 |
| 82 | 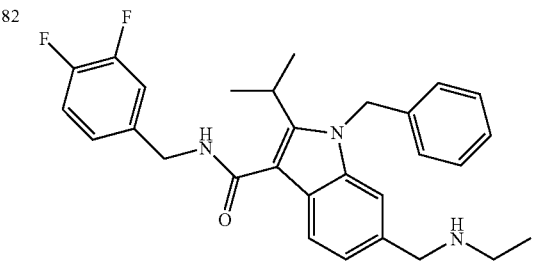 |

-continued
| No. | Compound |
|---|---|
| 83 | 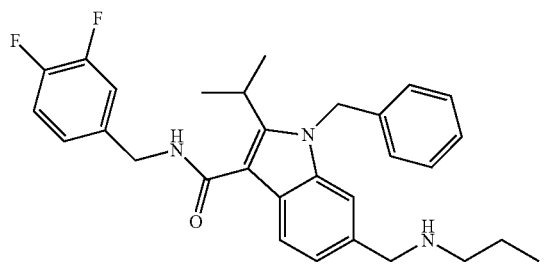 |
| 84 | 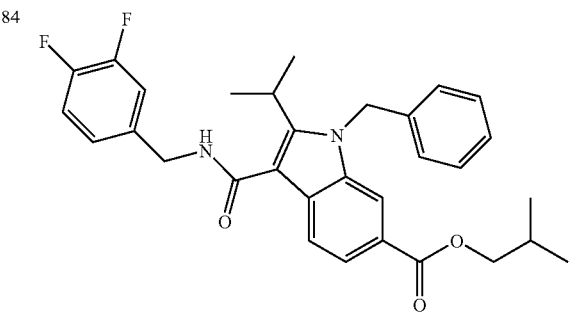 |
| 85 | 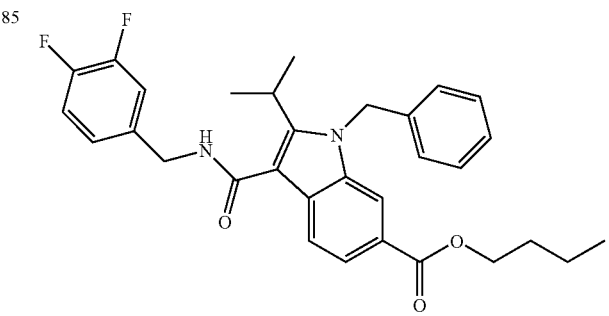 |
| 86 | 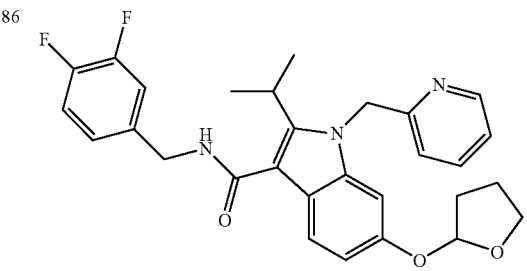 |
| 87 | 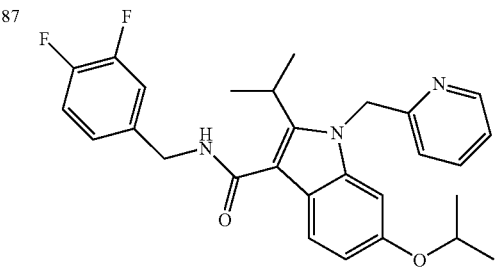 |

-continued
| No. | Compound |
|---|---|
| 88 | 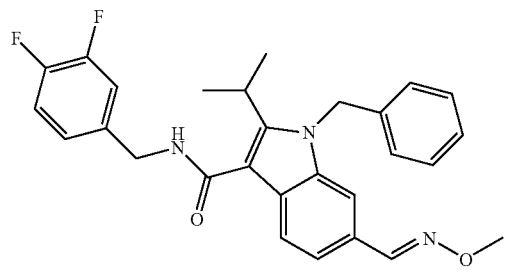 |
| 89 | 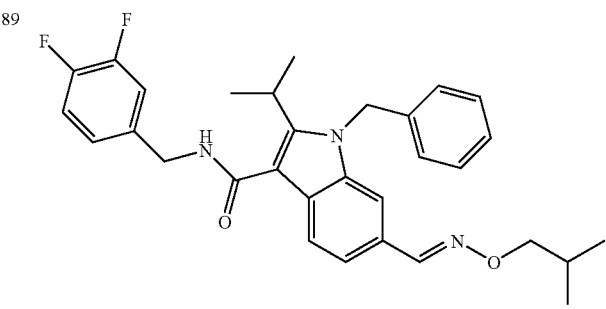 |
| 90 | 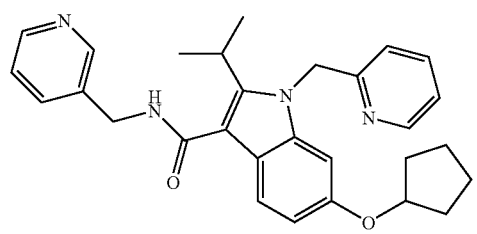 |
| 91 | 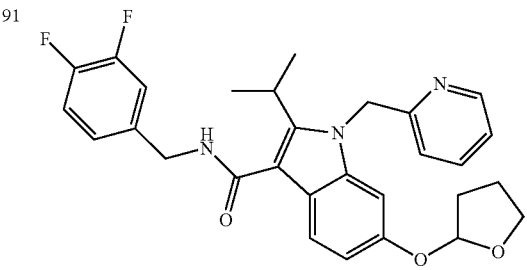 |
| 92 | 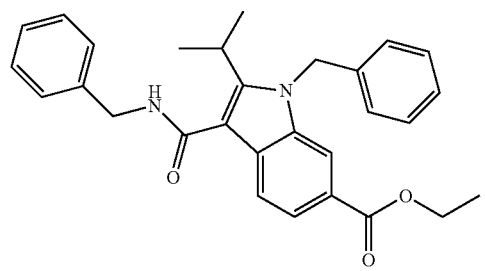 |

| No. | Compound |
|-----|----------|
| 93 | 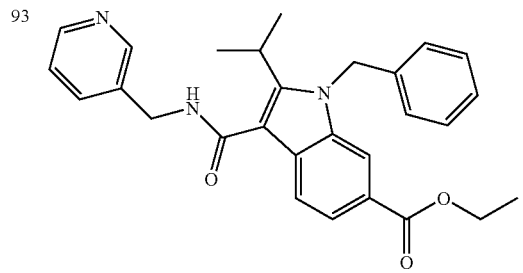 |
| 94 | 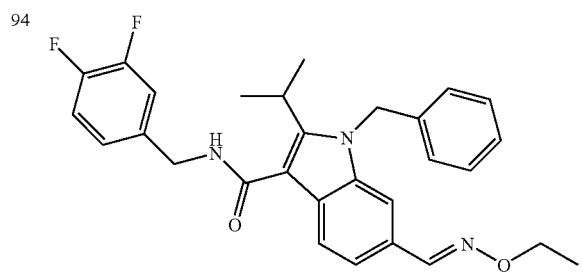 |
| 95 | 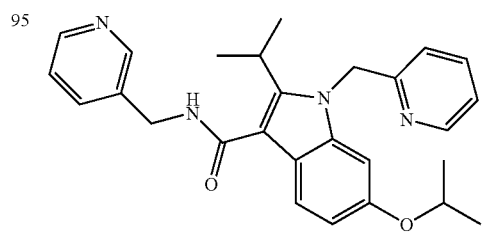 |
| 96 | 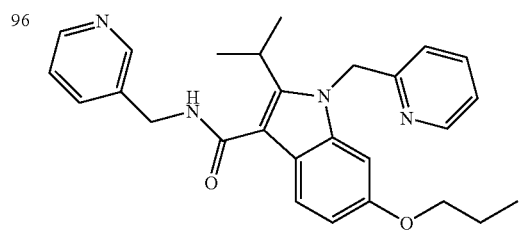 |
| 97 | 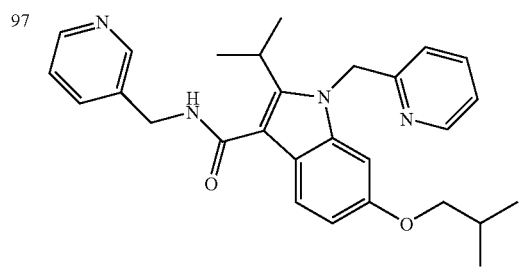 |
| 98 | 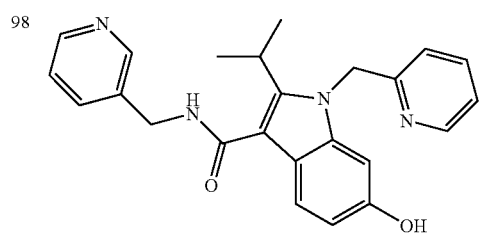 |

| No. | Compound |
|---|---|
| 99 | 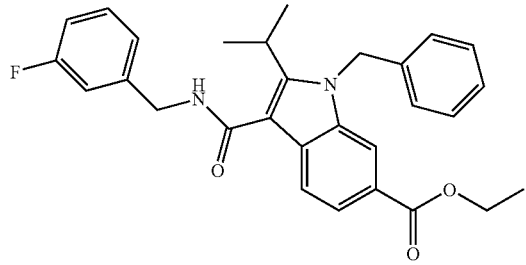 |
| 100 | 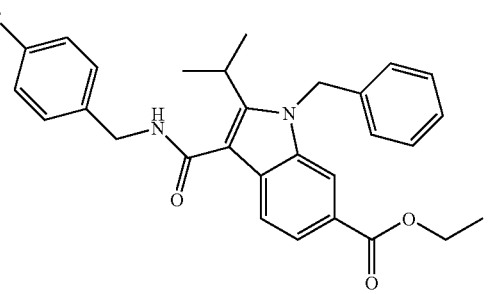 |
| 101 | 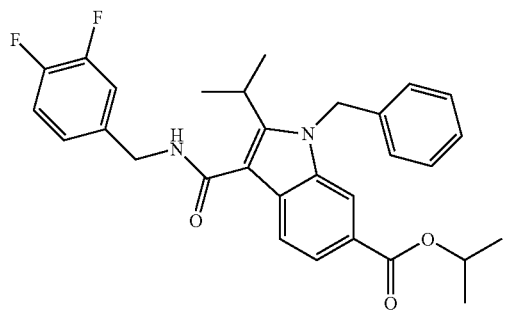 |
| 102 | 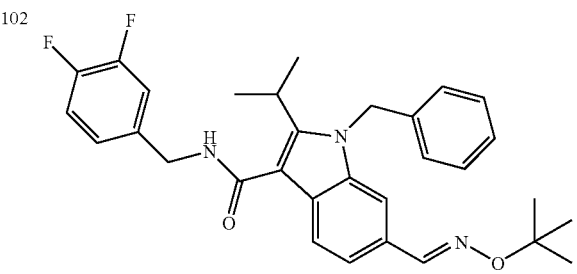 |
| 103 | 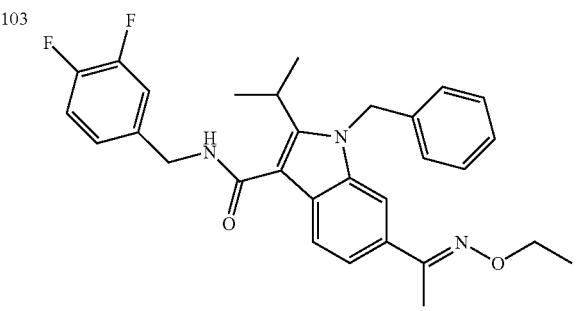 |

-continued
| No. | Compound |
|---|---|
| 104 | 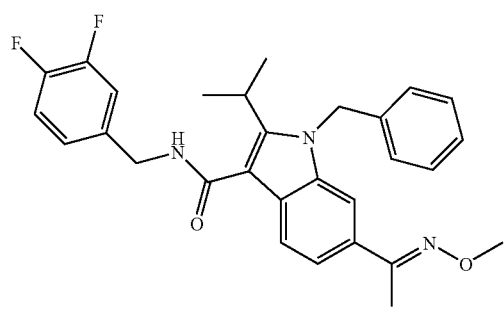 |
| 105 | 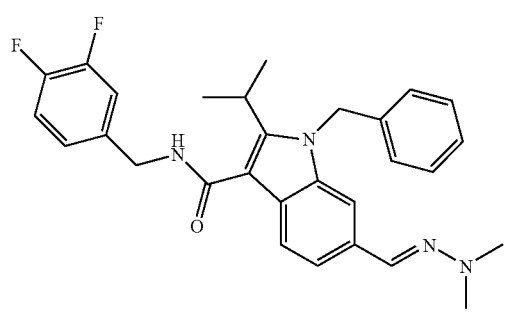 |
| 106 | 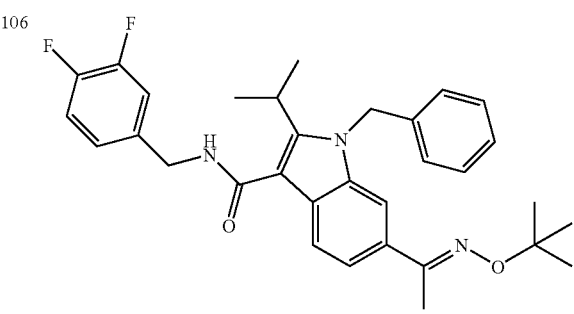 |
| 107 | 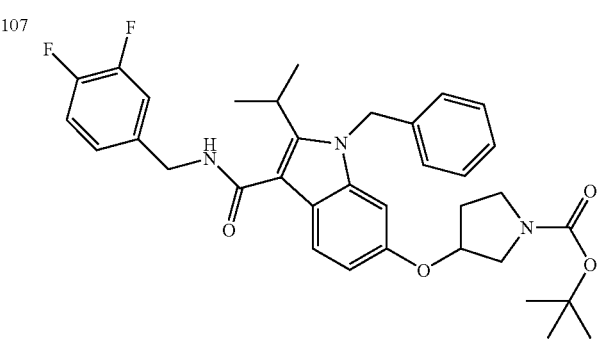 |
| 108 | 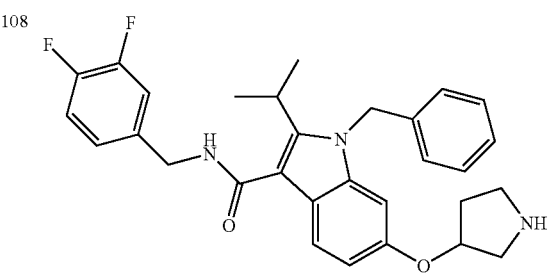 |

-continued
| No. | Compound |
|---|---|
| 109 | 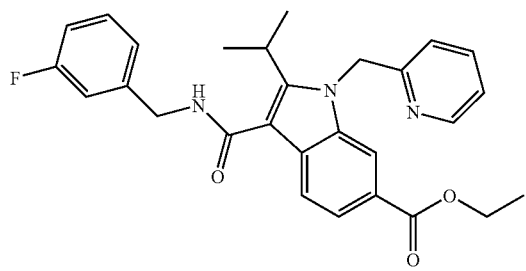 |
| 110 | 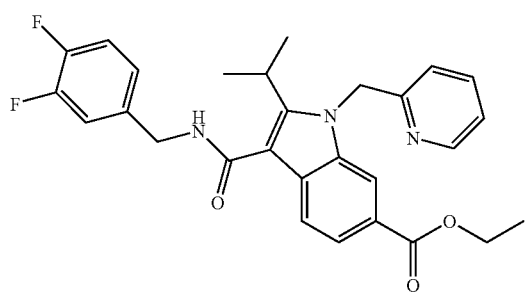 |
| 111 | 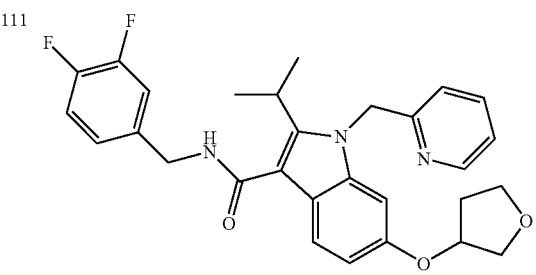 |
| 112 | 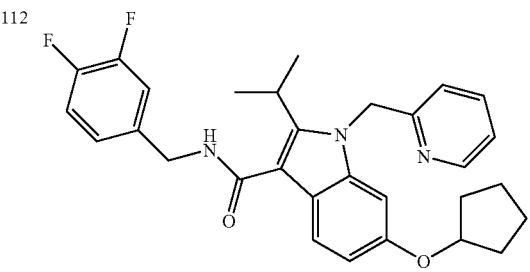 |
| 113 | 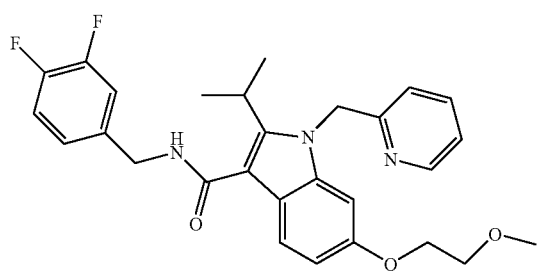 |

| No. | Compound |
|---|---|
| 114 | 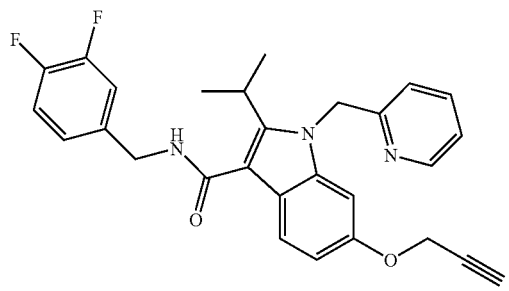 |
| 115 | 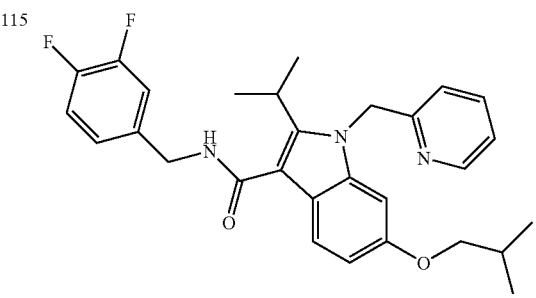 |
| 116 | 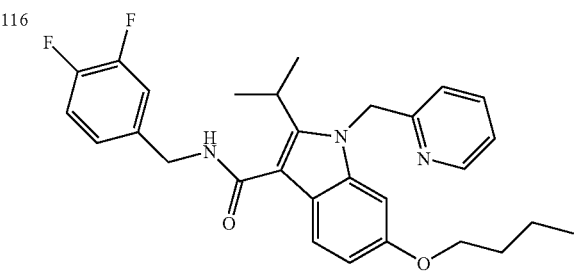 |
| 117 | 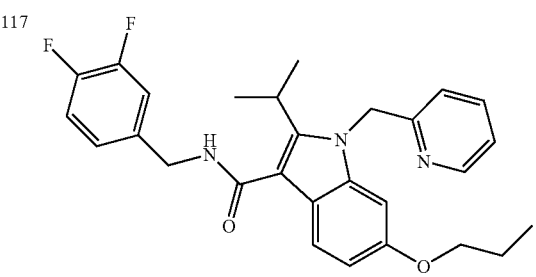 |
| 118 | 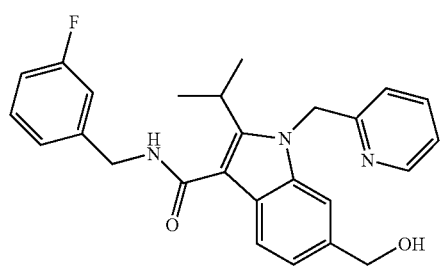 |

| No. | Compound |
|---|---|
| 119 | 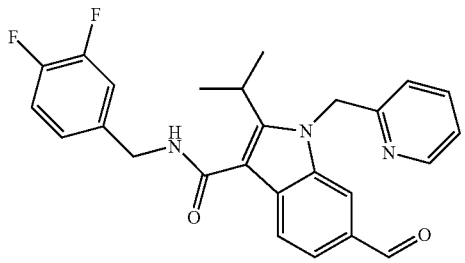 |
| 120 | 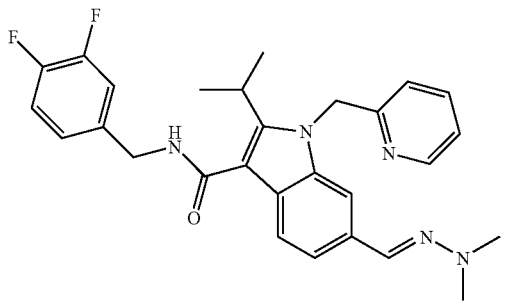 |
| 121 | 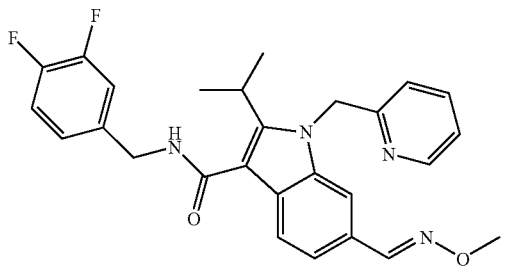 |

Other Indole compounds

Other compositions useful in the methods of the invention include those disclosed in U.S. patent application Ser. No. 11/690,637. That application discloses S1P3 receptor antagonists having the following formula:

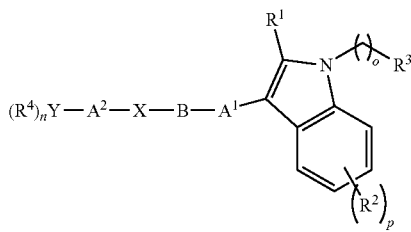

wherein:

$A^1$ and $A^2$ are independently selected from the group consisting of $(CH_2)m$ where m is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $NR^5$, O and S;

B is selected from the group consisting of $(CH_2)n$, where n is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $C=C$ $(R^5)_2$, $C=O$, $C=S$, $R^5C=NR^5$, $R^5C=CR^5$, $C=NOR^5$, $CR^5OR^5$, $C(OR^5)_2$, $CR^5N(R^5)_2$, $C(N(R^5)_2)_2$, $CR^5SR^5$, $C(SR^5)_2$, SO, $SO_2$, and heterocyclic aryl comprising from 2 to 14 carbon atoms and from 1 to 3 heteroatoms selected from the group consisting of nitrogen, oxygen and sulfur;

X is selected from the group consisting of $(CH_2)r$, where r is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $NR^5$, O and S;

provided that when m is 0 and B is $C=O$ then X is not $NR^5$, O or S;

Y is $R^6$, or a carbocyclic aryl group comprising from 6 to 14 carbon atoms or a heterocyclic aryl group comprising from 2 to 14 carbon atoms and from 1 to 3 heteroatoms selected from the group consisting of nitrogen, oxygen and sulfur;

o is 0 or an integer of from 1 to 3;

p is 0 or an integer of from 1 to 4;

$R^1$, $R^2$, $R^3$, $R^4$ are independently selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, halo, $C_1$ to $C_{12}$ haloalkyl, hydroxy, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, sulfonyl,

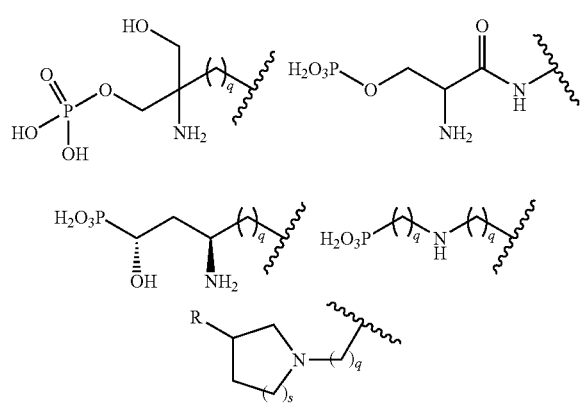

wherein R is CO₂H or PO₃H₂ and q is 0 or an integer of 1 to 5 and s is 0 or an integer from 1 to 3;

R⁵ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, halo, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl and sulfonyl; and R⁶ is selected from the group consisting of straight or branched chain alkyl having 1 to 12 carbons, cycloalkyl having 3 to 6 carbons, alkenyl having 2 to 6 carbons and 1 or 2 double bonds and alkynyl having 2 to 6 carbons and 1 or 2 triple bonds.

Examples of such compounds include the following.

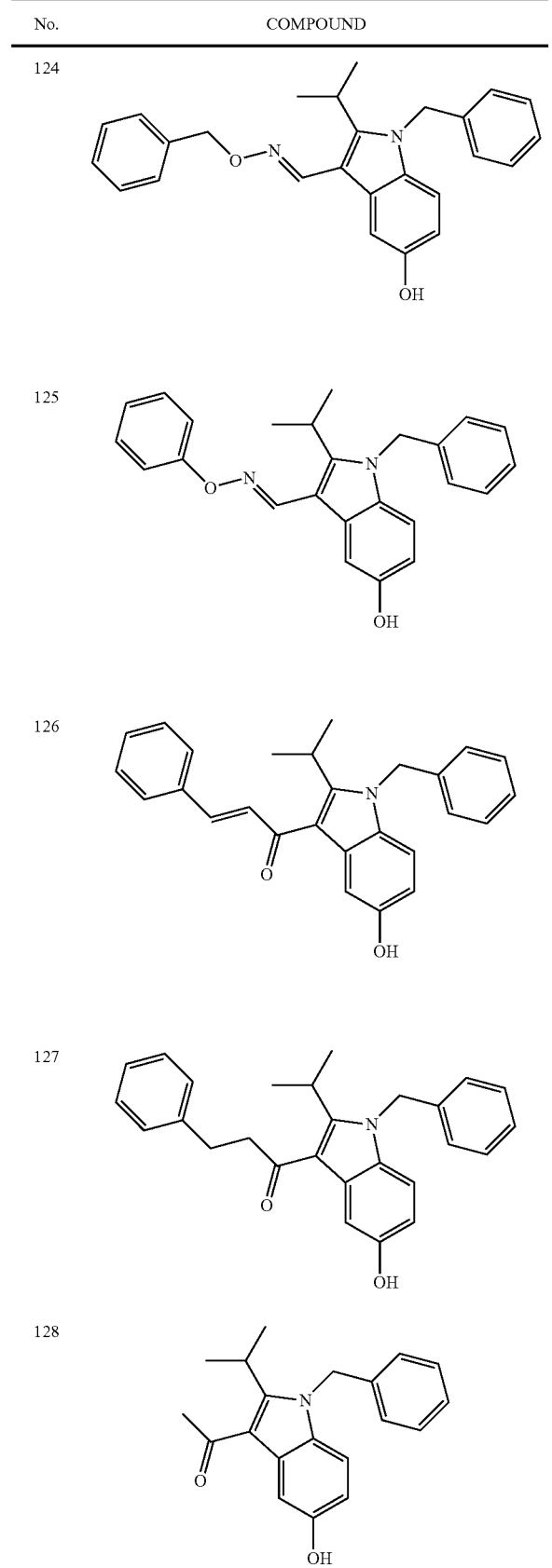

| No. | COMPOUND |
|---|---|
| 129 | 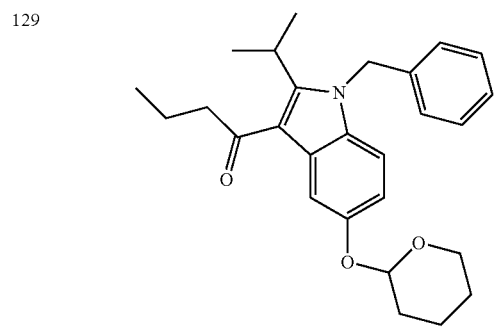 |
| 130 | 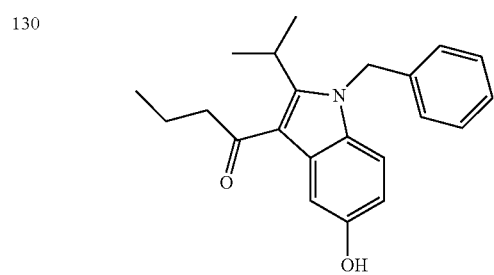 |
| 131 | 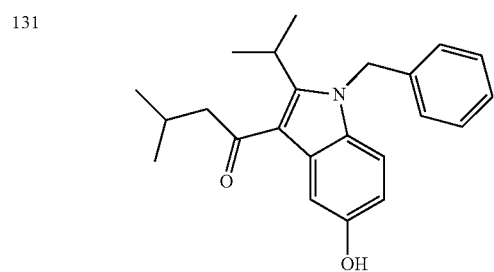 |
| 132 | 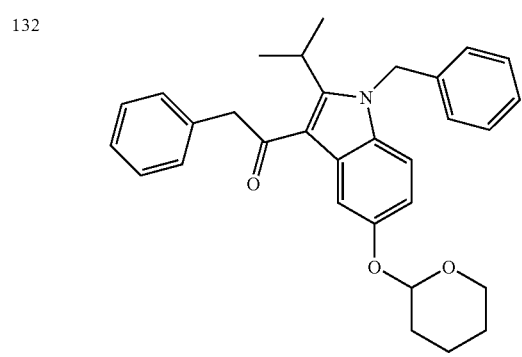 |
| 133 | 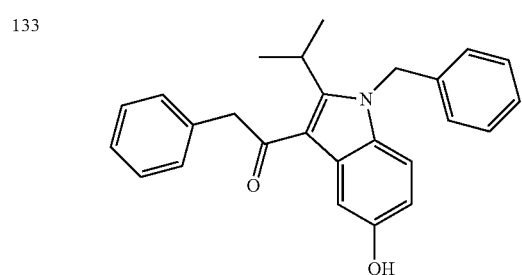 |
| No. | COMPOUND |
|---|---|
| 134 | 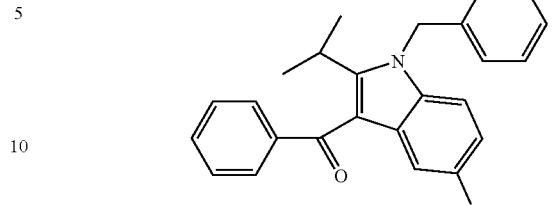 |
| 135 | 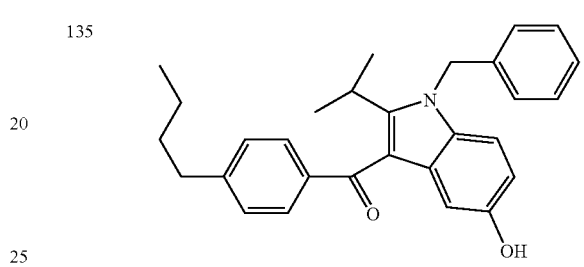 |
| 136 | 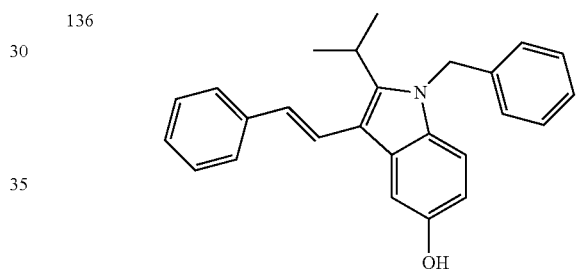 |
| 137 | 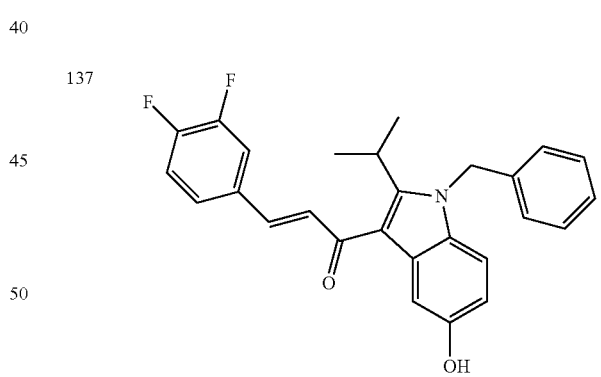 |
| 138 | 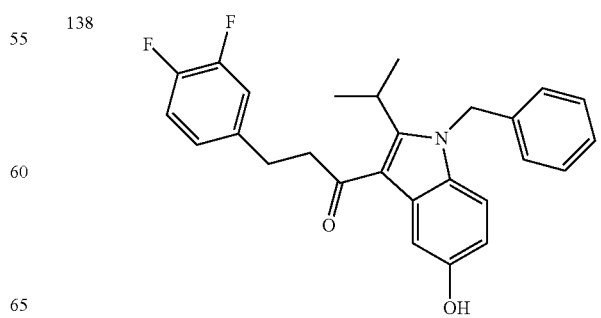 |

| No. | COMPOUND |
|---|---|
| 139 | 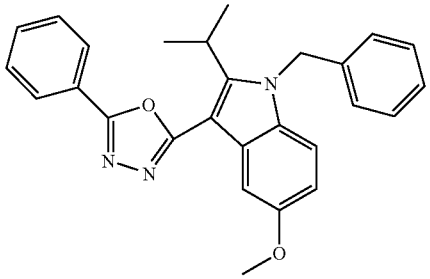 |
| 140 | 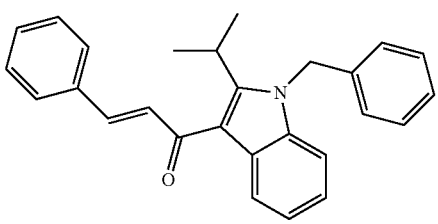 |
| 141 | 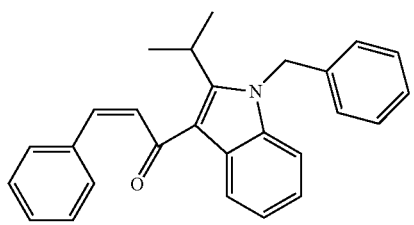 |
| 142 | 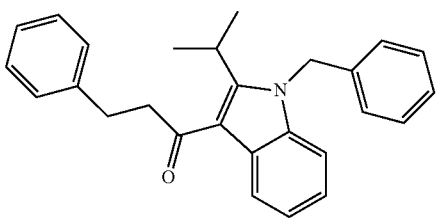 |
| 143 | 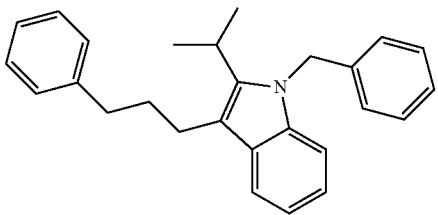 |
| 144 | 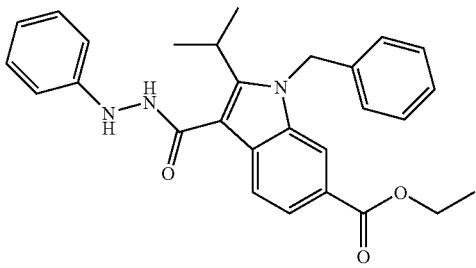 |

| No. | COMPOUND |
|---|---|
| 145 | 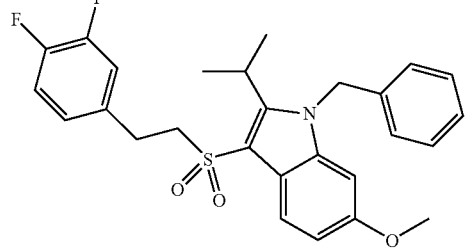 |

Heteroaromatic Compounds

Other compositions useful in the methods of the invention include those disclosed in U.S. Patent Application No. 60/824,807. That application discloses S1P3 receptor antagonists having the following formula:

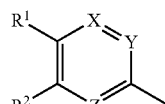

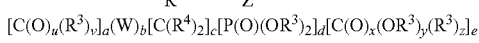

wherein
X is selected from the group consisting of $CR^3$ and N;
Y is selected from the group consisting of $CR^3$ and N;
Z is selected from the group consisting of $CR^3$ and N;
at least one of X, Y and Z is N;
W is $NR^3$ or O;
$R^1$ is an aryl group;
$R^2$ is an aryl group;
$R^3$ is selected from the group consisting of H and alkyl; and 2 of said $R^3$ groups may together with N may form a heterocyclic ring having from 2 to 6 carbon atoms; $R^4$ is selected from the group consisting of H, alkyl, $OR^3$, and $N(R^3)_2$;
a is 0 or an integer of from 1 to 6;
b is 0 or 1;
c is 0 or an integer of from 1 to 6;
d is 0 or 1;
e is 0 or 1;
u is 0 or 1;
v is 0 or an integer of from 1 to 2;
x is 0 or 1;
y is 0 or an integer of from 1 to 3;
z is 0 or an integer of from 1 to 3;
provided, however, that when d is 0, e is 1, and when e is 0, d is 1.

Examples of such compounds include the following. Several of these selectively inhibit the S1P3 receptor subtype as compared to at least the S1P1 receptor subtypes. The $EC_{50}$ and $IC_{50}$ values expressed in the following table were obtained in the FLIPR assay described above. $EC_{50}$ or $IC_{50}$ values are stated first, followed by percent efficacy or percent inhibition stated in parenthesis. In this table and the next, percent efficacy is defined as percent of receptor activity induced by a test compound at the highest dose tested (10 μM) relative to the receptor activity induced by 5 nM sphingosine-1-phosphate, and percent inhibition is defined as percent of receptor activity induced by 5 nM sphingosine-1-phosphate that is inhibited by a test compound at the highest dose tested (10 μM). "NA" means that no activity was detected at highest dose tested; "ND" means not determined.

| No. | COMPOUND | S1P1 (EC50) | S1P3 (IC50) |
|---|---|---|---|
| 146 | | ND | 1.6 μM (83) |
| 147 | | 121 nM (36) | 231 nM (98) |
| 148 | | 170 nM (57) | 319 nM (98) |
| 149 | | NA | 1.8 μM (99) |
| 150 | | ND | ND (95) |
| 151 | | NA | 1.1 μM (95) |

-continued

| No. | COMPOUND | S1P1 (EC50) | S1P3 (IC50) |
|---|---|---|---|
| 152 | | NA | 1.8 μM (68) |
| 153 | | NA | ND (30) |
| 154 | | 114 nM (69) | 319 nM (98) |
| 155 | | NA | 4.0 μM (27) |
| 156 | | NA | 1.9 μM (11) |

| No. | COMPOUND | S1P1 (EC50) | S1P3 (IC50) |
|---|---|---|---|
| 157 | 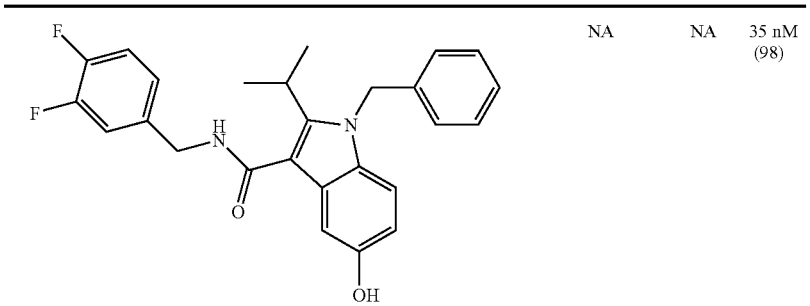 | NA | ND |

Additional Selective S1P3 Receptor Inhibitors

Examples of compounds that selectively inhibit the S1P3 receptor subtype as compared to at least the S1P1 and S1P2 receptor subtypes include the following. The $IC_{50}$ values expressed below were obtained in the FLIPR assay described above. $IC_{50}$ values are stated first (except as otherwise noted), followed by percent efficacy or percent inhibition in parenthesis.

| STRUCTURE | S1P1 ($IC_{50}$) | S1P2 ($IC_{50}$) | S1P3 ($IC_{50}$) |
|---|---|---|---|
|  | NA | NA | 35 nM (98) |
| 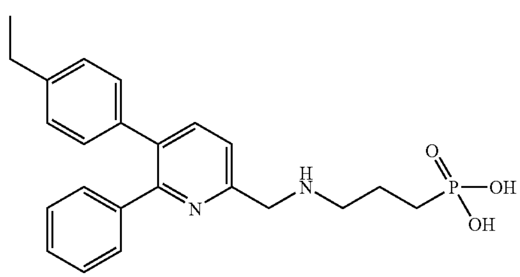 | $EC_{50}$ = 170 nM (57) | NA | 319 nM (98) |
| 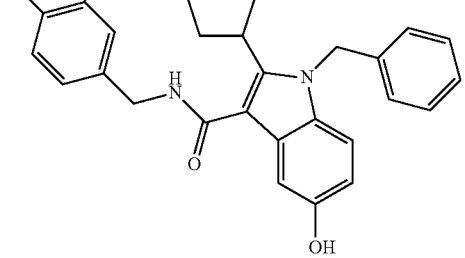 | NA | NA | 31 nM (100) |

| STRUCTURE | S1P1 (IC$_{50}$) | S1P2 (IC$_{50}$) | S1P3 (IC$_{50}$) |
|---|---|---|---|
| | NA | NA | 209 nM (100) |
| | NA | NA | 19 nM (100) |
| | NA | NA | 5 nM (100) |
| | NA | NA | 6 nM (100) |
| | NA | NA | 17 nM (99) |

S1P3 Inverse Agonists

U.S. Patent Publication No. 2005/022422 discloses S13P receptor inhibitors that are inverse agonists of S1P3. The inhibitors have the following formula

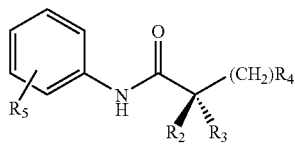

wherein $R_2$ is H, $R_3$ is $NH_2$, $R_4$ is phosphate, and $R_5$ is $(CH_2)_7 CH_3$, wherein $R_5$ may be in the ortho or meta position.

Pharmaceutically Acceptable Salts

One can use in the compositions and methods of the invention any S13P receptor inhibitor as its pharmaceutically acceptable salt.

A "pharmaceutically acceptable salt" is any salt which retains the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Prodrugs

One can use in the compositions and methods of the invention a prodrug of any pain-relieving anticonvulsant.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e., the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

The S13P receptor inhibitors of the invention may be either synthetically produced, or may be produced within the body after administration of a prodrug. Hence, "S13P receptor inhibitor" encompasses compounds produced by a manufacturing process and those compounds formed in vivo only when another drug administered.

Isomers and Racemates

One can use in the compositions and methods of the invention an enantiomer, stereoisomer, or other isomer of any S13P receptor inhibitor.

Pain

Pain, in general, may be divided into two types: chronic and acute. Acute pain has a relatively short duration and sudden onset. One type of acute pain, for example, is cutaneous pain felt on injury to the skin or other superficial tissues, such as caused by a cut or a burn. Cutaneous nociceptors terminate just below the skin, and due to the high concentration of nerve endings, produce a well-defined, localized pain of short duration.

Chronic pain is a pain other than an acute pain. There are various types of chronic pain, but those types of pain most amenable to treatment with the methods of the invention include neuropathic pain, inflammatory pain, somatic pain, visceral pain, and referred pain.

I. Neuropathic Pain

The methods of the invention may be used to treat pain caused by or otherwise associated with any of the following neuropathic pain conditions.

"Neuropathic pain" means abnormal sensory input, resulting from injury or malfunction of the peripheral nervous system, central nervous system, or both, that produces pain.

A. Symptoms of Neuropathic Pain

Symptoms of neuropathic pain can involve persistent, spontaneous pain, as well as allodynia, hyperalgesia, or hyperpathia.

B. Causes of Neuropathic Pain

Neuropathic pain may be caused by any of the following.

1. A traumatic insult, such as, for example, a nerve compression injury (e.g., a nerve crush, a nerve stretch, a nerve entrapment or an incomplete nerve transsection); a spinal cord injury (e.g., a hemisection of the spinal cord); a limb amputation; a contusion; an inflammation (e.g., an inflammation of the spinal cord); or a surgical procedure.

2. An ischemic event, including, for example, a stroke or heart attack.

3. An infectious agent

4. Exposure to a toxin, including, for example, a drug, an alcohol, a heavy metal (e.g., lead, arsenic, mercury), an industrial agent (e.g., a solvent, fumes from a glue) or nitrous oxide.

5. A disease, including, for example, an inflammatory disorder, a neoplastic tumor, an acquired immune deficiency syndrome (AIDS), Lymes disease, a leprosy, a metabolic disease, a neurodegenerative disease, a spinal stenosis, a mononeuropathy, a polyneuropathy, and a peripheral nerve disorder, such as a neuroma.

C. Types of Neuropathic Pain

1. Neuralgia

Neuralgia results in pain that radiates along the course of one or more cranial nerves, usually without any demonstrable pathological change in nerve structure.

Neuralgia includes, for example, trigeminal neuralgia, post-herpetic neuralgia, glossopharyngeal neuralgia, pain associated with nerve entrapment disorders, sciatica and atypical facial pain.

The affected nerves are responsible for sensing touch, temperature and pressure in the facial area from the jaw to the forehead. The disorder generally causes short episodes of excruciating pain, usually for less than two minutes and on only one side of the face. The pain can be described in a variety of ways such as "stabbing," "sharp," "like lightning," "burning," and even "itchy". In the atypical form of TN, the pain can also present as severe or merely aching and last for extended periods. The pain associated with TN is recognized as one the most excruciating pains that can be experienced.

The causes of neuralgia are varied. Chemical irritation, inflammation, trauma (including surgery), compression by nearby structures (for instance, by tumors), and infections may all lead to neuralgia. In many cases, however, the cause is unknown or unidentifiable. Neuralgia is most common in elderly persons, but it may occur at any age. Simple stimuli such as eating, talking, washing the face, or any light touch or sensation can trigger an attack (even the sensation of a gentle breeze). The attacks can occur in clusters or as an isolated attack.

Trigeminal neuralgia is the most common form of neuralgia. It affects the main sensory nerve of the face, the trigeminal nerve ("trigeminal" literally means "three origins", referring to the division of the nerve into 3 branches). This condition involves sudden and short attacks of severe pain on the side of the face, along the area supplied by the trigeminal nerve on that side. The pain attacks may be severe enough to cause a facial grimace, which is classically referred to as a painful tic (tic douloureux). Sometimes, the cause of trigeminal neuralgia is a blood vessel or small tumor pressing on the nerve. Disorders such as multiple sclerosis (an inflammatory disease affecting the brain and spinal cord), certain forms of arthritis, and diabetes (high blood sugar) may also cause trigeminal neuralgia, but a cause is not always identified. In this condition, certain movements such as chewing, talking, swallowing, or touching an area of the face may trigger a spasm of excruciating pain.

A related but rather uncommon neuralgia affects the glosso-pharyngeal nerve, which provides sensation to the throat. Symptoms of this neuralgia are short, shock-like episodes of pain located in the throat.

Neuralgia may occur after infections such as shingles, which is caused by the varicella-zoster virus, a type of herpesvirus. This neuralgia produces a constant burning pain after the shingles rash has healed. The pain is worsened by movement of or contact with the affected area. Not all of those diagnosed with shingles go on to experience postherpetic neuralgia, which can be more painful than shingles. The pain and sensitivity can last for months or even years. The pain is usually in the form of an intolerable sensitivity to any touch but especially light touch. Postherpetic neuralgia is not restricted to the face; it can occur anywhere on the body but usually occurs at the location of the shingles rash. Depression is not uncommon due to the pain and social isolation during the illness.

Postherpetic neuralgia may be debilitating long after signs of the original herpes infection have disappeared. Other infectious diseases that may cause neuralgia are syphilis and Lyme disease.

Diabetes is another common cause of neuralgia. This very common medical problem affects almost 1 out of every 20 Americans during adulthood. Diabetes damages the tiny arteries that supply circulation to the nerves, resulting in nerve fiber malfunction and sometimes nerve loss. Diabetes can produce almost any neuralgia, including trigeminal neuralgia, carpal tunnel syndrome (pain and numbness of the hand and wrist), and meralgia paresthetica (numbness and pain in the thigh due to damage to the lateral femoral cutaneous nerve). Strict control of blood sugar may prevent diabetic nerve damage and may accelerate recovery in patients who do develop neuralgia.

Other medical conditions that may be associated with neuralgias are chronic renal insufficiency and porphyria—a hereditary disease in which the body cannot rid itself of certain substances produced after the normal breakdown of blood in the body. Certain drugs may also cause this problem.

2. Deafferentation.

Deafferentation indicates a loss of the sensory input from a portion of the body, and can be caused by interruption of either peripheral sensory fibres or nerves from the central nervous system. A deafferentation pain syndrome, includes, without limitation, an injury to the brain or spinal cord, a post-stroke pain, a phantom pain, a paraplegia, a brachial plexus avulsion injuries, lumbar radiculopathies.

3. Complex Regional Pain Syndromes (CRPSs)

CRPS is a chronic pain syndrome with two forms. CRPS 1 currently replaces the term "reflex sympathetic dystrophy syndrome". It is a chronic nerve disorder that occurs most often in the arms or legs after a minor or major injury. CRPS 1 is associated with severe pain; changes in the nails, bone, and skin; and an increased sensitivity to touch in the affected limb. CRPS 2 replaces the term causalgia, and results from an identified injury to the nerve. A CRPS, includes, without limitation, a CRPS Type I (reflex sympathetic dystrophy) and a CRPS Type II (causalgia).

4. Neuropathy.

A neuropathy is a functional or pathological change in a nerve and is characterized clinically by sensory or motor neuron abnormalities.

Central neuropathy is a functional or pathological change in the central nervous system.

Peripheral neuropathy is a functional or pathological change in one or more peripheral nerves. The peripheral nerves relay information from your central nervous system (brain and spinal cord) to muscles and other organs and from your skin, joints, and other organs back to your brain. Peripheral neuropathy occurs when these nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Risk factors for neuropathy include diabetes, heavy alcohol use, and exposure to certain chemicals and drugs. Some people have a hereditary predisposition for neuropathy. Prolonged pressure on a nerve is another risk for developing a nerve injury. Pressure injury may be caused by prolonged immobility (such as a long surgical procedure or lengthy illness) or compression of a nerve by casts, splints, braces, crutches, or other devices. Polyneuropathy implies a widespread process that usually affects both sides of the body equally. The symptoms depend on which type of nerve is affected. The three main types of nerves are sensory, motor, and autonomic. Neuropathy can affect any one or a combination of all three types of nerves. Symptoms also depend on whether the condition affects the whole body or just one nerve (as from an injury). The cause of chronic inflammatory polyneuropathy is an abnormal immune response. The specific antigens, immune processes, and triggering factors are variable and in many cases are unknown. It may occur in association with other conditions such as HIV, inflammatory bowel disease, lupus erythematosis, chronic active hepatitis, and blood cell abnormalities.

Peripheral neuropathy may involve a function or pathological change to a single nerve or nerve group (monneuropathy) or a function or pathological change affecting multiple nerves (polyneuropathy). Table 1, below, lists some causes of peripheral neuropathies:

Some Causes of Peripheral Neuropathies

Hereditary Disorders
    Charcot-Marie-Tooth disease
    Friedreich's ataxia
Systemic or Metabolic Disorders
    Diabetes (diabetic neuropathy)
    Dietary deficiencies (especially vitamin B-12)
    Excessive alcohol use (alcoholic neuropathy)
    Uremia (from kidney failure)
    Cancer (including bone cancer and other cancers)
Infectious or Inflammatory Conditions
    AIDS
    Hepatitis
    Colorado tick fever
    Diphtheria
    Guillain-Barre syndrome
    HIV infection without development of AIDS
    Leprosy
    Lyme disease
    Polyarteritis nodosa
    Rheumatoid arthritis
    Sarcoidosis
    Sjogren's syndrome
    Syphilis
    Systemic Lupus erythematosus
    amyloid
Exposure to Toxic Compounds
    Sniffing glue or other toxic compounds
    Nitrous oxide
    Industrial agents—especially solvents
    Heavy metals (lead, arsenic, mercury, etc.)
    Neuropathy secondary to drugs like analgesic nephropathy
    Rhabdomyolysis
    Macrohagic myofasciitis
Highly Active Anti-Retrviral Therapy (HAART)-Induced neuropathy
Chemotherapy Induced Neuropathy
Miscellaneous Causes
    Ischemia (decreased oxygen/decreased blood flow)
    Prolonged exposure to cold temperature a. Polyneuropathy Polyneuropathy is a peripheral neuropathy involving the loss of movement or sensation to an area caused by damage or destruction to multiple peripheral nerves. Polyneuropathic pain, includes, without limitation, post-polio syndrome, post-mastectomy syndrome, diabetic neuropathy, alcohol neuropathy, amyloidosis, toxin exposure, AIDS, hypothyroidism, uremia, vitamin deficiencies, chemotherapy-induced pain, 2',3'-didexoycytidine (ddC) treatment, exposure to the anticonvulsant phenyloin, exposure to antibiotics including chloramphenicol, nitrofurantoin and sulfonamineds, exposure to sedatives including barbital and hexobarbital, Guillain-Barré syndrome, Fabry's disease or polyneuropathy secondary to cancers such as multiple myeloma.

b. Mononeuropathy

Mononeuropathy is a peripheral neuropathy involving loss of movement or sensation to an area caused by damage or destruction to a single peripheral nerve or nerve group. Mononeuropathy is most often caused by damage to a local area resulting from injury or trauma, although occasionally systemic disorders may cause isolated nerve damage (as with mononeuritis multiplex). The usual causes are direct trauma, prolonged pressure on the nerve, and compression of the nerve by swelling or injury to nearby body structures. The damage includes destruction of the myelin sheath (covering) of the nerve or of part of the nerve cell (the axon). This damage slows or prevents conduction of impulses through the nerve. Mononeuropathy may involve any part of the body. Mononeuropathic pain, includes, without limitation, a sciatic nerve dysfunction, a common peroneal nerve dysfunction, a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome, and a sixth (abducent) nerve palsy.

c. Generalized Peripheral Neuropathies

Generalized peripheral neuropathies are symmetrical, and usually due to various systematic illnesses and disease processes that affect the peripheral nervous system in its entirety. They are further subdivided into several categories:

i. Distal axonopathies are the result of some metabolic or toxic derangement of neurons. They may be caused by metabolic diseases such as diabetes, renal failure, deficiency syndromes such as malnutrition and alcoholism, or the effects of toxins or drugs. Distal axonopathy (aka dying back neuropathy) is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy.

ii. Myelinopathies are due to a primary attack on myelin causing an acute failure of impulse conduction. The most common cause is acute inflammatory demyelinating polyneuropathy (AIDP; aka Guillain-Barré syndrome), though other causes include chronic inflammatory demyelinating syndrome (CIDP), genetic metabolic disorders (e.g., leukodystrophy), or toxins. Myelinopathy is due to primary destruction of myelin or the myelinating Schwann cells, which leaves the axon intact, but causes an acute failure of impulse conduction. This demyelination slows down or completely blocks the conduction of electrical impulses through the nerve. The most common cause is acute inflammatory demyelinating polyneuropathy (AIDP, better known as Guillain-Barré syndrome), though other causes include chronic inflammatory demyelinating polyneuropathy (CIDP), genetic metabolic disorders (e.g., leukodystrophy or Charcot-Marie-Tooth disease), or toxins.

iii. Neuronopathies are the result of destruction of peripheral nervous system (PNS) neurons. They may be caused by motor neurone diseases, sensory neuronopathies (e.g., Herpes zoster), toxins or autonomic dysfunction. Neurotoxins may cause neuronopathies, such as the chemotherapy agent vincristine. Neuronopathy is dysfunction due to damage to neurons of the peripheral nervous system (PNS), resulting in a peripheral neuropathy. It may be caused by motor neurone diseases, sensory neuronopathies (e.g., Herpes zoster), toxic substances or autonomic dysfunction. A person with neuronopathy may present in different ways, depending on the cause, the way it affects the nerve cells, and the type of nerve cell that is most affected.

iv. Focal entrapment neuropathies (e.g., carpal tunnel syndrome) represent an additional category of generalized peripheral neuropathies.

II. Inflammatory Pain

The compositions and methods of the invention may be used to treat pain caused by or otherwise associated with any of the following inflammatory conditions.

A. Arthritic Disorder

Arthritic disorders include, for example, a rheumatoid arthritis; a juvenile rheumatoid arthritis; a systemic lupus erythematosus (SLE); a gouty arthritis; a scleroderma; an osteoarthritis; a psoriatic arthritis; an ankylosing spondylitis; a Reiter's syndrome (reactive arthritis); an adult Still's disease; an arthritis from a viral infection; an arthritis from a bacterial infection, such as, e.g., a gonococcal arthritis and a non-gonococcal bacterial arthritis (septic arthritis); a Tertiary Lyme disease; a tuberculous arthritis; and an arthritis from a fungal infection, such as, e,g, a blastomycosis B. Autoimmune Diseases Autoimmune diseases include, for example, a Guillain-Barré syndrome, a Hashimoto's thyroiditis, a pernicious anemia, an Addison's disease, a type I diabetes, a systemic lupus erythematosus, a dermatomyositis, Sjogren's syndrome, a lupus erythematosus, a multiple sclerosis, a myasthenia gravis, a Reiter's syndrome, a Grave's disease, and a rheumatoid arthritis.

C. Connective Tissue Disorder

Connective tissue disorders include, for example, a spondyloarthritis a dermatomyositis, and a fibromyalgia syndrome.

D. Injury

Inflammation caused by injury, including, for example, a crush, puncture, stretch of a tissue or joint, may cause chronic inflammatory pain.

E. Infection

Inflammation caused by infection, including, for example, a tuberculosis or an interstitial keratitis may cause chronic inflammatory pain. Infection may also result in inflammatory bowel diseases and irritable bowel syndromes.

F. Neuritis

Neuritis is an inflammatory process affecting a nerve or group of nerves. Symptoms depend on the nerves involved, but may include pain, paresthesias, paresis, or hypesthesia (numbness).

Examples include:

a. Brachial neuritis b. Retrobulbar neuropathy, an inflammatory process affecting the part of the optic nerve lying immediately behind the eyeball.

c. Optic neuropathy, an inflammatory process affecting the optic nerve causing sudden, reduced vision in the affected eye. The cause of optic neuritis is unknown. The sudden inflammation of the optic nerve (the nerve connecting the eye and the brain) leads to swelling and destruction of the myelin sheath. The inflammation may occasionally be the result of a viral infection, or it may be caused by autoimmune diseases such as multiple sclerosis. Risk factors are related to the possible causes.

d. Vestibular neuritis, a viral infection causing an inflammatory process affecting the vestibular nerve.

G. Joint Inflammation

Inflammation of the joint, such as that caused by bursitis or tendonitis, for example, may cause chronic inflammatory pain.

III. Headache Pain

The compositions and methods of the invention may be used to treat pain caused by or otherwise associated with chronic headache conditions. A headache (medically known as cephalgia) is a condition of mild to severe pain in the head; sometimes neck or upper back pain may also be interpreted as a headache. It may indicate an underlying local or systemic disease or be a disorder in itself.

IV. Somatic Pain

The compositions and methods of the invention may be used to treat pain caused by or otherwise associated with any of the following somatic pain conditions. Somatic pain originates from ligaments, tendons, bones, blood vessels, and even nerves themselves. It is detected with somatic nociceptors. The scarcity of pain receptors in these areas produces a dull, poorly-localized pain of longer duration than cutaneous pain; examples include sprains and broken bones. Additional examples include the following.

A. Excessive Muscle Tension

Excessive muscle tension can be caused, for example, by a sprain or a strain.

B. Repetitive Motion Disorders

Repetitive motion disorders can result from overuse of the hands, wrists, elbows, shoulders, neck, back, hips, knees, feet, legs, or ankles.

C. Muscle Disorders

Muscle disorders causing somatic pain include, for example, a polymyositis, a dermatomyositis, a lupus, a fibromyalgia, a polymyalgia rheumatica, a macrophagic myofasciitis, and a rhabdomyolysis. Muscle pain can also be secondary to neurological and neuromuscular disorders including without limitation Parkinson's disease, Huntington's chorea, dystonias, tardive dyskinesias, drug-induced dyskinesias and dystonias, dyskinesias (paroxysmal), amyotrophic lateral sclerosis, multiple sclerosis, myoclonus, progressive supranuclear palsy, corticobasal degeneration, choreoathetosis, spasticity, Wilson disease, multiple system atrophy (including Shy-Drager syndrome, striatonigral degeneration and olivopontocerebellar atrophy), and hereditary spastic paraplegia (including familial spastic paraparesis, familial spastic paraplegia, hereditary spastic paraparesis, Strumpell-Lorraine syndrome, and Strumpell's disease).

D. Myalgia

Myalgia is muscle pain and is a symptom of many diseases and disorders. The most common cause for myalgia is either overuse or over-stretching of a muscle or group of muscles. Myalgia without a traumatic history is often due to viral infections. Longer-term myalgias may be indicative of a metabolic myopathy, some nutritional deficiencies or chronic fatigue syndrome.

E. Infection

Infection can cause somatic pain. of such infection include, for example, an abscess in the muscle, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection.

F. Drugs

Drugs can cause somatic pain. Such drugs include, for example, cocaine, statins for lowering cholesterol (such as atorvastatin, simvastatin, and lovastatin), and ACE inhibitors for lowering blood pressure (such as enalapril and captopril).

G. Prolonged Nociceptive Pain Including without Limitation to Bone Fracture Pain, Spinal Stenosis, and Post-Surgical Pain.

V. Visceral Pain

The compositions and methods of the invention may be used to treat pain caused by or otherwise associated with any of the following visceral pain conditions. Visceral pain originates from body's viscera, or organs. Visceral nociceptors are located within body organs and internal cavities. The even greater scarcity of nociceptors in these areas produces pain that is usually more aching and of a longer duration than somatic pain. Visceral pain is extremely difficult to localise, and several injuries to visceral tissue exhibit "referred" pain, where the sensation is localised to an area completely unrelated to the site of injury.

Examples of visceral pain include the following.

A. Functional Visceral Pain

Functional visceral pain includes, for example, chronic functional abdominal pain (CFAP), non-cardiac chest pain (NCCP), chronic abdominal pain, functional heartburn, functional dyspepsia, irritable bowel syndrome, painful bladder syndrome, vulvodynia, pelvic pain syndrome.

B. Chronic Gastrointestinal Inflammation

Chronic gastrointestinal inflammation includes, for example, a gastritis, an inflammatory bowel disease, e.g., a Crohn's disease, an ulcerative colitis, a microscopic colitis, a diverticulitis and a gastroenteritis; an intestinal ischemia; a cholecystitis; an appendicitis; a gastroesophageal reflux; an ulcer, a nephrolithiasis, a pancreatitis and a hernia.

C. Autoimmune Pain

Autoimmune pain includes, for example, a sarcoidosis and a vasculitis.

D. Organic Visceral Pain

Organic visceral pain includes, for example, pain resulting from a traumatic, inflammatory or degenerative lesion of the gut or produced by a tumor impinging on sensory innervation.

E. Treatment-Induced Visceral Pain

Treatment-induced visceral pain includes, for example, a pain attendant to chemotherapy therapy or a pain attendant to radiation therapy.

VI. Referred Pain

The compositions and methods of the invention may be used to treat pain caused by or otherwise associated with any of the following referred pain conditions.

Referred pain arises from pain localized to an area separate from the site of pain stimulation. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot). Relieving the pressure on the nerve root may ameliorate the referred pain, provided that permanent nerve damage has not occurred. Myocardial ischaemia (the loss of blood flow to a part of the heart muscle tissue) is possibly the best known example of referred pain; the sensation can occur in the upper chest as a restricted feeling, or as an ache in the left shoulder, arm or even hand.

Administration

One can use any of the compounds described above to treat chronic pain. To "treat," as used here, means to deal with medically. It includes both preventing pain and relieving it, whether such prevention or relief is complete or partial.

Dose

The precise dose and frequency of administration depends on the severity and nature of the patient's condition, on the manner of administration, on the potency and pharmacodynamics of the particular compound employed, and on the judgment of the prescribing physician. Determining dose is a routine matter that is well within the capability of someone of ordinary skill in the art.

The compositions of the invention may be administered orally or parenterally, the later by subcutaneous injection, intramuscular injection, intravenous administration, or other route.

Excipients and Dosage Forms

Those skilled in the art will readily understand that for administering pharmaceutical compositions of the invention the S13P receptor inhibitor may be admixed with pharmaceutically acceptable excipient which are well known in the art.

A pharmaceutical composition to be administered systemically may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108, No. 4,166,452, and No. 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Injectables can be prepared in conventional forms, either as liquid solutions or suspensions, solid forms suitable for solution or suspension in liquid prior to injection, or as emulsions.

Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

EXAMPLES

The invention is illustrated by the following examples. The inventors administered various compounds of the invention to experimental animals and then assed the effects of those compounds in mitigating pain.

The Chung Rat Model

The inventors prepared rats according to the method of Kim and Chung described in *Pain,* 150, at 355-363 (1992) and in U.S. Pat. No. 7,091,232, both of which are incorporated by reference herein. According to this method, the L5 (and optionally the L6) spinal nerves on one side in rats are surgically ligated. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to low-threshold mechanical stimuli and will perceive pain instead of the faint sensation of touch. This sensitivity to normally non-painful touch, called "tactile allodynia," develops within the first week after surgery and lasts for at least two months. The allodynia response includes lifting the affected hindpaw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

Results

Table 1, below, shows the effects of various compounds of the invention on reversing allodynia in Chung model rats, as measured 15 minutes, 30 minutes, and 60 minutes after administration.

| COMPOUND | DOSE | ALLODYNIA REVERSAL (% vs. BASELINE) MEAN ± SE | | |
|---|---|---|---|---|
| | | 15 min post | 30 min post | 60 min post |
| Vehicle (20% ethanol) | 0 | 10.46 ± 3.35 | 16.40 ± 7.50 | 13.07 ± 7.91 |
| 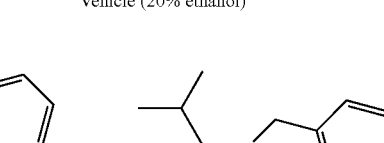 | 0.3 | 22.79 ± 12.89 | 58.57 ± 20.65 | 77.44 ± 17.05 |

-continued
| COMPOUND | DOSE | ALLODYNIA REVERSAL (% vs. BASELINE) MEAN ± SE | | |
| --- | --- | --- | --- | --- |
| | | 15 min post | 30 min post | 60 min post |
| 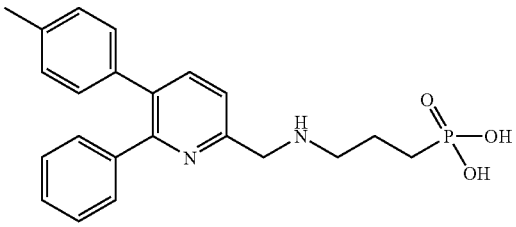 | 0.3 | 8.58 ± 1.79 | 95.90 ± 4.10 | 80.78 ± 14.48 |
| 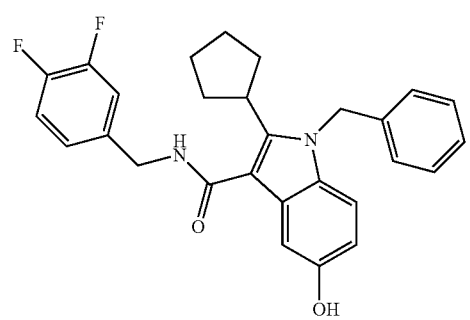 | 0.3 | 87.29 ± 12.70 | 82.77 ± 12.60 | 77.29 ± 13.95 |
| 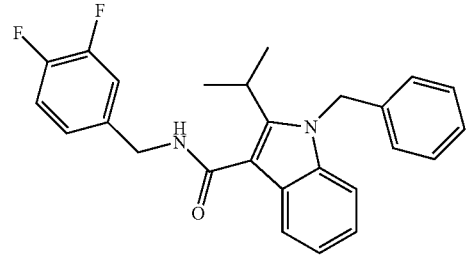 | 0.3 | 7.48 ± 3.89 | 60.78 ± 14.62 | 79.19 ± 13.92 |
| 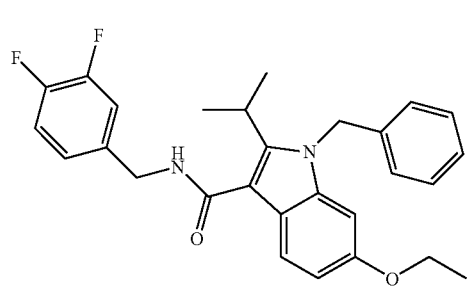 | 0.3 | 68.77 ± 13.82 | 73.30 ± 14.80 | 79.19 ± 13.92 |
| 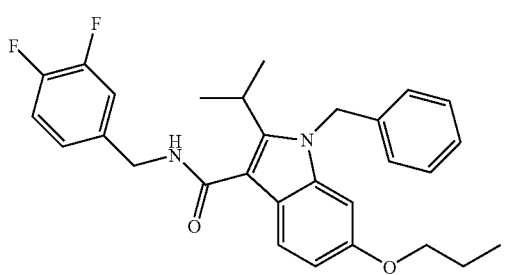 | 0.03 | 21.42 ± 19.66 | 28.86 ± 17.79 | 69.89 ± 18.41 |

| COMPOUND | DOSE | ALLODYNIA REVERSAL (% vs. BASELINE) MEAN ± SE | | |
|---|---|---|---|---|
| | | 15 min post | 30 min post | 60 min post |
| (structure) | 0.03 | 42.36 ± 23.52 | 65.01 ± 21.42 | 80.22 ± 14.41 |
| (structure) | 0.3 | 65.95 ± 17.78 | 100 ± 0.00 | 95.90 ± 4.10 |

Embodiments of the invention include the following:

1. A method for treating pain, the method comprising the step of administering to a patient in need of such treatment an S1P3 receptor inhibitor.

2. The method of 1, wherein the S1P3 receptor inhibitor is selective for the S1P3 receptor as compared to the S1P1 receptor, the S1P2 receptor, or both the S1P1 and S1P2 receptor.

3. A method for treating pain, the method comprising the step of administering to a patient in need of such treatment a compound represented by the general formula

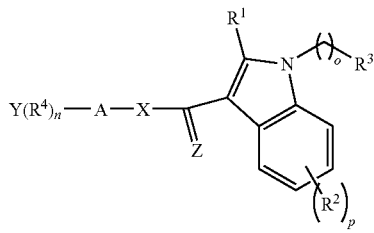

wherein
X is $NR^5$, O, S;
Z is O or S;
n is 0 or an integer of from 1 to 4;
o is 0 or an integer of from 1 to 3;
p is 0 or an integer of from 1 to 4;
A is $(C(R^5)_2)_m$, wherein
m is 0 or an integer of from 1 to 6;
$R^5$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, wherein said aryl is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur, halo, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl and sulfonyl groups;

Y is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;

$R^1$, $R^2$, $R^3$, $R^4$ are selected from the group consisting of hydrogen; straight or branched chain alkyl having 1 to 12 carbons; cycloalkyl having 3 to 6 carbons; alkenyl having 2 to 6 carbons and 1 or 2 double bonds; alkynyl having 2 to 6 carbons and 1 or 2 triple bonds; aryl wherein said aryl is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur; halo; $C_1$ to $C_{12}$ haloalkyl; hydroxyl; $C_1$ to $C_{12}$ alkoxy; $C_3$ to $C_{20}$ arylalkyloxy; $C_1$ to $C_{12}$ alkylcarbonyl; formyl; oxycarbonyl; carboxy; $C_1$ to $C_{12}$ alkyl carboxylate; $C_1$ to $C_{12}$ alkyl amide; aminocarbonyl; amino; cyano; diazo; nitro; thio; sulfoxyl; sulfonyl groups; or a group selected from the group consisting of

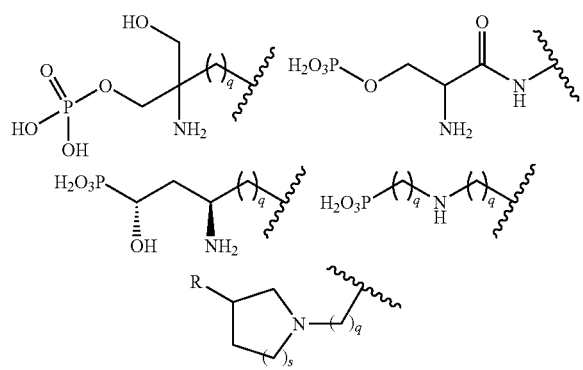

wherein R is CO₂H or PO₃H₂, p is an integer of 1 or 2 and q is 0 or an integer of 1 to 5 and s is 0 or an integer of 1 or 2; provided that, if Y is phenyl, it must be substituted with at least one $R^4$ group that is not hydrogen.

4. The method of 3 wherein Z is O.

5. The method of 3 wherein Y is a phenyl group, or a heterocyclic aryl group selected from the group consisting of pyridyl, thienyl, furyl, pyradizinyl, pyrimidinyl, pyrazinyl, thiazolyl, oxazolyl, and imidazolyl.

6. The method of 5 wherein each said aryl is independently selected from the group consisting of phenyl, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone, wherein said aryl is unsubstituted or is substituted with one or two alkyl, alkenyl, alkynyl, aryl, halo, haloalkyl, hydroxyl, alkoxyl, alkylcarbonyl, formyl, oxycarbonyl, carboxyl, alkyl carboxylate, alkyl amide, aminocarbonyl, amino, cyano, diazo, nitro, thio, sulfoxyl, or sulfonyl groups.

7. The method of 4 wherein Y is phenyl.

8. The method of 4 wherein A is CH₂.

9. The method of 8 wherein X is NH.

10. The method of 9 wherein n is 0 or an integer of 1 or 2 and $R^4$ is selected from the group consisting of methyl, methoxy, fluoro and chloro.

11. The method of 10 wherein $R^1$ is selected from the group consisting of hydrogen, methyl, ethyl and i-propyl.

12. The method of 8 wherein $R^3$ is selected from the group consisting of methyl, butyl, phenyl, benzyl, pyridyl, furanylmethylenyl, thienyl and thienyl methylenyl.

13. The method of 12 wherein p is 0 or p is 1 and $R^2$ is selected from the group consisting of hydroxyl, methoxy, nitro, amino, acetamido and benzyloxy.

14. The method of 13 wherein p is 1 and $R^2$ is a 5-hydroxy group; $R^1$ is selected from the group consisting of methyl, ethyl, i-propyl and phenyl; $R^3$ is selected from the group consisting of benzyl, thienylmethylenyl and furanylmethylenyl; n is 1 or 2 and $R^4$ is selected from the group consisting of methoxy and fluoro.

15. The method of 4 wherein said compound is selected from the group consisting of
1-Benzyl-5-hydroxy-2-methyl-1H-indole-3-carboxylic Acid, 3,5-Difluorobenzylamide;
5-Hydroxy-2-methyl-1-thiophen-2-ylmethyl-1H-indole-3-carboxylic Acid, 3,4-Difluorobenzylamide;
1-Butyl-5-hydroxy-2-methyl-1H-indole-3-carboxylic Acid, 3,5-Difluoro-benzylamide;
1-Furan-2-ylmethyl-5-hydroxy-2-methyl-1H-indole-3-carboxylic Acid, 3,4-Difluorobenzylamide;
5-Hydroxy-2-methyl-1-thiophen-2-ylmethyl-1H-indole-3-carboxylic Acid, 3,5-Difluorobenzylamide;
1-Furan-2-ylmethyl-5-hydroxy-2-methyl-1H-indole-3-carboxylic Acid 3,5-Difluorobenzylamide;
1-Benzyl-5-hydroxy-2-methyl-1H-indole-3-carboxylic Acid, 3,4-Difluoro-benzylamide;
5-Hydroxy-2-methyl-1-thiophen-2-ylmethyl-1H-indole-3-carboxylic Acid, 3-Fluorobenzylamide;
5-Hydroxy-2-methyl-1-thiophen-2-ylmethyl-1H-indole-3-carboxylic Acid, Benzylamide;
5-Hydroxy-2-methyl-1-thiophen-2-ylmethyl-1H-indole-3-carboxylic Acid, 3-Methoxybenzylamide;
1-Butyl-5-hydroxy-2-methyl-1H-indole-3-carboxylic Acid, 3-Methoxy-benzylamide;
5-Hydroxy-2-methyl-1-thiophen-2-ylmethyl-1H-indole-3-carboxylic Acid, 4-Fluorobenzylamide;
5-Hydroxy-2-methyl-1-thiophen-2-ylmethyl-1H-indole-3-carboxylic Acid, 4-Methylbenzylamide;
5-Hydroxy-2-methyl-1-thiophen-2-ylmethyl-1H-indole-3-carboxylic Acid, 3-Chlorobenzylamide;
5-Hydroxy-2-methyl-1-thiophen-2-ylmethyl-1H-indole-3-carboxylic Acid, 4-Chlorobenzylamide;
5-Hydroxy-2-methyl-1-thiophen-2-ylmethyl-1H-indole-3-carboxylic Acid, 2-methoxybenzylamide;
1-Benzyl-2-ethyl-5-hydroxy-1H-indole-3-carboxylic Acid, 3,4-Difluoro-benzylamide;
1-Benzyl-2-ethyl-5-hydroxy-1H-indole-3-carboxylic Acid, 3-Methoxy-benzylamide;
1-Benzyl-5-hydroxy-2-isopropyl-1H-indole-3-carboxylic Acid, 3,4-Difluorobenzamide;
5-Hydroxy-2-methyl-1-phenyl-1H-indole-3-carboxylic Acid 3,4-Difluoro-benzylamide;
5-Hydroxy-2-methyl-1-pyridin-2-yl-1H-indole-3-carboxylic Acid 3,4-Difluoro-benzylamide;
5-Hydroxy-2-methyl-1-thiophen-2-yl-1H-indole-3-carboxylic Acid 3,4-Difluorobenzylamide;
1-Benzyl-2-ethyl-5-hydroxy-1H-indole-3-carboxylic Acid 3,5-Difluoro-benzylamide;
1-Benzyl-5-hydroxy-2-isopropyl-1H-indole-3-carboxylic Acid, 3,5-difluorobenzylamide;
1-Benzyl-5-hydroxy-2-isopropyl-1H-indole-3-carboxylic Acid, 3-methoxybenzylamide; and
1-Benzyl-5-hydroxy-2-phenyl-1H-indole-3-carboxylic Acid, 3,5-Difluoro-benzylamide.

16. The method of 15 wherein said compound is selected from the group consisting of
1-Benzyl-5-hydroxy-2-methyl-1H-indole-3-carboxylic Acid, 3,5-Difluorobenzylamide;
1-Furan-2-ylmethyl-5-hydroxy-2-methyl-1H-indole-3-carboxylic Acid 3,5-Difluorobenzylamide;
5-Hydroxy-2-methyl-1-thiophen-2-ylmethyl-1H-indole-3-carboxylic Acid, 3-Methoxybenzylamide;
1-Benzyl-2-ethyl-5-hydroxy-1H-indole-3-carboxylic Acid, 3,4-Difluoro-benzylamide;
1-Benzyl-2-ethyl-5-hydroxy-1H-indole-3-carboxylic Acid 3,5-Difluoro-benzylamide;
1-Benzyl-5-hydroxy-2-isopropyl-1H-indole-3-carboxylic Acid, 3,5-difluorobenzylamide;
1-Benzyl-5-hydroxy-2-isopropyl-1H-indole-3-carboxylic Acid, 3-methoxybenzylamide; and
1-Benzyl-5-hydroxy-2-phenyl-1H-indole-3-carboxylic Acid, 3,5-Difluoro-benzylamide.

17. A method for treating pain, the method comprising the step of administering to a patient in need of such treatment a compound represented by the general formula I:

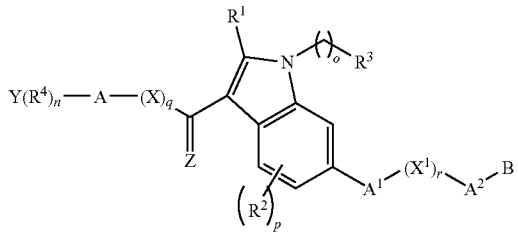

Formula I wherein:

$R^1 R^2$, $R^3$ and $R^4$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, carbocyclic hydrocarbon groups having from 3 to 20 carbon atoms, heterocyclic groups having up to 20 carbon atoms and at least one of oxygen, nitrogen and/or sulfur in the ring, halo, $C_1$ to $C_{12}$ haloalkyl, hydroxyl, $C_1$ to $C_{12}$ alkoxy, $C_3$ to $C_{20}$ arylalkyloxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, and sulfonyl groups;

X and $X^1$ are independently selected from the group consisting of $NR^5$, O and S;

$R^5$ is hydrogen, an alkyl group of 1 to 10 carbons, a cycloalkyl group of 5 to 10 carbons, phenyl or lower alkylphenyl;

Y is a carbocyclic aryl or heterocyclic aryl group wherein said carbocyclic aryl comprises from 6 to 20 atoms and said heterocyclic aryl comprises from 2 to 20 carbon atoms and from 1 to 5 heteroatoms selected from the group consisting of nitrogen, oxygen and sulfur, and wherein said aryl may be bonded to A at any position;

Z is O or S;

n is 0 or an integer of from 1 to 5;

o is 0 or an integer of from 1 to 3;

p is 0 or an integer of from 1 to 3;

q is 0 or 1;

r is 0 or 1;

A, $A^1$ and $A^2$ are independently selected from the group consisting of $(CH_2)_v$ wherein v is 0 or an integer of from 1 to 12, branched chain alkyl having 3 to 12 carbons, cycloalkyl having 3 to 12 carbons, alkenyl having 2 to 10 carbons and 1-3 double bonds and alkynyl having 2 to 10 carbons and 1 to 3 triple bonds;

B is selected from the group consisting of hydrogen, $OR^6$, $COOR^7$, $NR^8R^9$, $CONR^8R^9$, $COR^{10}$, $CH=NOR^{11}$, $CH=NNR^{12}R^{13}$, wherein $R^6$, $R^7$, $R^{10}$ and $R^{11}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, $R^8$, $R^9$, $R^{12}$ and $R^{13}$ are independently selected from the group consisting of hydrogen, straight or branched chain alkyl having 1 to 12 carbons, alkenyl having 2 to 6 carbons and 1 or 2 double bonds, alkynyl having 2 to 6 carbons and 1 or 2 triple bonds, a carbocyclic hydrocarbon group having from 3 to 20 carbon atoms, a heterocyclic group having up to 20 carbon atoms and at least one of oxygen, nitrogen and/or sulfur in the ring, or $R^8$ and $R^9$ and/or $R^{12}$ and $R^{13}$, together, can form a divalent carbon radical of 2 to 5 carbons to form a heterocyclic ring with nitrogen, wherein any of $R^6$, $R^7$, $R^8$, $R^9$, $R^{10}$, $R^{11}$, $R^{12}$ or $R^{13}$ (may be substituted with one or more halogen, hydroxy, alkyloxy, cyano, nitro, mercapto or thiol radical; provided however, when v is 0, and r is 0, B is not hydrogen; or B is a carbocyclic hydrocarbon group having from 3 to 20 carbon atoms, or a heterocyclic group having up to 20 carbon atoms and at least one of oxygen, nitrogen and/or sulfur in the ring, and wherein when said B is a carbocyclic or heterocyclic group B may be bonded to $A^2$ at any position, or a pharmaceutically acceptable salt of said compound.

18. The method of 17, wherein the compound is selected from the group consisting of the following compounds:

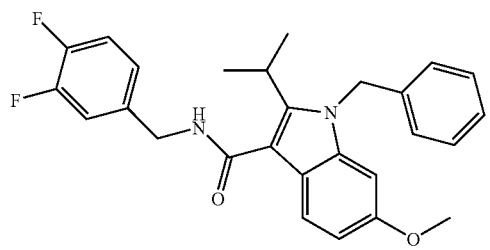 [SMILES: COc1ccc2c(C(=O)NCc3ccc(F)c(F)c3)c(C(C)C)n(Cc3ccccc3)c2c1]

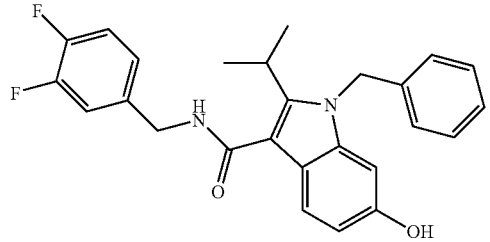 [SMILES: CC(C)c1c(C(=O)NCc2ccc(F)c(F)c2)c2ccc(O)cc2n1Cc1ccccc1]

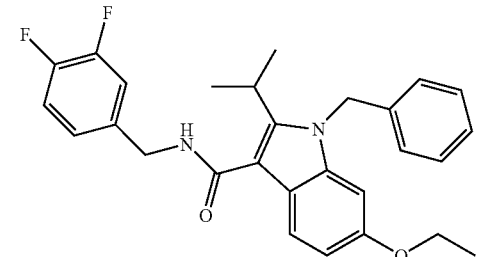

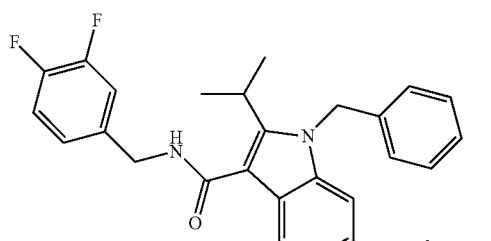

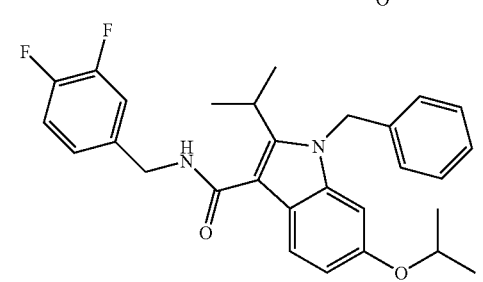

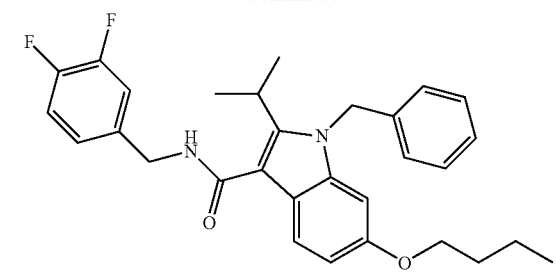
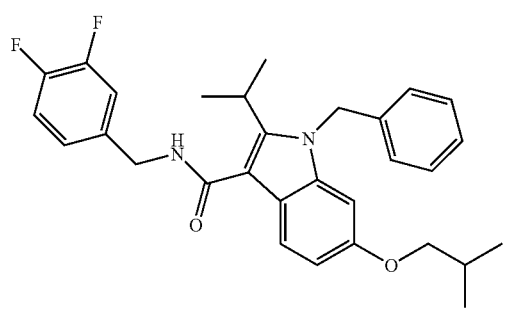 [SMILES: CC(C)COc1ccc2c(C(=O)NCc3ccc(F)c(F)c3)c(C(C)C)n(Cc3ccccc3)c2c1]
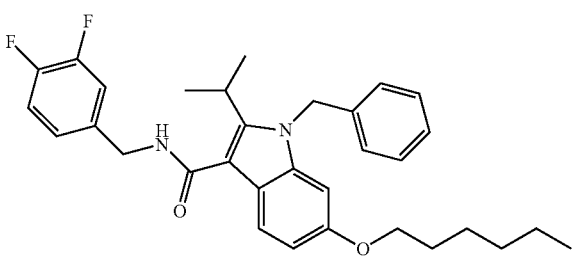 [SMILES: CCCCCCOc1ccc2c(C(=O)NCc3ccc(F)c(F)c3)c(C(C)C)n(Cc3ccccc3)c2c1]
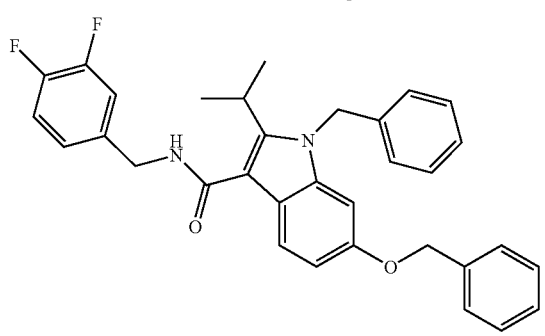 [SMILES: CC(C)c1c(C(=O)NCc2ccc(F)c(F)c2)c2ccc(OCc3ccccc3)cc2n1Cc1ccccc1]
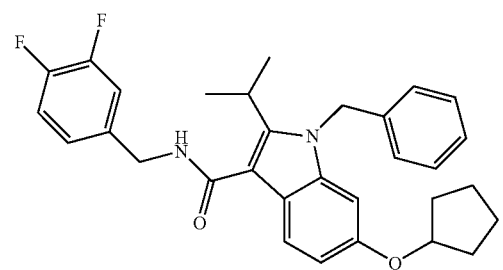 [SMILES: CC(C)c1c(C(=O)NCc2ccc(F)c(F)c2)c2ccc(OC3CCCC3)cc2n1Cc1ccccc1]
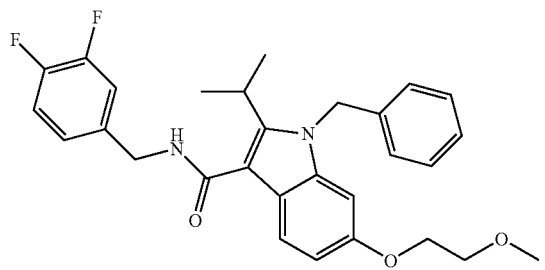 [SMILES: COCCOc1ccc2c(C(=O)NCc3ccc(F)c(F)c3)c(C(C)C)n(Cc3ccccc3)c2c1]
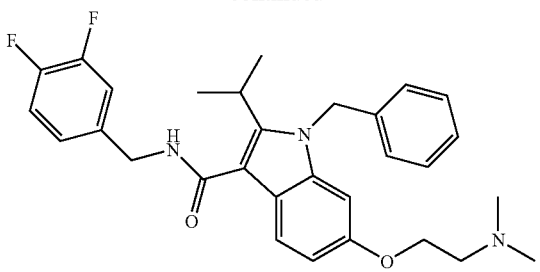 [SMILES: CC(C)c1c(C(=O)NCc2ccc(F)c(F)c2)c2ccc(OCCN(C)C)cc2n1Cc1ccccc1]
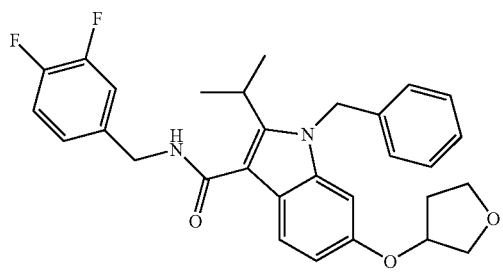 [SMILES: CC(C)c1c(C(=O)NCc2ccc(F)c(F)c2)c2ccc(OC3CCOC3)cc2n1Cc1ccccc1]
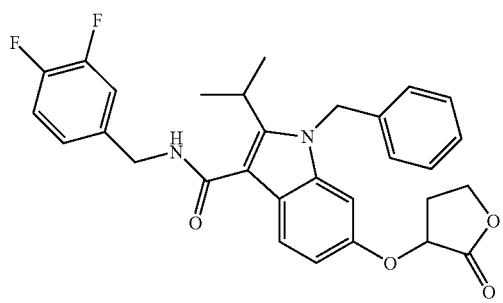 [SMILES: CC(C)c1c(C(=O)NCc2ccc(F)c(F)c2)c2ccc(OC3CCOC3=O)cc2n1Cc1ccccc1]
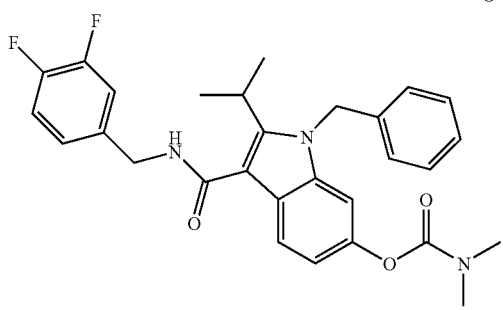
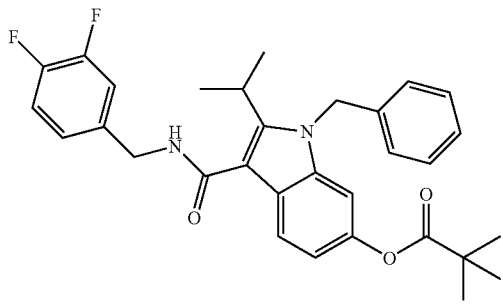 [SMILES: CC(C)c1c(C(=O)NCc2ccc(F)c(F)c2)c2ccc(OC(=O)C(C)(C)C)cc2n1Cc1ccccc1]
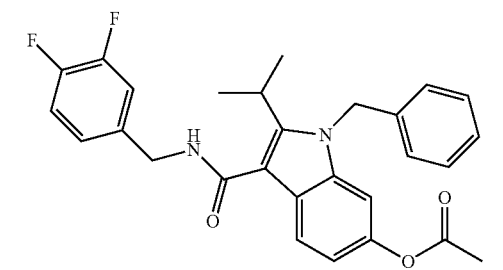 [SMILES: CC(=O)Oc1ccc2c(C(=O)NCc3ccc(F)c(F)c3)c(C(C)C)n(Cc3ccccc3)c2c1]

83
-continued
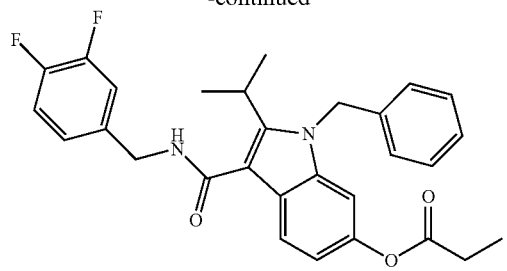
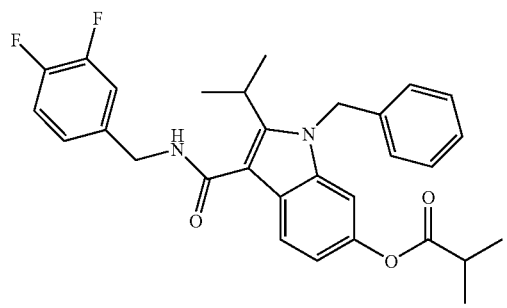
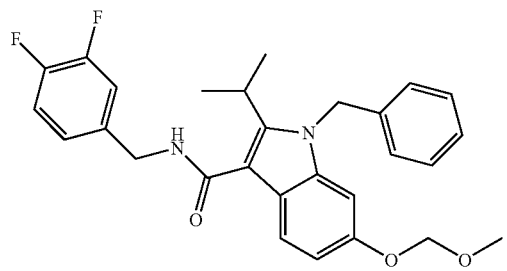
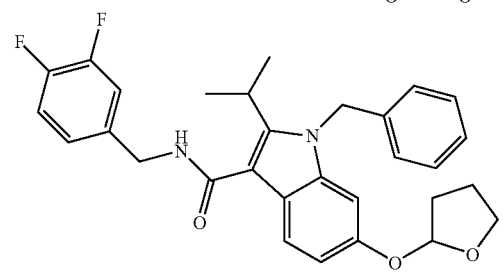
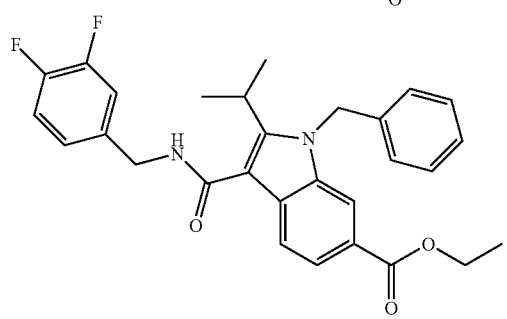
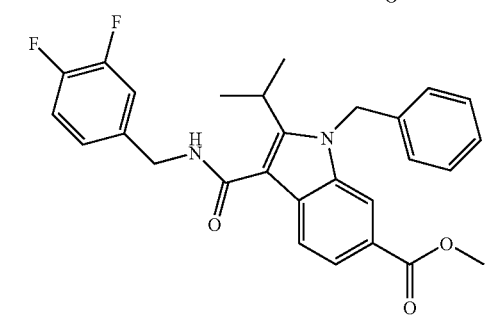
84
-continued
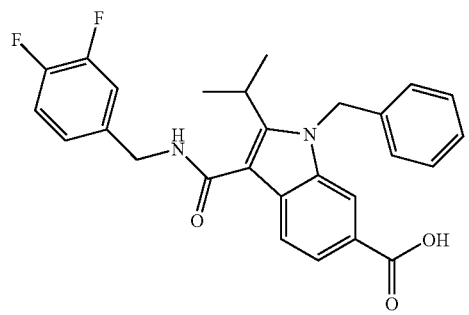 [SMILES: COC(=O)c1ccc2c(C(=O)NCc3ccc(F)c(F)c3)c(C(C)C)n(Cc3ccccc3)c2c1]
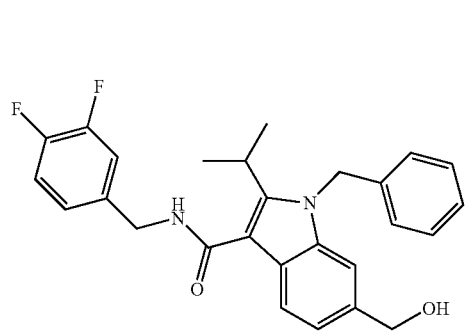 [SMILES: CC(C)c1c(C(=O)NCc2ccc(F)c(F)c2)c2ccc(CO)cc2n1Cc1ccccc1]
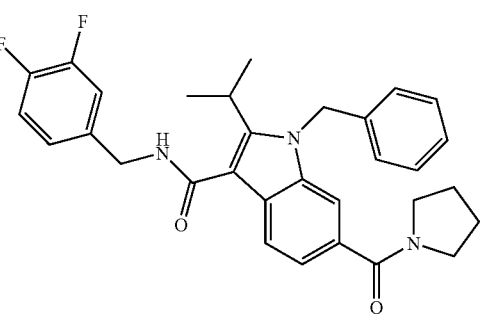 [SMILES: CC(C)c1c(C(=O)NCc2ccc(F)c(F)c2)c2ccc(C(=O)N3CCCC3)cc2n1Cc1ccccc1]
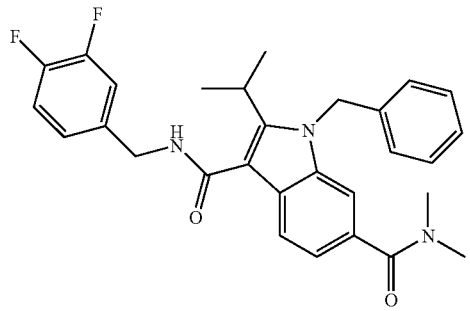
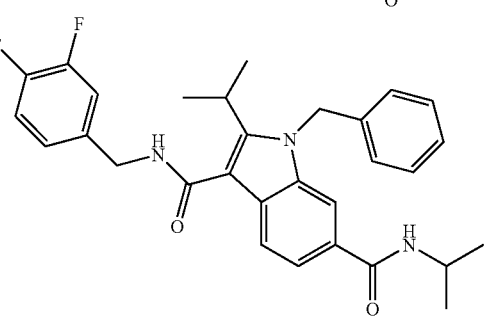

85
-continued
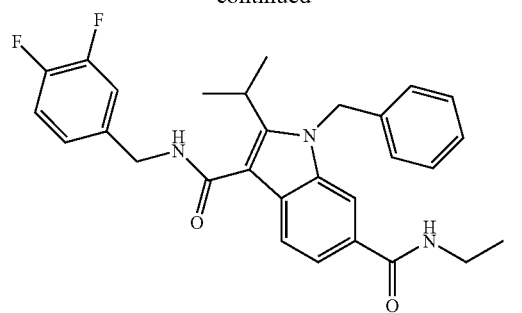
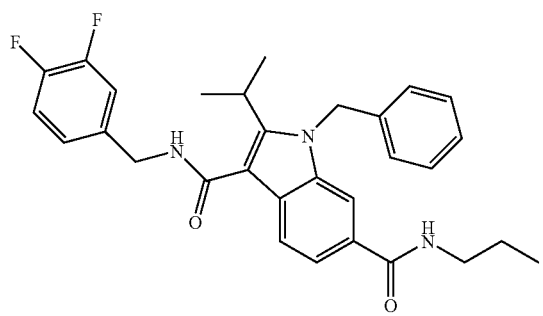 [SMILES: CCCNC(=O)c1ccc2c(C(=O)NCc3ccc(F)c(F)c3)c(C(C)C)n(Cc3ccccc3)c2c1]
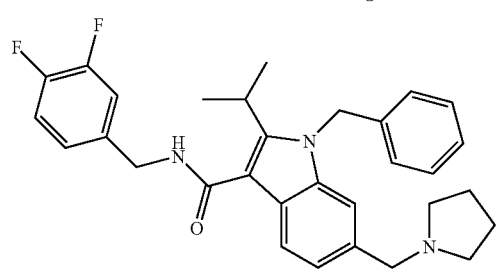
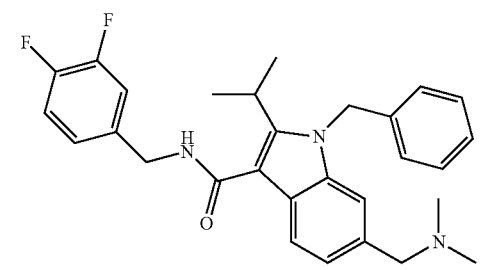 [SMILES: CC(C)c1c(C(=O)NCc2ccc(F)c(F)c2)c2ccc(CN(C)C)cc2n1Cc1ccccc1]
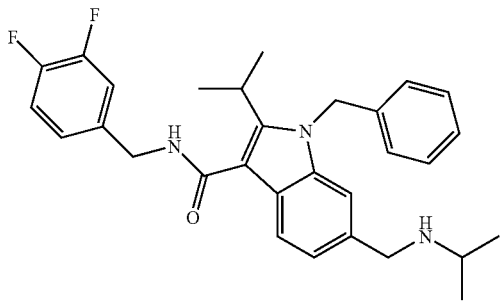 [SMILES: CC(C)NCc1ccc2c(C(=O)NCc3ccc(F)c(F)c3)c(C(C)C)n(Cc3ccccc3)c2c1]
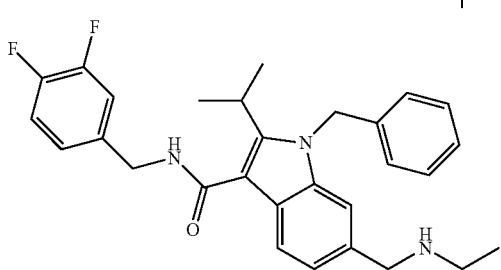
86
-continued
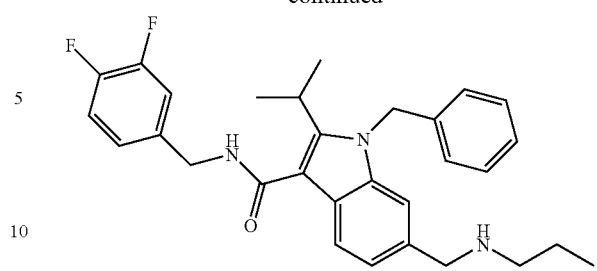
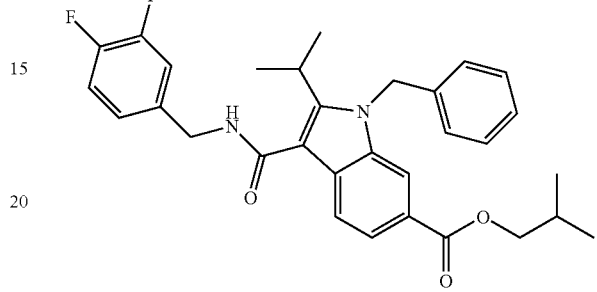
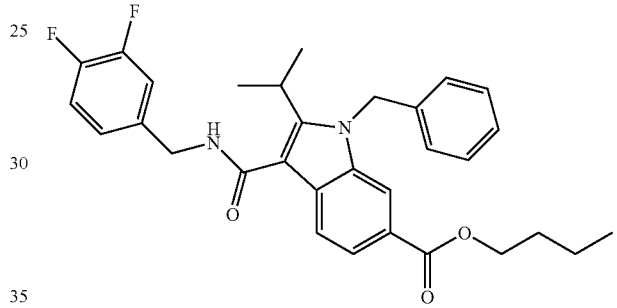
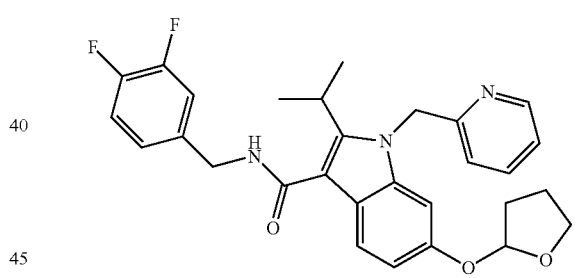
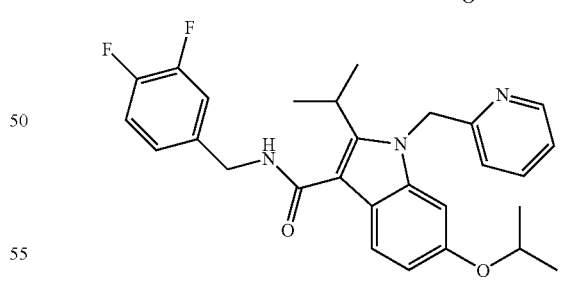
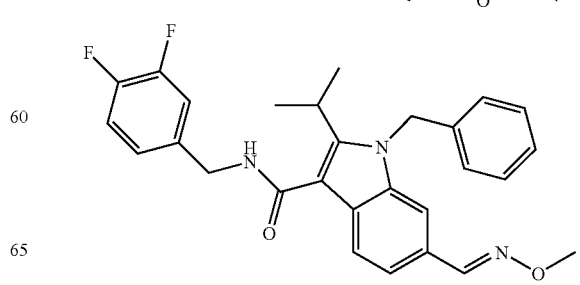

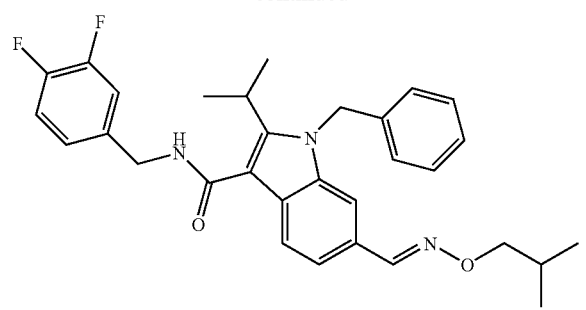 [SMILES: CC(C)CO/N=C/c1ccc2c(C(=O)NCc3ccc(F)c(F)c3)c(C(C)C)n(Cc3ccccc3)c2c1]
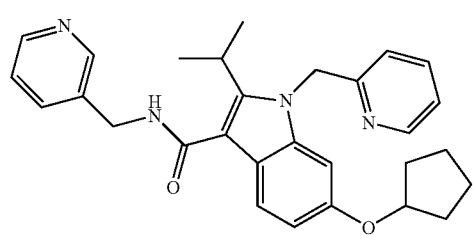 [SMILES: CC(C)c1c(C(=O)NCc2cccnc2)c2ccc(OC3CCCC3)cc2n1Cc1ccccn1]
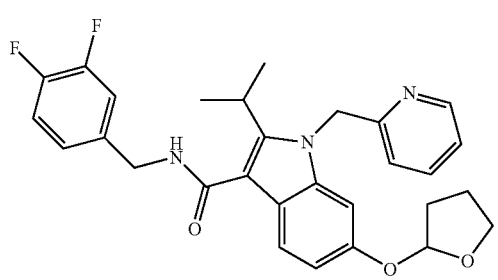 [SMILES: CC(C)c1c(C(=O)NCc2ccc(F)c(F)c2)c2ccc(OC3CCCO3)cc2n1Cc1ccccn1]
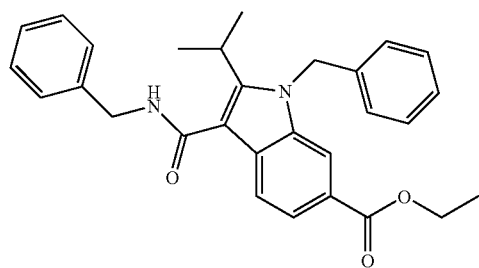 [SMILES: CCOC(=O)c1ccc2c(C(=O)NCc3ccccc3)c(C(C)C)n(Cc3ccccc3)c2c1]
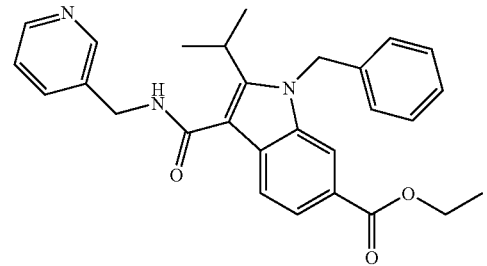 [SMILES: CCOC(=O)c1ccc2c(C(=O)NCc3cccnc3)c(C(C)C)n(Cc3ccccc3)c2c1]
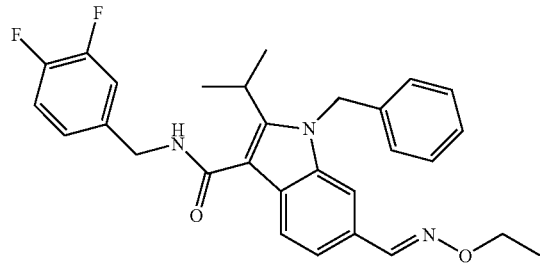 [SMILES: CCO/N=C/c1ccc2c(C(=O)NCc3ccc(F)c(F)c3)c(C(C)C)n(Cc3ccccc3)c2c1]
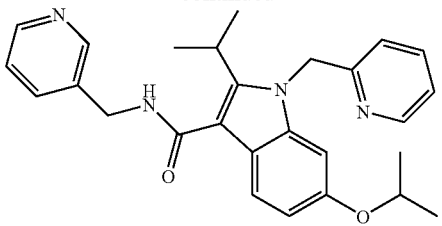 [SMILES: CC(C)Oc1ccc2c(C(=O)NCc3cccnc3)c(C(C)C)n(Cc3ccccn3)c2c1]
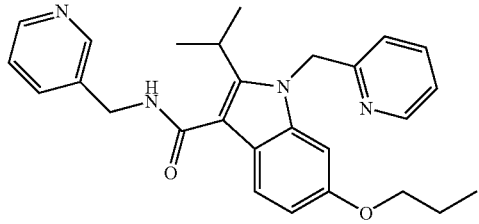 [SMILES: CCCOc1ccc2c(C(=O)NCc3cccnc3)c(C(C)C)n(Cc3ccccn3)c2c1]
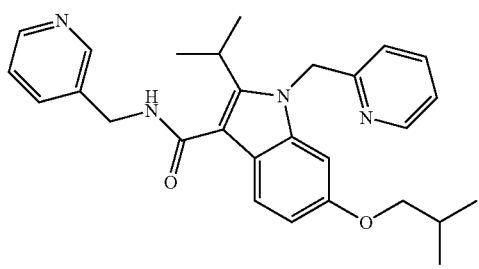 [SMILES: CC(C)COc1ccc2c(C(=O)NCc3cccnc3)c(C(C)C)n(Cc3ccccn3)c2c1]
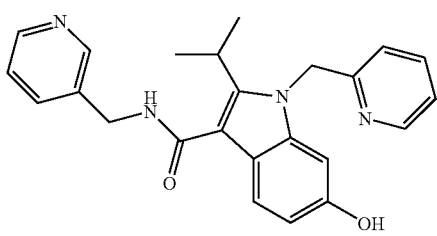 [SMILES: CC(C)c1c(C(=O)NCc2cccnc2)c2ccc(O)cc2n1Cc1ccccn1]
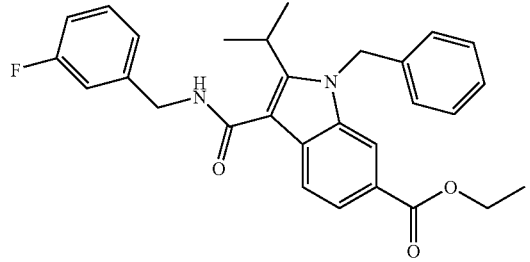 [SMILES: CCOC(=O)c1ccc2c(C(=O)NCc3cccc(F)c3)c(C(C)C)n(Cc3ccccc3)c2c1]
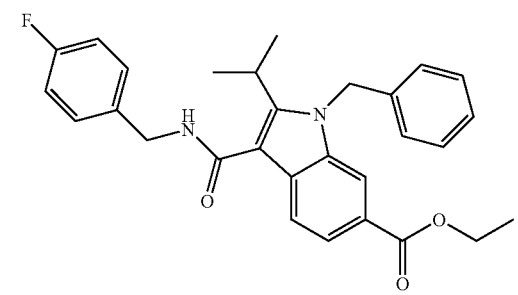 [SMILES: CCOC(=O)c1ccc2c(C(=O)NCc3ccc(F)cc3)c(C(C)C)n(Cc3ccccc3)c2c1]

89
-continued
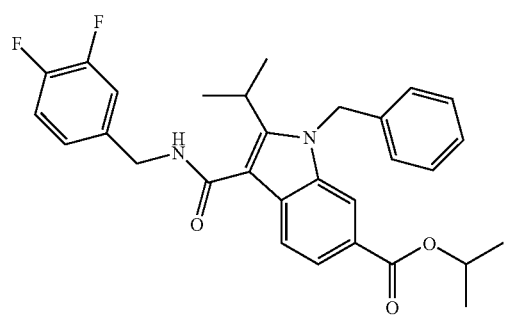 [SMILES: CC(C)OC(=O)c1ccc2c(C(=O)NCc3ccc(F)c(F)c3)c(C(C)C)n(Cc3ccccc3)c2c1]
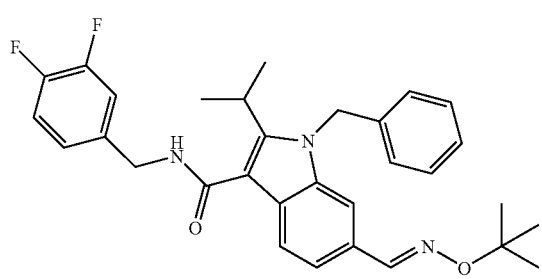 [SMILES: CC(C)c1c(C(=O)NCc2ccc(F)c(F)c2)c2ccc(/C=N/OC(C)(C)C)cc2n1Cc1ccccc1]
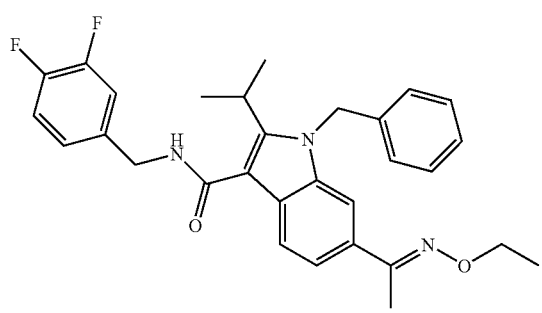 [SMILES: CCO/N=C(\C)c1ccc2c(C(=O)NCc3ccc(F)c(F)c3)c(C(C)C)n(Cc3ccccc3)c2c1]
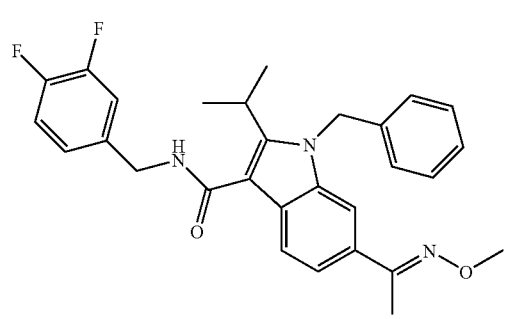 [SMILES: CO/N=C(\C)c1ccc2c(C(=O)NCc3ccc(F)c(F)c3)c(C(C)C)n(Cc3ccccc3)c2c1]
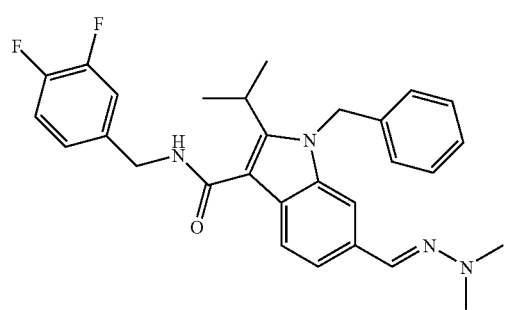 [SMILES: CC(C)c1c(C(=O)NCc2ccc(F)c(F)c2)c2ccc(/C=N/N(C)C)cc2n1Cc1ccccc1]
90
-continued
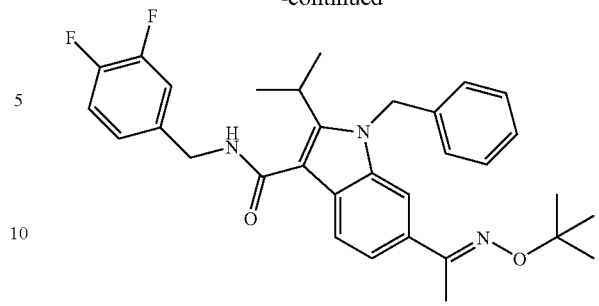
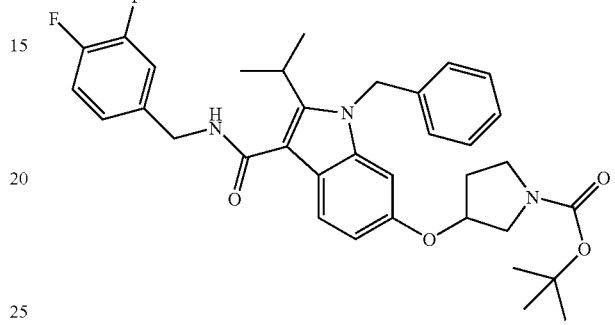
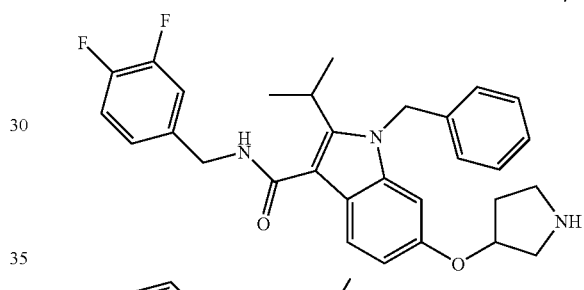
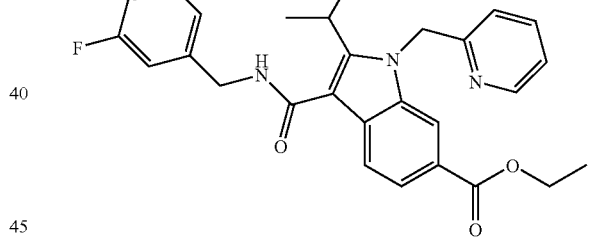
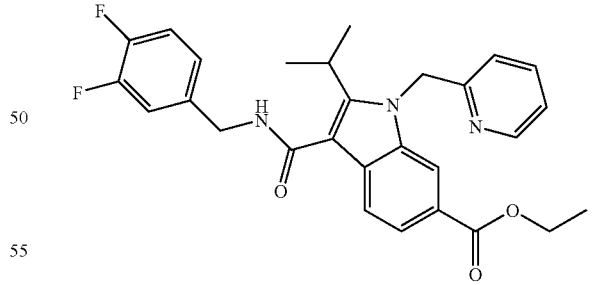
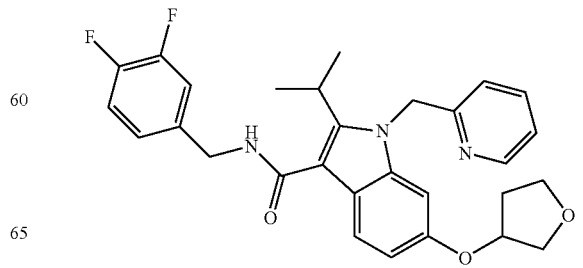

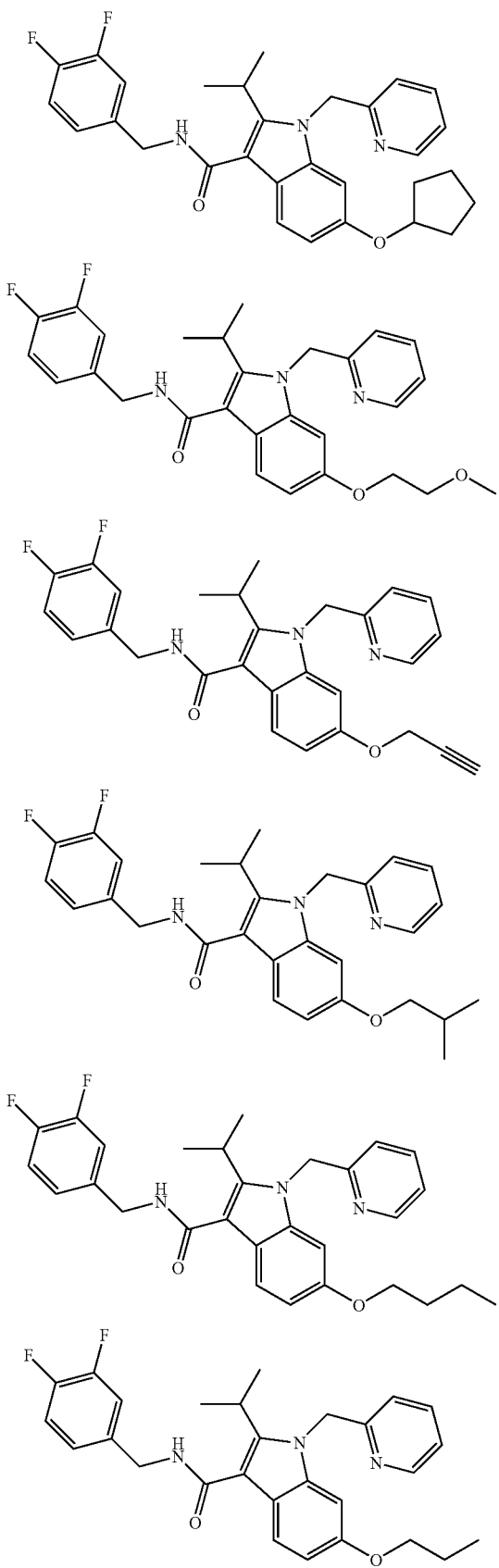

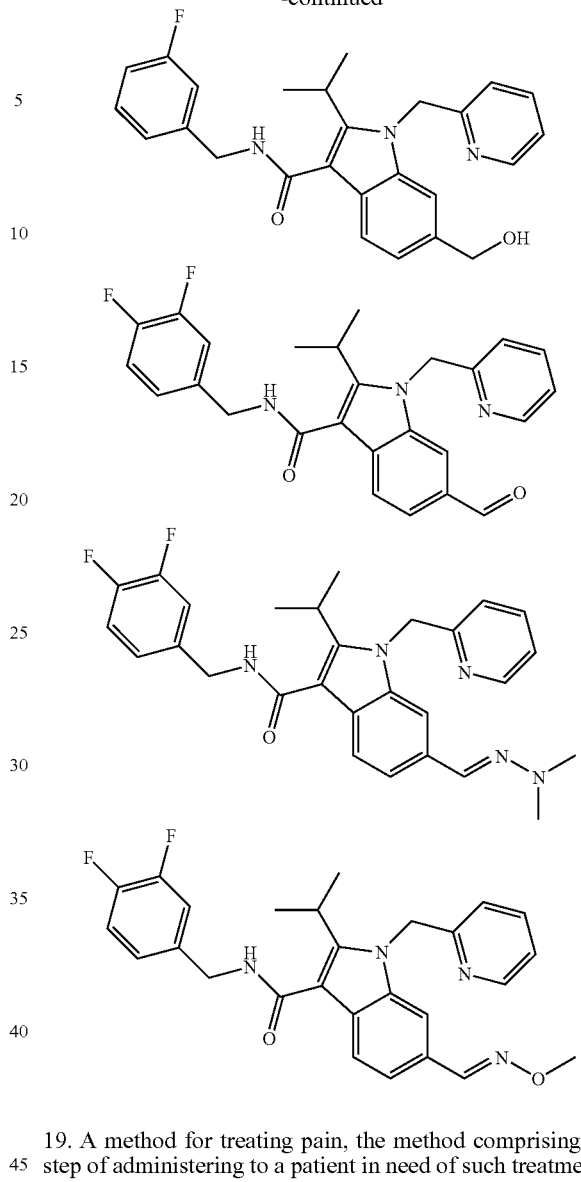

19. A method for treating pain, the method comprising the step of administering to a patient in need of such treatment a compound represented by the general formula

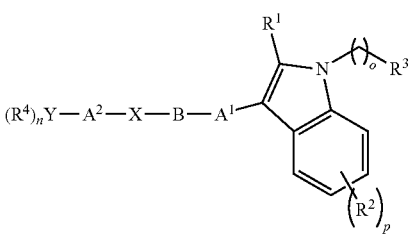

wherein:

$A^1$ and $A^2$ are independently selected from the group consisting of $(CH_2)_m$ where m is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $NR^5$, O and S;

B is selected from the group consisting of $(CH_2)n$, where n is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, C=C($R^5$)$_2$, C=O, C=S, $R^5$C=N$R^5$, $R^5$C=C$R^5$, C=NO$R^5$, C$R^5$O$R^5$, C(O$R^5$)$_2$, C$R^5$N($R^5$)$_2$, C(N($R^5$)$_2$)$_2$, C$R^5$S$R^5$, C(S$R^5$)$_2$, SO, SO$_2$, and heterocyclic aryl comprising from 2 to 14 carbon atoms and from 1 to 3 heteroatoms selected from the group consisting of nitrogen, oxygen and sulfur;

X is selected from the group consisting of (CH$_2$)$_r$, where r is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, N$R^5$, O and S;

provided that when m is 0 and B is C=O then X is not N$R^5$, O or S;

Y is $R^6$, or a carbocyclic aryl group comprising from 6 to 14 carbon atoms or a heterocyclic aryl group comprising from 2 to 14 carbon atoms and from 1 to 3 heteroatoms selected from the group consisting of nitrogen, oxygen and sulfur;

o is 0 or an integer of from 1 to 3;

p is 0 or an integer of from 1 to 4;

$R^1$, $R^2$, $R^3$, $R^4$ are independently selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, halo, $C_1$ to $C_{12}$ haloalkyl, hydroxy, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, sulfonyl,

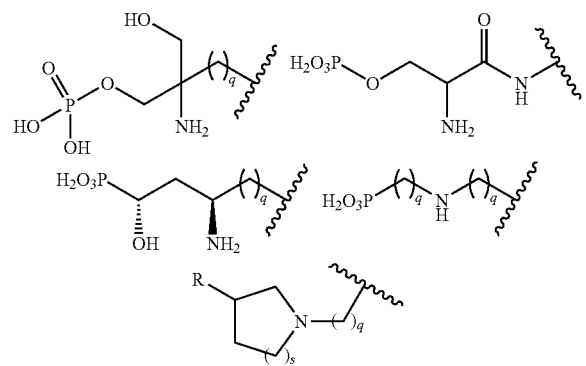

wherein R is CO$_2$H or PO$_3$H$_2$ and q is 0 or an integer of 1 to 5 and s is 0 or an integer from 1 to 3;

$R^5$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, halo, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl and sulfonyl; and $R^6$ is selected from the group consisting of straight or branched chain alkyl having 1 to 12 carbons, cycloalkyl having 3 to 6 carbons, alkenyl having 2 to 6 carbons and 1 or 2 double bonds and alkynyl having 2 to 6 carbons and 1 or 2 triple bonds.

20. The method of 19 wherein said aryl group is selected from the group consisting of benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalene, chromene, thiochromene, dihydroquinoline, indan, dihydrobenzofuran, dihydrobenzothiophene, indene, benzofuran, benzothiophene, coumarin and coumarinone, which aryl is unsubstituted or is substituted with one or two alkyl, alkenyl, alkynyl, aryl, halo, haloalkyl, hydroxyl, alkoxyl, alkylcarbonyl, formyl, oxycarbonyl, carboxyl, alkyl carboxylate, alkyl amide, aminocarbonyl, amino, cyano, diazo, nitro, thio, sulfoxyl, or sulfonyl groups.

21. The method of 20 wherein o is 1 and $R^3$ is phenyl.

22. The method of 21 wherein $R^1$ is i-propyl.

23. The method of 22 wherein p is 1 and $R^2$ is hydroxy methyloxymethyloxy or dihydropyranyloxy.

24. The method of 23 wherein B is selected from the group consisting of C=C($R^5$)$_2$, C=O and C=NO$R^5$.

25. The method of 24 wherein Y is $R^6$.

26. The method of 25 wherein $R^6$ is selected from the group consisting of methyl, n-propyl, and i-butyl.

27. The method of 22 wherein Y is selected from the group consisting of phenyl and 2,5 difluoro phenyl.

28. The method of 27 wherein p is 0 or p is 1 and $R^2$ is selected from the group consisting of hydroxy and dihyropyranyloxy.

29. The method of 28 wherein $A^1$ and $A^2$ are absent, B is C=O and X is ethyl or ethenyl.

30. The method of 28 wherein $A^1$ and $A^2$ are absent, B is $C_2H_4$ and X is CH$_2$.

31. The method of 28 wherein $A^1$ and $A^2$ are absent, B is sulfonyl; and X is NH.

32. The method of 28 wherein $A^1$, $A^2$ and B are absent and X is oxadiazolyl.

33. The method of 28 wherein $A^1$ is absent, B is C=O, X is NH and $A^2$ is NH.

34. The method of 19 wherein the compound is selected from the group consisting of 1-Benzyl-3-((3,5-difluorobenzylamino)methyl)-2-isopropyl-1H-indol-5-ol, (E)-1-Benzyl-5-hydroxy-2-isopropyl-1H-indole-3-carboxaldehyde, O-Benzyl Oxime, (E)-1-Benzyl-5-hydroxy-2-isopropyl-1H-indole-3-carbaldehyde, O-Phenyl Oxime, (E)-1-(1-Benzyl-5-hydroxy-2-isopropyl-1H-indol-3-yl)-3-phenylpropenone, 1-(1-Benzyl-5-hydroxy-2-isopropyl-1H-indol-3-yl)-3-phenylpropan-1-one, 1-(1-Benzyl-5-hydroxy-2-isopropyl-1H-indol-3-yl)ethanone, 1-(1-Benzyl-5-hydroxy-2-isopropyl-1H-indol-3-yl)butan-1-one, 1-(1-Benzyl-5-hydroxy-2-isopropyl-1H-indol-3-yl)-3-methylbutan-1-one, 1-(1-Benzyl-5-hydroxy-2-isopropyl-1H-indol-3-yl)-2-phenylethan-1-one, (E)-1-(1-Benzyl-5-hydroxy-2-isopropyl-1H-indol-3-yl)-3-(3,4-difluorophenyl)prop-2-en-1-one and 1-(1-Benzyl-5-hydroxy-2-isopropyl-1H-indol-3-yl)-3-(3,4-difluorophenyl)propan-1-one.

35. A method of treating pain, the method comprising the step of administering to a patient in need of such treatment a compound represented by the general formula

[Structure diagram: ring with R¹, R², X, Y, Z positions]

[C(O)_u(R³)_v]_a(W)_b[C(R⁴)_2]_c[P(O)(OR³)_2]_d[C(O)_x(OR³)_y(R³)_z]_e wherein
X is selected from the group consisting of $CR^3$ and N;
Y is selected from the group consisting of $CR^3$ and N;
Z is selected from the group consisting of $CR^3$ and N;
at least one of X, Y and Z is N;
W is $NR^3$ or O;
$R^1$ is an aryl group;
$R^2$ is an aryl group;
$R^3$ is selected from the group consisting of H and alkyl; and 2 of said $R^3$ groups may together with N may form a heterocylic ring having from 2 to 6 carbon atoms; $R^4$ is selected from the group consisting of H, alkyl, $OR^3$, and $N(R^3)_2$;
a is 0 or an integer of from 1 to 6;
b is 0 or 1;
c is 0 or an integer of from 1 to 6;
d is 0 or 1;
e is 0 or 1;
u is 0 or 1;
v is 0 or an integer of from 1 to 2;
x is 0 or 1;
y is 0 or an integer of from 1 to 3;
z is 0 or an integer of from 1 to 3;
provided, however, that when d is 0, e is 1, and when e is 0, d is 1.

36. The method of 35, wherein $R^1$ is selected from the group consisting of phenyl and substituted derivatives thereof;
$R^2$ is selected from the group consisting of phenyl, furanyl, thienyl, pyridyl, pyranyl and substituted derivatives thereof;
$R^3$ is selected from the group consisting of H and lower alkyl;
$R^4$ is selected from the group consisting of H and lower alkyl;
a is 0 or an integer of from 1 to 3;
c is 0 or an integer of from 1 to 5;
37. The method of 36, wherein e is 0.
38. The method of 37, wherein $R^{a1}$ is represented by the general formula

[Structure: R⁵-substituted phenyl with methyl]

wherein $R^5$ is selected from the group consisting of H, alkyl, trifluoromethyl, trifluoromethyloxy, halo and lower alkylthio.
39. The method of 38, wherein $R^2$ is selected from the group consisting of furanyl, thienyl, pyridyl and pyranyl or $R^2$ is represented by the general formula

[Structure: R⁵-substituted phenyl with methyl]

wherein $R^5$ is selected from the group consisting of H, alkyl, trifluoromethyl, trifluoromethyloxy, halo, and lower alkylthio.
40. The method of 39, wherein $R^3$ is H.
41. The method of 40, wherein c is 1, 2 or 3.
42. The method of 40, wherein a is 1.
43. The method of 42, wherein Z is N and X and Y are $CR^3$.
44. The method of 43, wherein W is $NR^3$, $R^2$ is phenyl and $R^5$ is selected from the group consisting of H and methyl.
45. The method of 44, wherein $R^2$ is pyridyl and $R^5$ is ethyl, and W is $NR^3$.
46. The method of 36, wherein d is 0.
47. The method of 46, wherein $R^1$ is represented by the general formula

[Structure: R⁵-substituted phenyl with methyl]

wherein $R^5$ is selected from the group consisting of H, alkyl, trifluoromethyl, trifluoromethyloxy, halo, and loweralkylthio
48. The method of 47, wherein $R^2$ is represented by the general formula

[Structure: R⁵-substituted phenyl with methyl]

wherein $R^5$ is selected from the group consisting of H, lower alkyl, trifluoromethyl, trifluoromethyloxy, halo, and lower alkylthio or $R^2$ is selected from the group consisting of furanyl, thienyl, pyridyl and pyranyl.
49. The method of 47, wherein $R^3$ is H.
50. The method of 49, wherein a is 1.
51. The method of 50, wherein x is 1 and z is 0.
52. The method of 51, wherein $R^4$ is selected from the group consisting of H, methyl, and ethyl.
53. The method of 52, wherein Z is N, X and Y are $CR^3$, $R^2$ is pyridyl, and $R^5$ is selected from the group consisting of H, methyl, ethyl, propyl and trifluoromethyl.
54. The method of 52, wherein X, Y and Z are N, $R^5$ is selected from the group consisting of H, methyl, ethyl, propyl and trifluoromethyl.
55. The method of 52, wherein X and Z are N and Y is $CR^3$.
56. The method of 49, wherein y is 0.
57. The method of 35, wherein the compound is selected from the group consisting of

[Structure: diphenyl-pyridine with CH2NH-propyl-phosphonic acid]

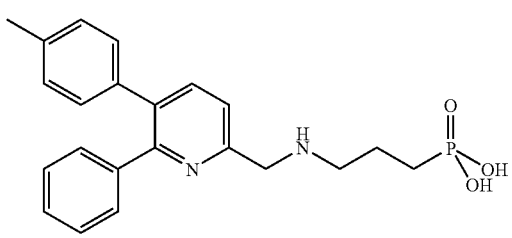 [SMILES: Cc1ccc(-c2ccc(CNCCCP(=O)(O)O)nc2-c2ccccc2)cc1]
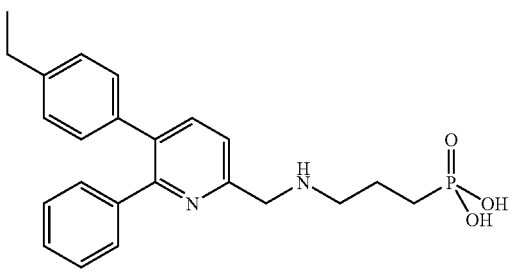
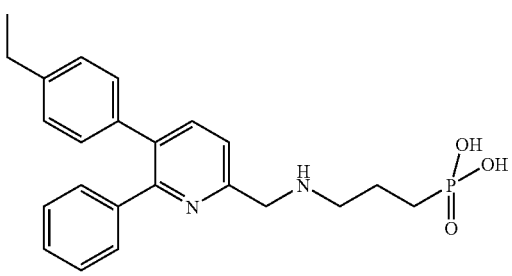
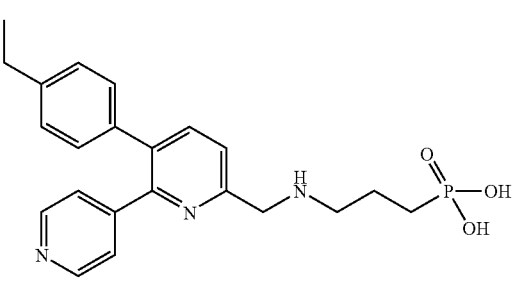 [SMILES: CCc1ccc(-c2ccc(CNCCCP(=O)(O)O)nc2-c2ccncc2)cc1]
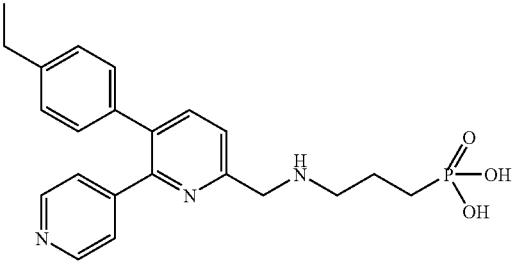
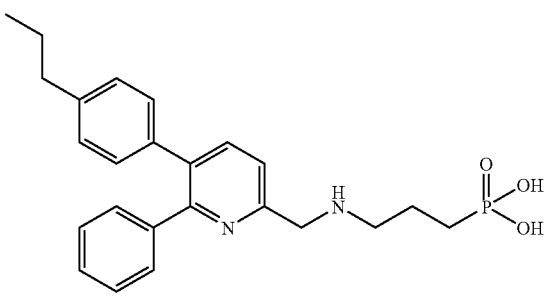 [SMILES: CCCc1ccc(-c2ccc(CNCCCP(=O)(O)O)nc2-c2ccccc2)cc1]
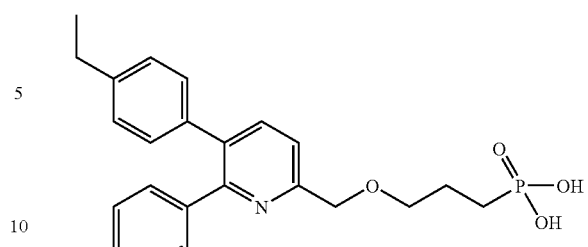
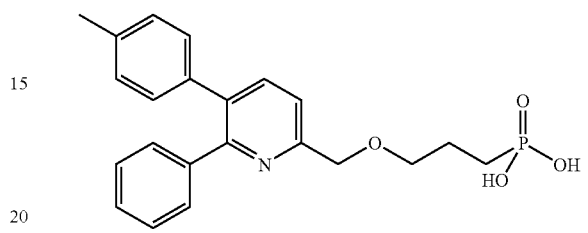
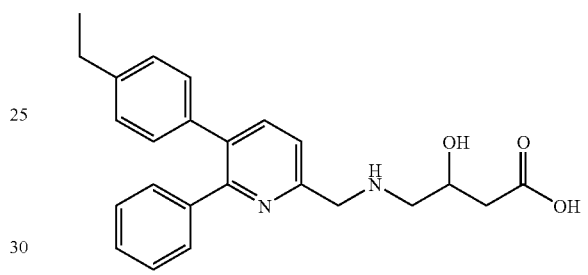
58. The method of 57, wherein the compound is selected from the group consisting of
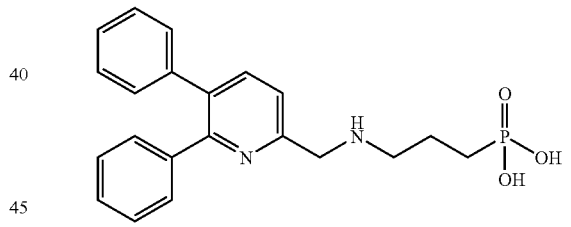
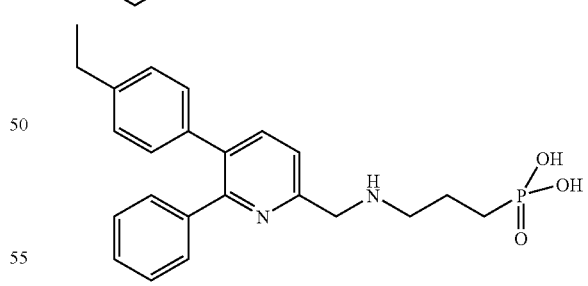
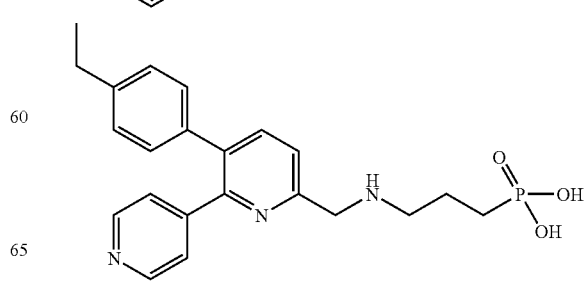

59. A method of treating pain, the method comprising the step of administering to a patient in need of such treatment an S1P3 receptor inhibitor comprising a 6-membered heteroaromatic ring including one, two or three enchained nitrogen atoms and the remaining ring atoms being carbon, an aryl radical directly bonded to said 6-membered heteroaromatic ring at both of the 5 and 6 positions and a side chain at the 2 position of said 6-membered heteroaromatic ring, wherein said side chain terminates with an end group selected from the group consisting of a phosphonic acid, a lower alkyl ester thereof, a carboxylic acid, a lower alkyl ester thereof, a lower alkyl ether and a lower alkylcarboxy, and any pharmaceutically acceptable salt thereof.

60. The method of 59, wherein the one, two or three enchained nitrogen atoms are at the 1, or 1 and 3, or 1 and 4, or 1, 3 and 4 positions, respectively.

61. A method for treating pain, the method comprising administering to a patient in need of such treatment a compound represented by the general formula:

wherein $R_1$ and $R_2$ are each independently $(CH_2)_n$, wherein n is an integer from 1 to 4;
A and B are each independently an aryl ring having 0, 1, 2, or 3 substituents consisting of from 0 to 8 carbon atoms, 0 to 3 oxygen atoms, 0 to 3 halogen atoms, 0 to 2 nitrogen atoms, 0 to 2 sulfur atoms, and from 0 to 24 hydrogen atoms;
X and Y are each independently H, alkyl of 1 to 8 carbons, or hydroxyalkyl of 1 to 8 carbons; and
Z is O or S.

62. The method of 61, wherein the compound is represented by the general formula wherein X and Y are each independently H, unsubstituted alkyl of 1 to 4 carbons, hydroxyl, or unsubstituted alkoxy of 1 to 4 carbons.

63. The method of 61, wherein the compound is selected from the group consisting of
1-benzyl-N-(3,4-difluorobenzyl)-2-isopropyl-6-propoxy-1H-indole-3-carboxamide, 1-benzyl-N-(3,4-difluorobenzyl)-6-isopropoxy-2-isopropyl-1H-indole-3-carboxamide,
1-benzyl-N-(3,4-difluorobenzyl)-5-hydroxy-2-isopropyl-1H-indole-3-carboxamide, 1-benzyl-2-cyclopentyl-N-(3,4-difluorobenzyl)-5-hydroxy-1H-indole-3-carboxamide,
1-benzyl-N-(3,4-difluorobenzyl)-6-ethoxy-2-isopropyl-1H-indole-3-carboxamide, 1-benzyl-N-(3,4-difluorobenzyl)-2-isopropyl-1H-indole-3-carboxamide, and
2-cyclopentyl-N-(3,4-difluorobenzyl)-5-hydroxy-1-(pyridin-2-ylmethyl)-1H-indole-3-carboxamide.

64. A method for treating pain, the method comprising administering to a patient in need of such treatment a compound represented by the general formula wherein A is a phenyl ring having 0, 1, 2, or 3 substituents consisting of from 0 to 6 carbon atoms and from 0 to 13 hydrogen atoms; and
Z is $(CH_2)_n$, wherein n is an integer from 1 to 4.

65. The method of 64, wherein the compound is 3-((5-(4-ethylphenyl)-6-phenylpyridin-2-yl)methylamino)propylphosphonic acid.

What is claimed is:

1. A method for treating pain, the method comprising the step of administering to a patient in need of such treatment a compound at least one compound selected from the group consisting of:

101
-continued
102
-continued
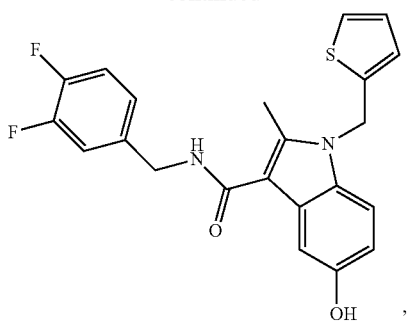
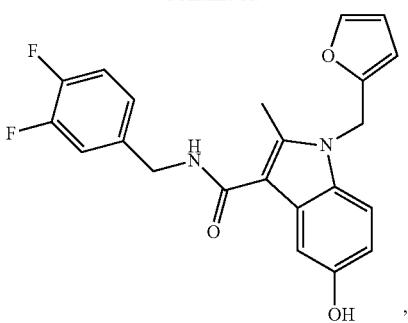

103
-continued
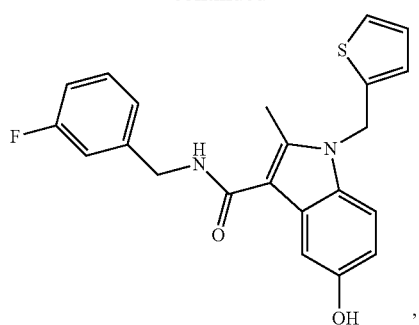
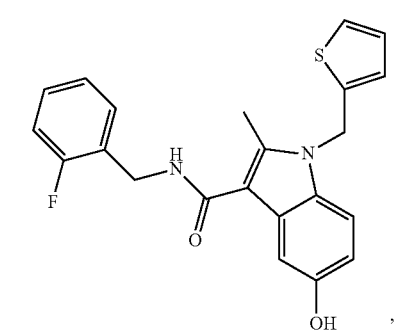
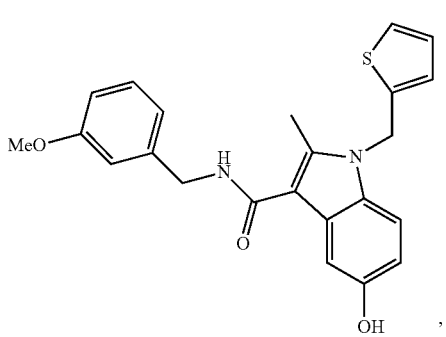
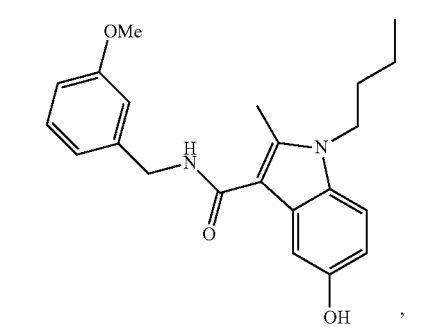
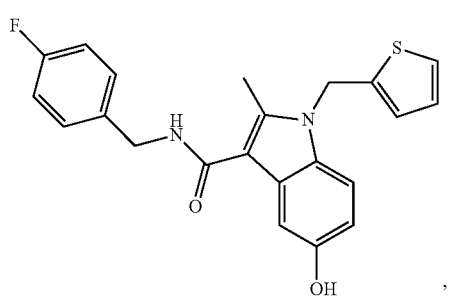
104
-continued
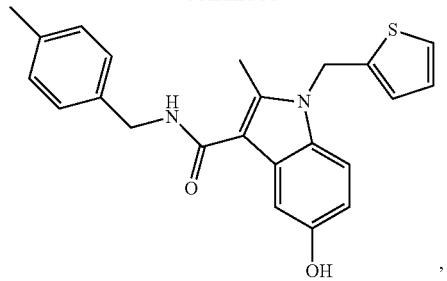
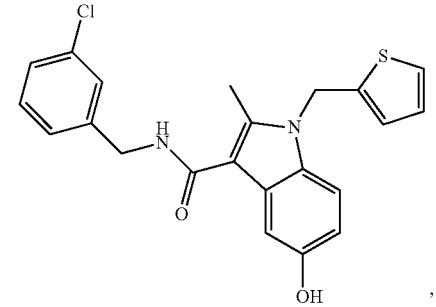
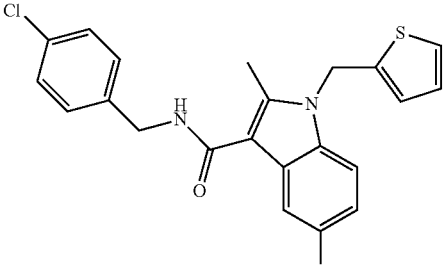
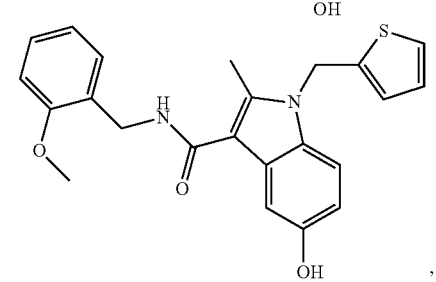
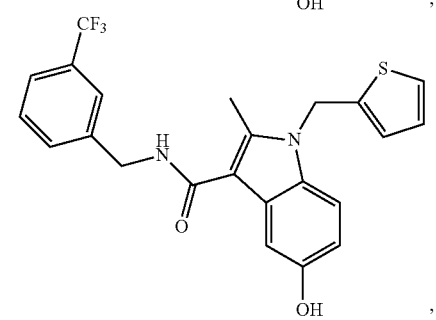
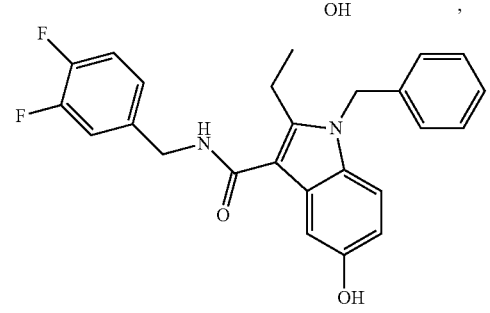

105
-continued
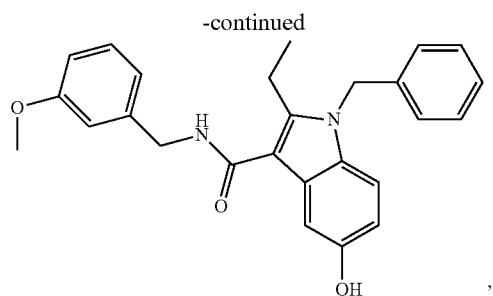
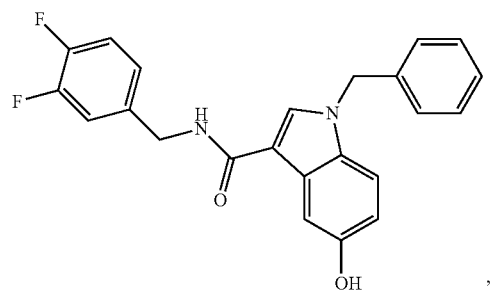
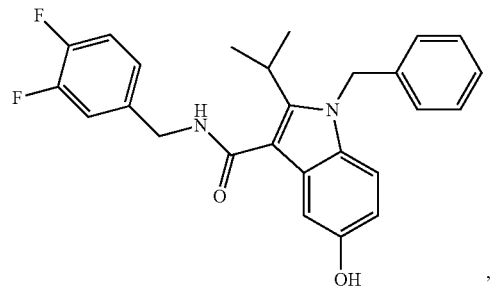
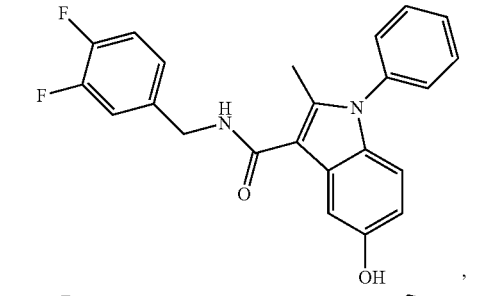
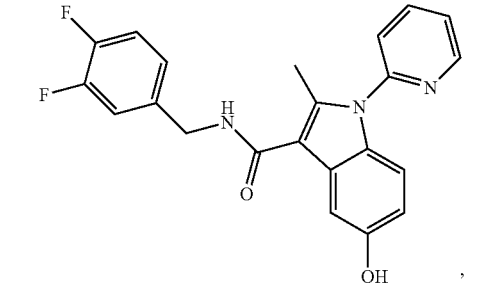
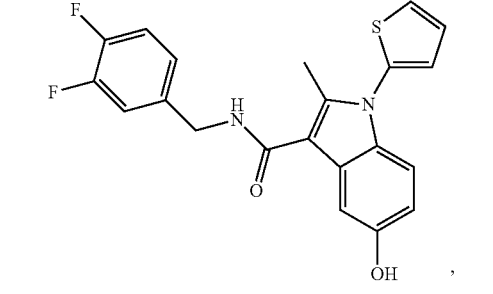
106
-continued
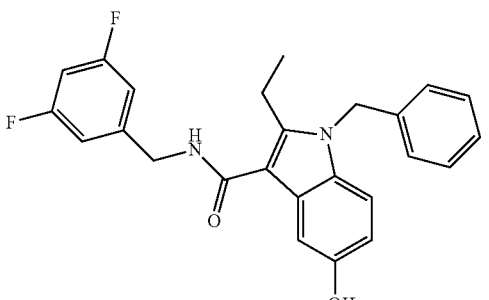
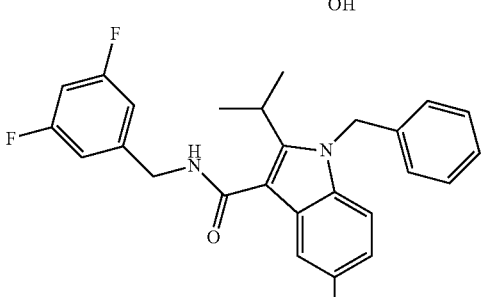
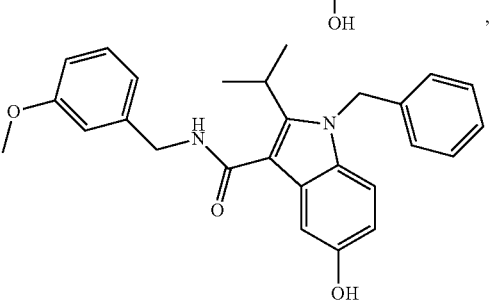
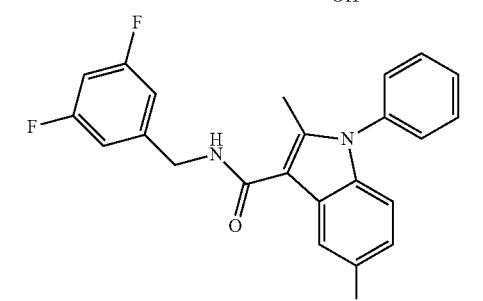
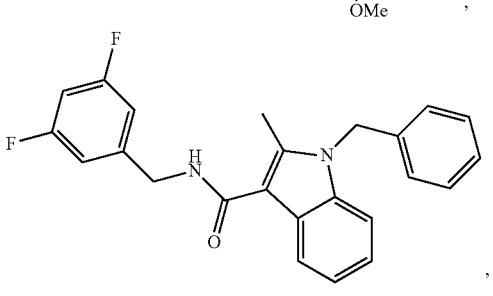
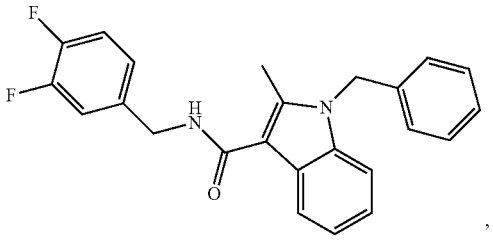

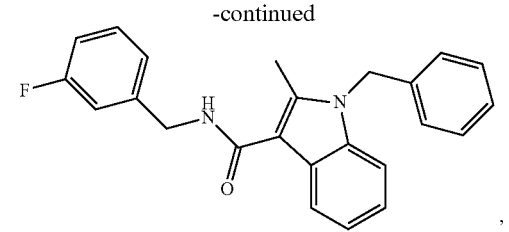
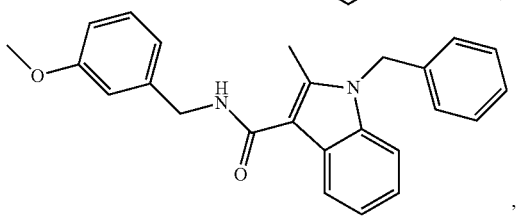
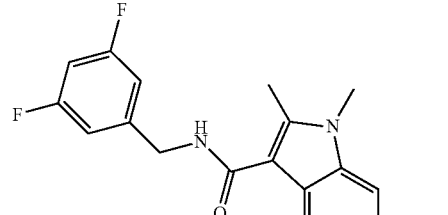
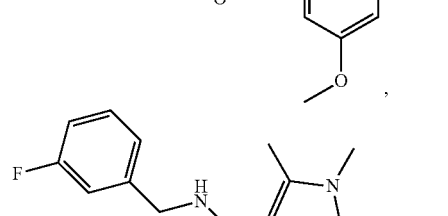
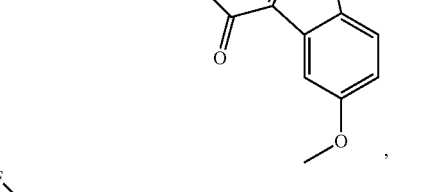
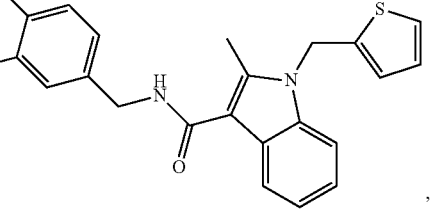
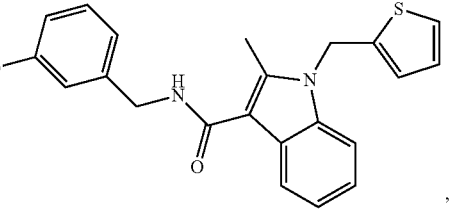
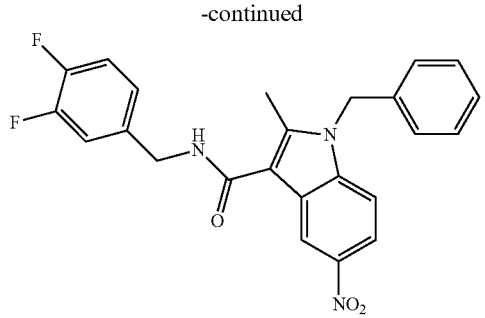
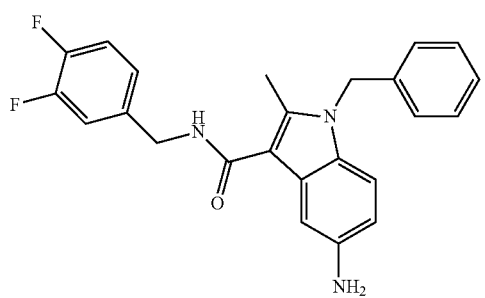
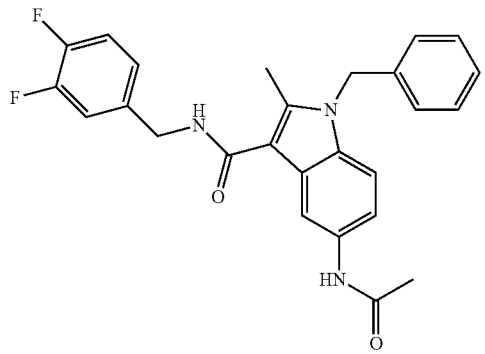
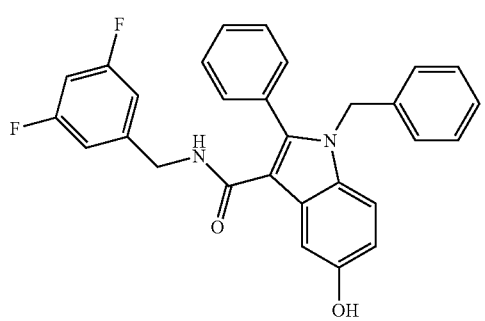
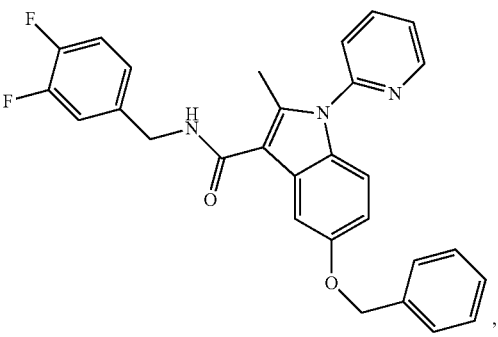

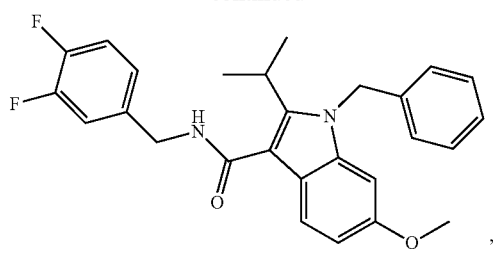
,
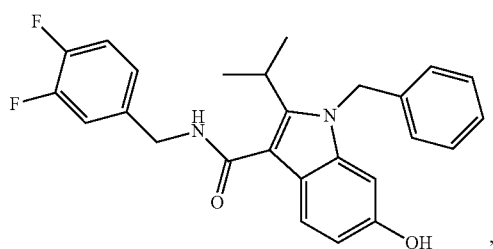
,
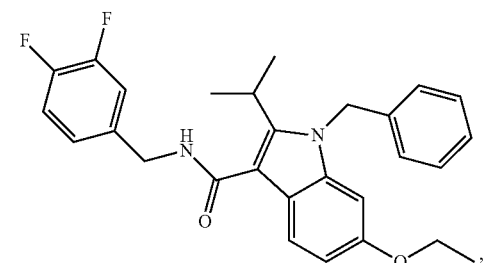
,
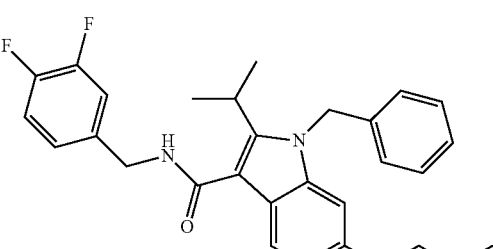
,
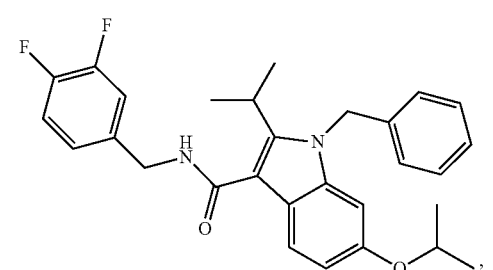
,
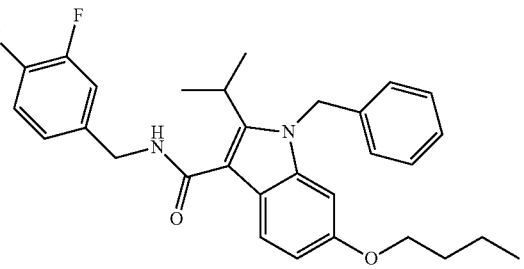
,
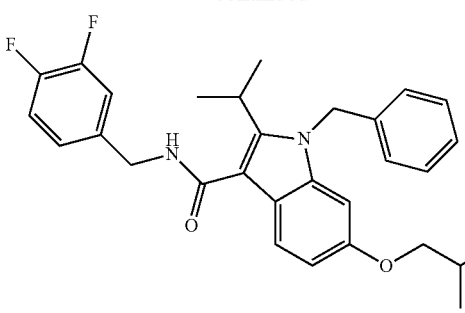
,
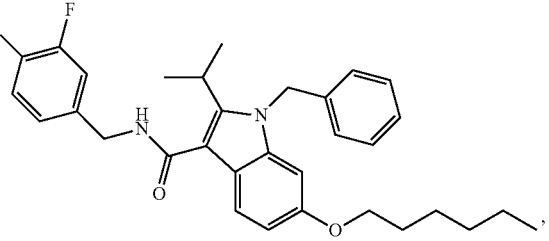
,
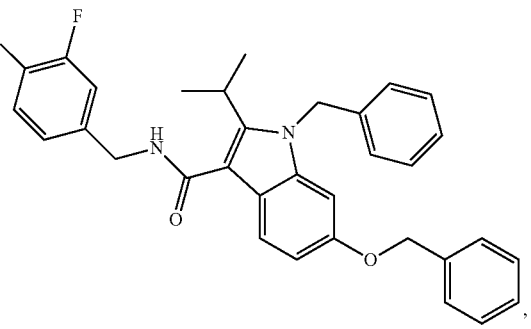
,
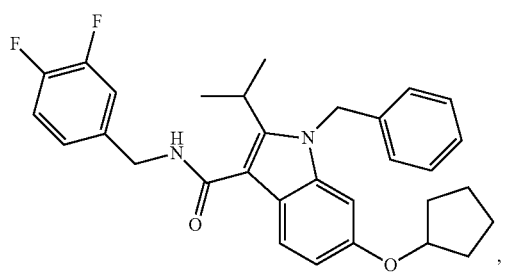
,
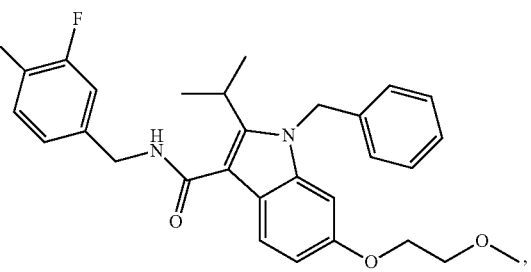
,
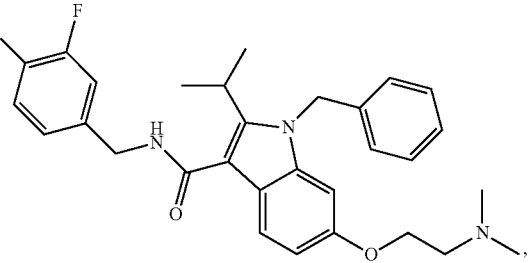
, 111
-continued
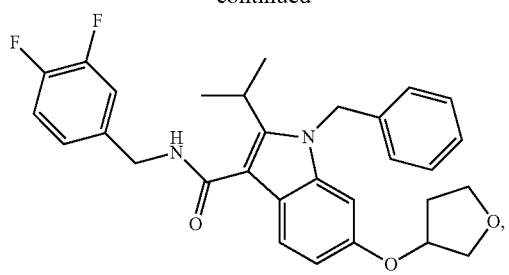
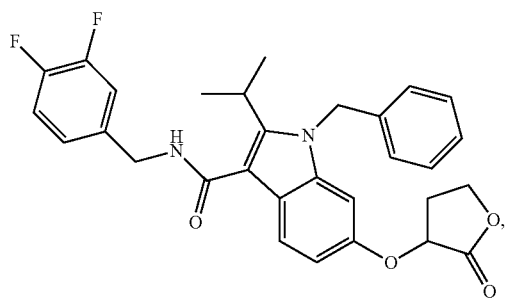
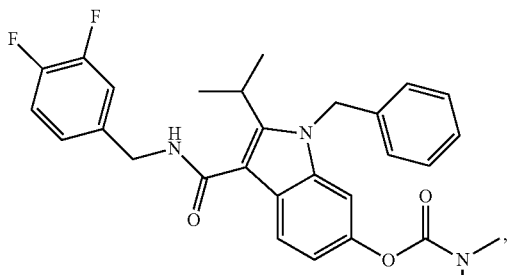
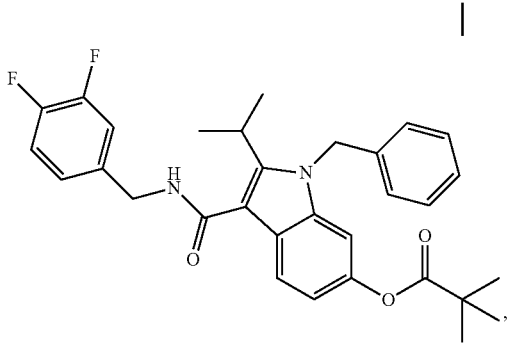
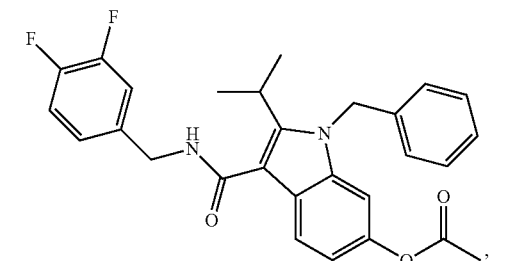
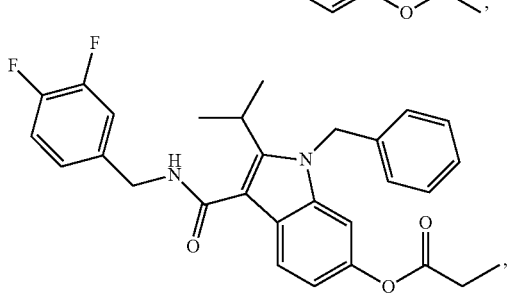
112
-continued
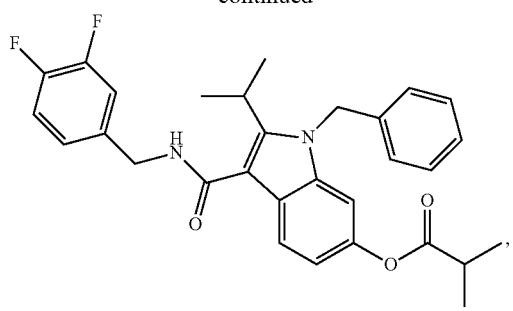
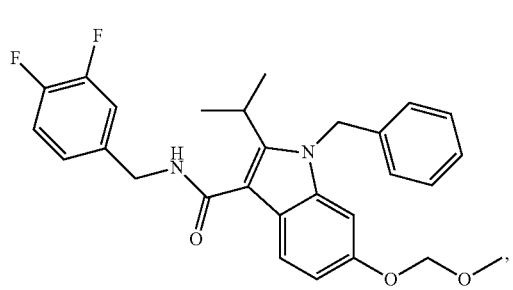
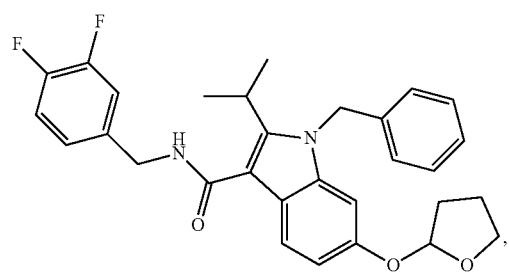
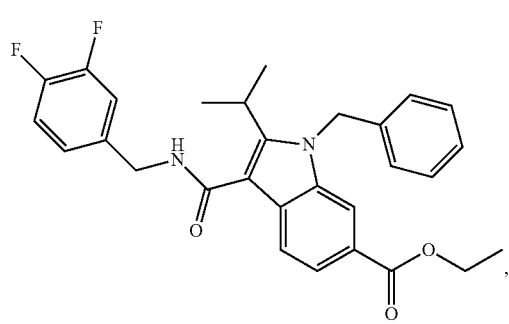
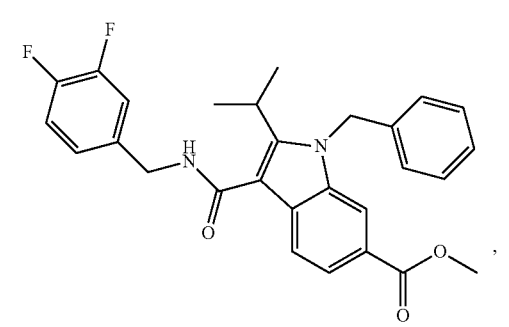

113
-continued
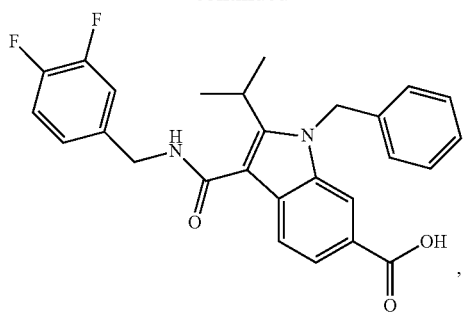
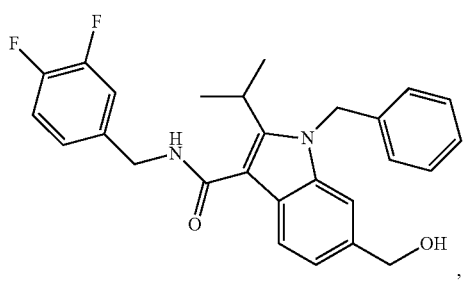
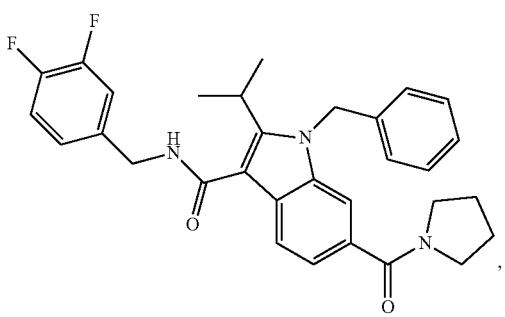
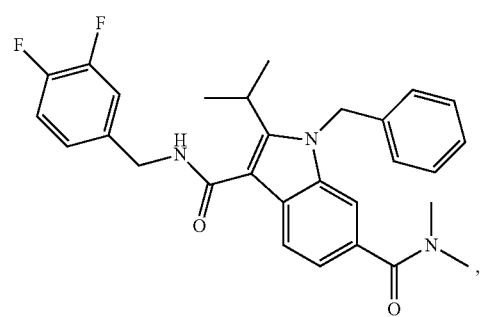
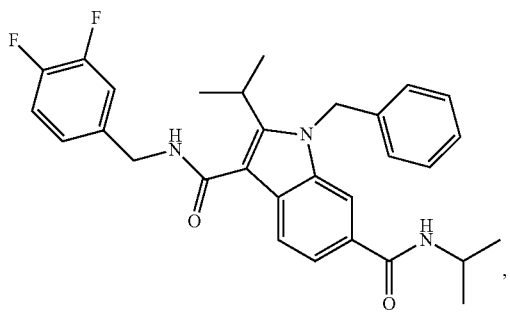
114
-continued
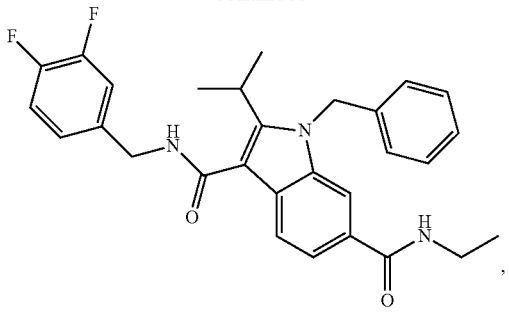
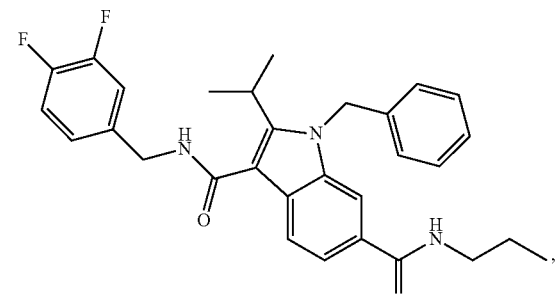
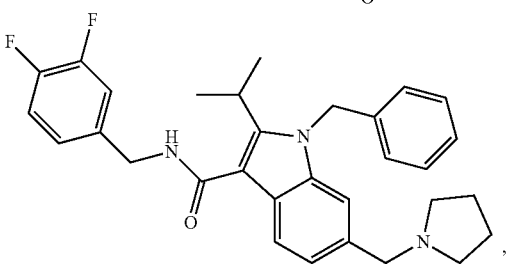
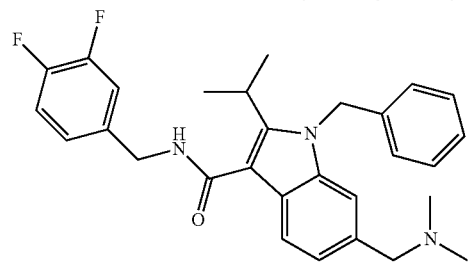
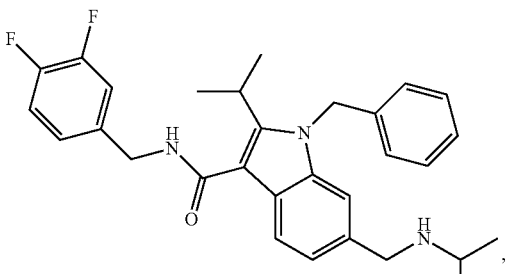
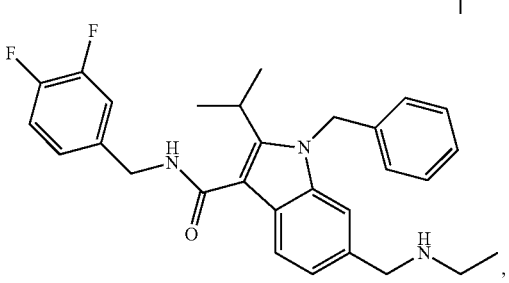

115
-continued
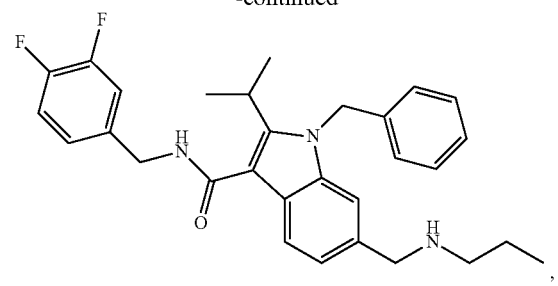
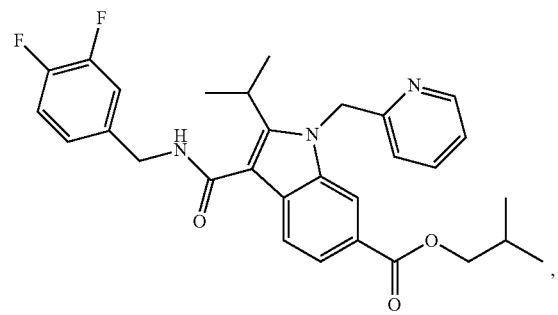
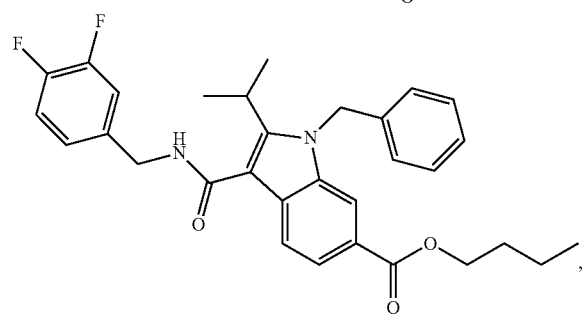
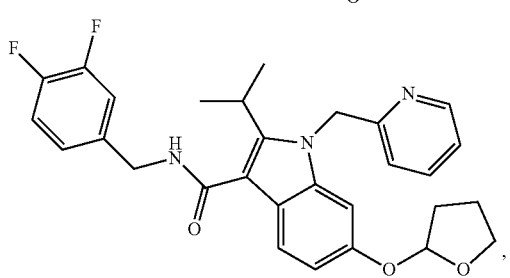
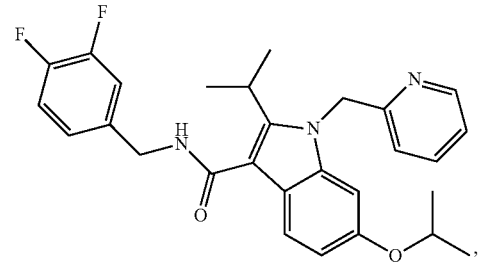
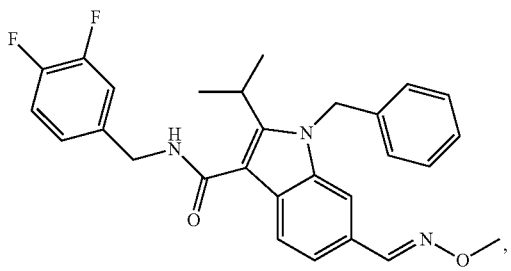
116
-continued
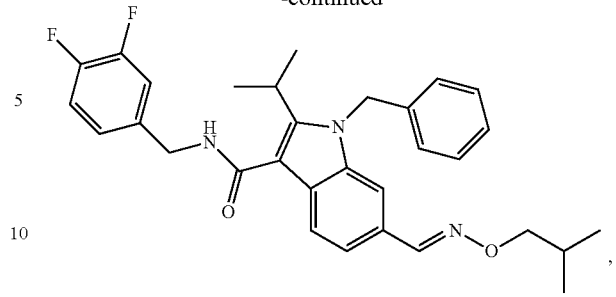
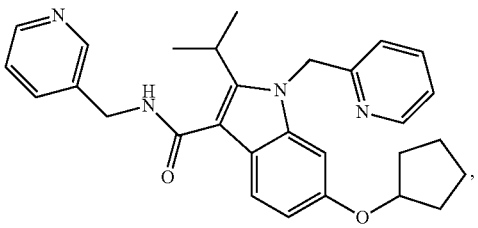
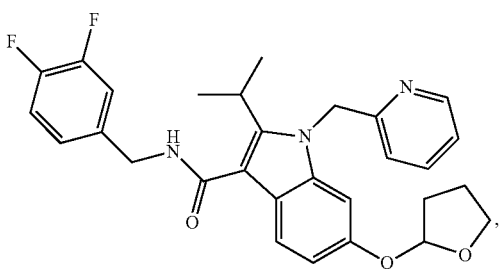
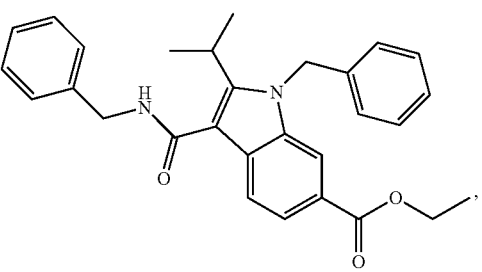
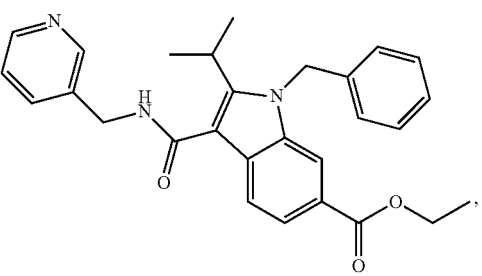
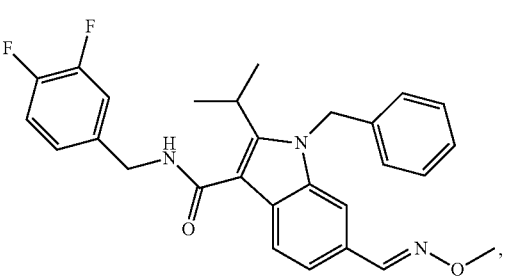

117
-continued
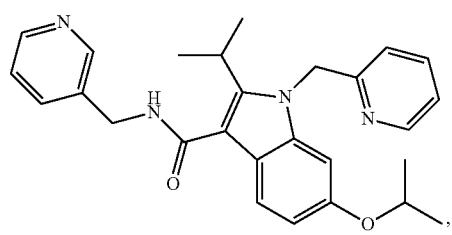
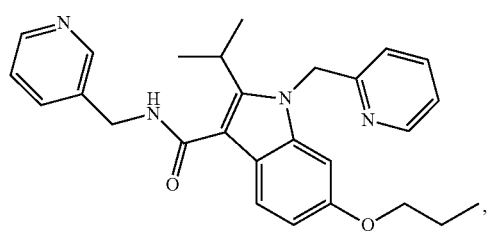
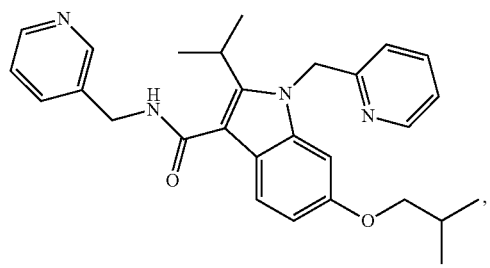
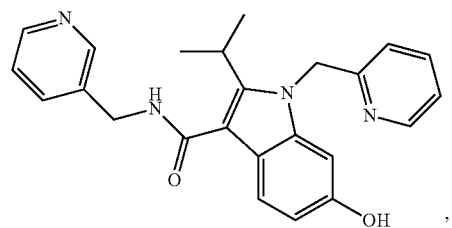
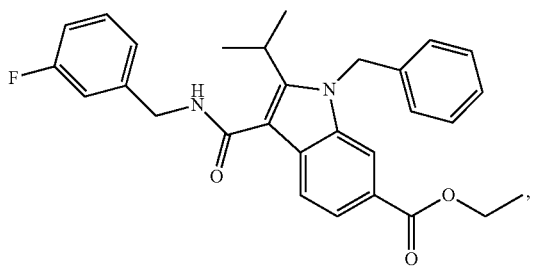
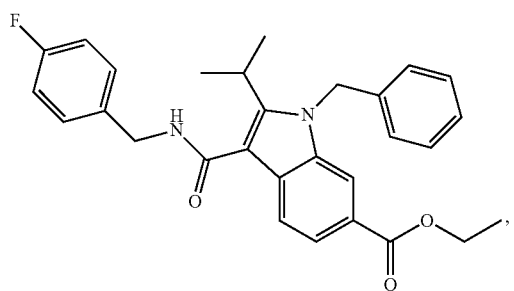
118
-continued
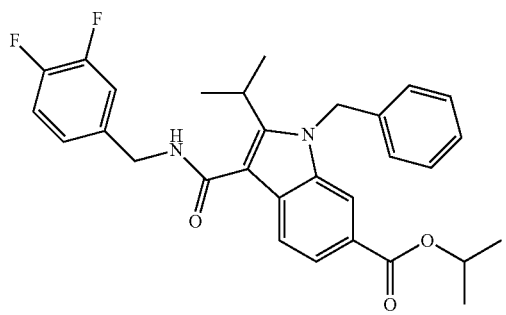
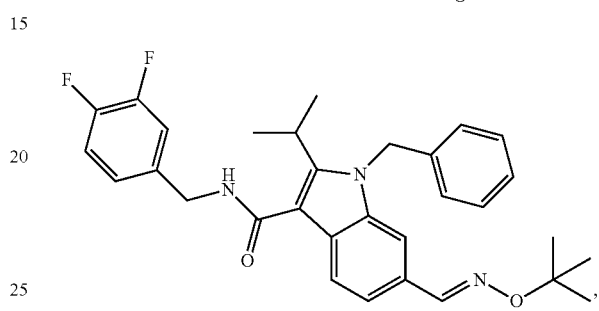
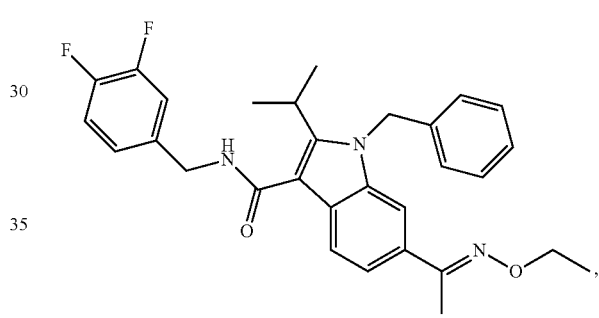
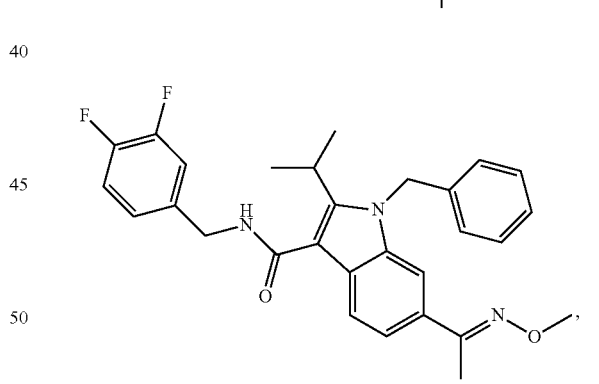
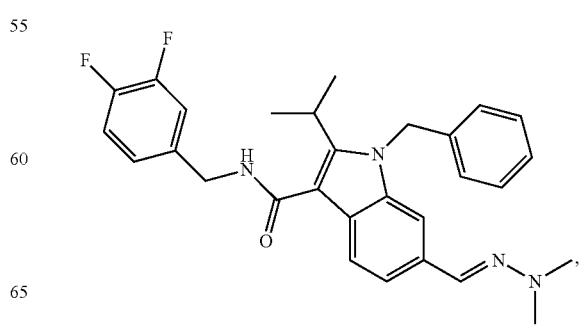

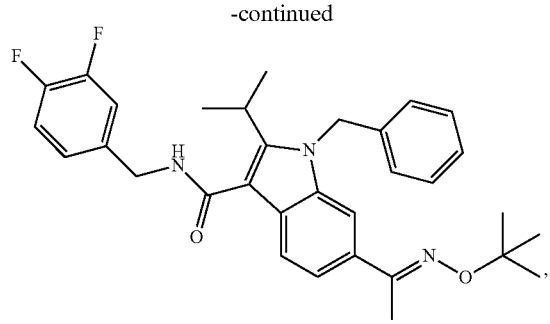
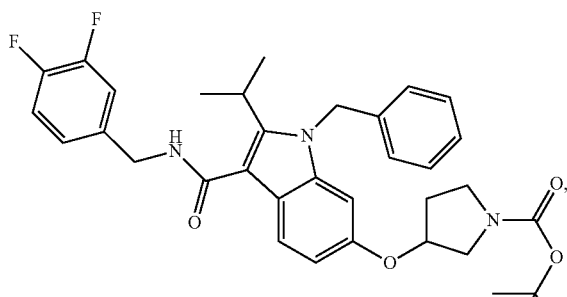
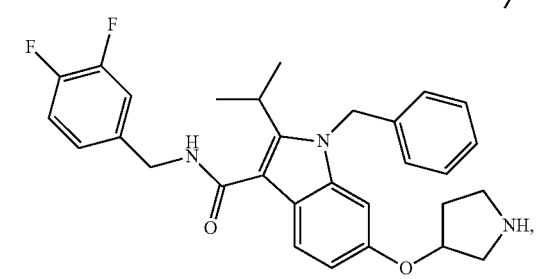
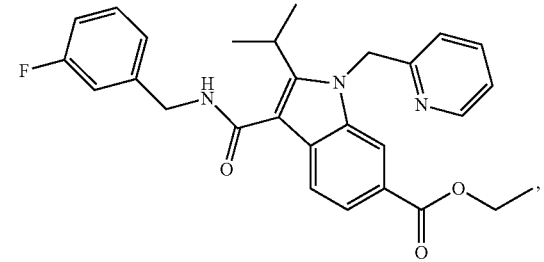
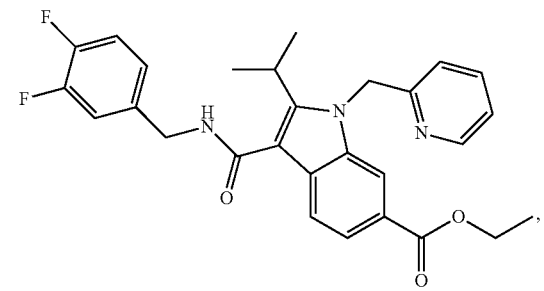
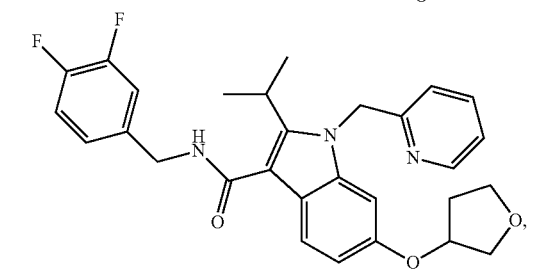
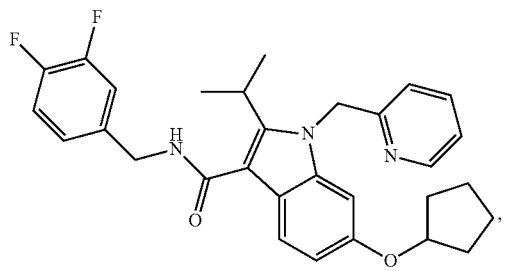
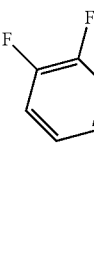
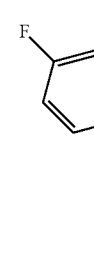
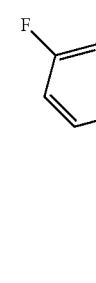
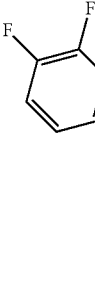
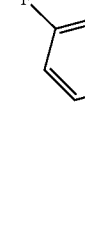

121
-continued
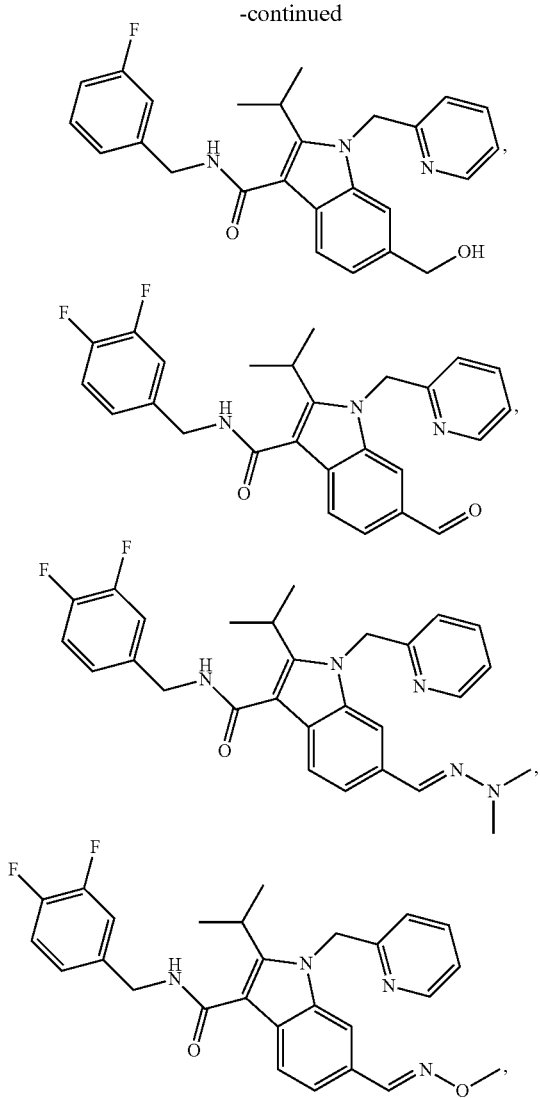
122
-continued
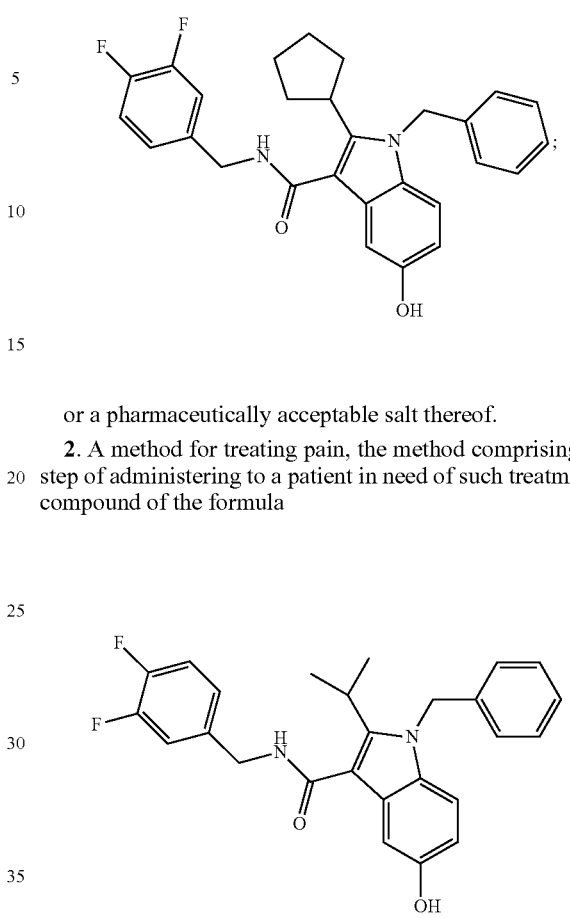
or a pharmaceutically acceptable salt thereof.
2. A method for treating pain, the method comprising the step of administering to a patient in need of such treatment a compound of the formula
or a pharmaceutically acceptable salt thereof.
* * * * *